(12) United States Patent
Greaves

(10) Patent No.: US 8,840,684 B2
(45) Date of Patent: Sep. 23, 2014

(54) PROCESS FOR DYEING KERATIN FIBRES USING A DIRECT DYE BEARING A DISULFIDE/THIOL/PROTECTED THIOL FUNCTION AND WATER VAPOUR

(75) Inventor: Andrew Greaves, Magny-le-Hongre (FR)

(73) Assignee: l'oreal, Paris (FR)

( * ) Notice: Subject to any disclaimer, the term of this patent is extended or adjusted under 35 U.S.C. 154(b) by 0 days.

(21) Appl. No.: 13/993,416

(22) PCT Filed: Dec. 5, 2011

(86) PCT No.: PCT/EP2011/071742
§ 371 (c)(1),
(2), (4) Date: Jun. 12, 2013

(87) PCT Pub. No.: WO2012/093041
PCT Pub. Date: Jul. 12, 2012

(65) Prior Publication Data
US 2013/0283544 A1 Oct. 31, 2013

(30) Foreign Application Priority Data
Dec. 15, 2010 (FR) ........................................ 1060527

(51) Int. Cl.
*A61Q 5/10* (2006.01)
(52) U.S. Cl.
USPC ................ 8/405; 8/426; 8/432; 8/435; 8/465; 8/587; 8/648; 132/202; 132/208
(58) Field of Classification Search
USPC ............. 8/405, 426, 432, 534, 465, 587, 648; 132/202, 208
See application file for complete search history.

(56) References Cited

U.S. PATENT DOCUMENTS

| | | | |
|---|---|---|---|
| 3,100,739 | A | 8/1963 | Kaiser et al. |
| 3,524,842 | A | 8/1970 | Grossmann et al. |
| 3,617,163 | A | 11/1971 | Kalopissis et al. |
| 3,665,036 | A | 5/1972 | Kalopissis et al. |
| 3,817,698 | A | 6/1974 | Kalopissis et al. |
| 3,867,456 | A | 2/1975 | Kalopissis et al. |
| 3,869,454 | A | 3/1975 | Lang et al. |
| 3,955,918 | A | 5/1976 | Lang |

(Continued)

FOREIGN PATENT DOCUMENTS

| | | |
|---|---|---|
| DE | 257638 | 3/1921 |
| DE | 25 38 363 | 5/1976 |

(Continued)

*Primary Examiner* — Eisa Elhilo
(74) *Attorney, Agent, or Firm* — The Marbury Law Group, PLLC

(57) ABSTRACT

The invention relates to a process for dyeing and/or lightening keratin fibers such as the hair, using i) at least one cationic direct dye bearing a disulfide, thiol or protected thiol function especially of formula (I) as defined in the description and ii) water vapor. The invention also relates to the use i) of at least one cationic direct dye bearing a disulfide, thiol or protected thiol function combined with ii) water vapor, for dyeing and lightening keratin fibers, and to the use of water vapor for grafting onto keratin fibers dyes bearing a disulfide, thiol or protected thiol function. The process used and the use of thiol, protected thiol or disulfide dyes combined with water vapor makes it possible especially to obtain a long-lasting coloration on keratin fibers without the use of a reducing agent and without odor.

19 Claims, 3 Drawing Sheets

(56) References Cited

U.S. PATENT DOCUMENTS

Figure 1:
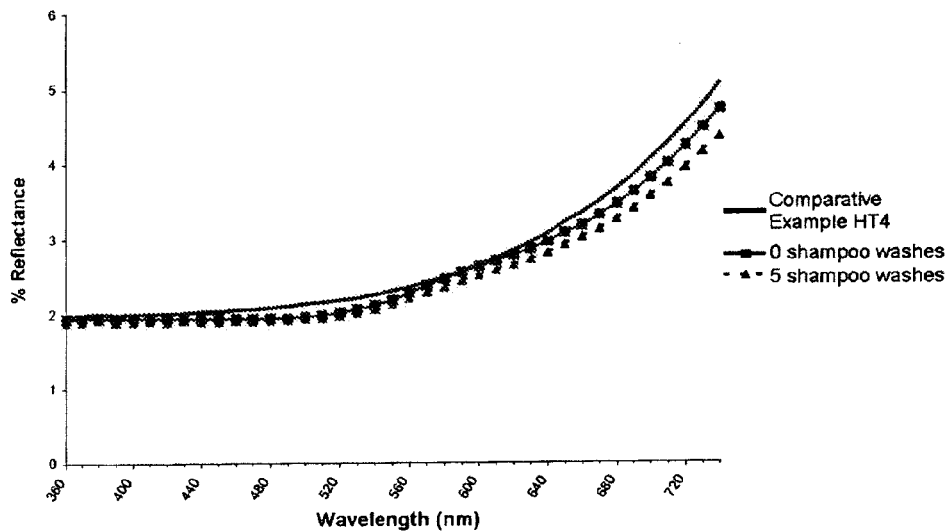

| | | | |
|---|---|---|---|
| 3,985,499 | A | 10/1976 | Lang et al. |
| 4,025,301 | A | 5/1977 | Lang |
| 4,151,162 | A | 4/1979 | Lang et al. |
| 4,226,784 | A | 10/1980 | Kalopissis et al. |
| 4,886,517 | A | 12/1989 | Bugaut et al. |
| 5,708,151 | A | 1/1998 | Möckli |
| 5,711,765 | A | 1/1998 | Audousset |
| 5,879,413 | A | 3/1999 | Pengilly et al. |
| 5,888,252 | A | 3/1999 | Möckli |
| 5,919,273 | A | 7/1999 | Rondeau et al. |
| 5,944,360 | A | 8/1999 | Crapart |
| 5,993,490 | A | 11/1999 | Rondeau et al. |
| 6,045,591 | A | 4/2000 | Deneulenaere |
| 6,136,042 | A | 10/2000 | Maubru |
| 6,179,881 | B1 | 1/2001 | Henrion et al. |
| 6,451,069 | B2 | 9/2002 | Matsunaga et al. |
| 6,458,167 | B1 | 10/2002 | Genet et al. |
| 6,492,502 | B2 | 12/2002 | Henrion et al. |
| 6,797,013 | B1 | 9/2004 | Lang et al. |
| 6,863,883 | B1 | 3/2005 | Tsujino et al. |
| 7,717,964 | B2 | 5/2010 | Daubresse et al. |
| 7,744,657 | B2 | 6/2010 | Greaves et al. |
| 7,780,743 | B2 | 8/2010 | Greaves et al. |
| 8,038,731 | B2 | 10/2011 | Daubresse et al. |
| 8,328,880 | B2 | 12/2012 | Daubresse et al. |
| 2001/0001332 | A1 | 5/2001 | Henrion et al. |
| 2001/0044975 | A1 | 11/2001 | Matsunaga et al. |
| 2002/0165368 | A1 | 11/2002 | Henrion et al. |
| 2006/0080791 | A1 | 4/2006 | Daubresse et al. |
| 2009/0126125 | A1 | 5/2009 | Greaves et al. |
| 2009/0172897 | A1 | 7/2009 | Daubresse et al. |
| 2009/0313769 | A1* | 12/2009 | Daubresse et al. ........... 8/406 |
| 2009/0320216 | A1 | 12/2009 | Greaves et al. |
| 2010/0287714 | A1 | 11/2010 | Greaves et al. |
| 2011/0011417 | A1 | 1/2011 | Greaves et al. |
| 2012/0177587 | A1 | 7/2012 | Daubresse et al. |
| 2013/0074276 | A1 | 3/2013 | Daubresse et al. |

FOREIGN PATENT DOCUMENTS

| | | |
|---|---|---|
| DE | 41 37 005 | 5/1993 |
| DE | 42 20 388 | 12/1993 |
| EP | 0 714 954 | 6/1995 |
| EP | 0 705 597 | 4/1996 |
| EP | 0 850 636 | 7/1998 |
| EP | 0 850 637 | 7/1998 |
| EP | 0 860 636 | 8/1998 |
| EP | 0 918 053 | 5/1999 |
| EP | 0 920 856 | 6/1999 |
| EP | 1 062 940 | 12/2000 |
| EP | 1 133 975 | 9/2001 |
| EP | 1 133 976 | 9/2001 |
| EP | 1 647 580 | 4/2006 |
| EP | 2 070 988 | 6/2009 |
| EP | 2 075 289 | 7/2009 |
| FR | 1 560 664 | 11/1954 |
| FR | 1 540 423 | 9/1958 |
| FR | 1 221 122 | 5/1960 |
| FR | 1 516 943 | 3/1968 |
| FR | 1 567 219 | 5/1969 |
| FR | 2 189 006 | 1/1974 |
| FR | 2 285 851 | 4/1975 |
| FR | 2 275 462 | 1/1976 |
| FR | 2 570 946 | 4/1986 |
| FR | 2 757 385 | 6/1998 |
| FR | 2 788 433 | 7/2000 |
| GB | 738 585 | 10/1955 |
| GB | 1 163 385 | 9/1969 |
| GB | 1 195 386 | 6/1970 |
| GB | 1 514 466 | 6/1978 |
| WO | 95/01772 | 1/1995 |
| WO | 95/15144 | 6/1995 |
| WO | 97/44004 | 11/1997 |
| WO | 99/48465 | 9/1999 |
| WO | 01/66646 | 9/2001 |
| WO | 03/029359 | 4/2003 |
| WO | 2005/097051 | 10/2005 |
| WO | 2007/110531 | 10/2007 |
| WO | 2007/110532 | 10/2007 |
| WO | 2007/110533 | 10/2007 |
| WO | 2007/110534 | 10/2007 |
| WO | 2007/110535 | 10/2007 |
| WO | 2007/110536 | 10/2007 |
| WO | 2007/110537 | 10/2007 |
| WO | 2007/110538 | 10/2007 |
| WO | 2007/110539 | 10/2007 |
| WO | 2007/110540 | 10/2007 |
| WO | 2007/110541 | 10/2007 |
| WO | 2007/110542 | 10/2007 |
| WO | 2009/034059 | 3/2009 |
| WO | 2009/040354 | 4/2009 |

* cited by examiner

Protocol 1/dye 2 - <u>with</u> treatment with water vapour, 5 shampoo washes - Example 1

Protocol 1/dye 2 - <u>without</u> treatment with water vapour, 5 shampoo washes - Example 2

Protocol 1/dye 1 - <u>without</u> treatment with water vapour, 5 shampoo washes - Example 3

Protocol 1/dye 1 - <u>with</u> treatment with water vapour, 5 shampoo washes - Example 4

Protocol 2/dye 1 - <u>without</u> treatment with water vapour, 5 shampoo washes
« comparative disulfide dye of formula (I) + reducing agent - Example 5

PROCESS FOR DYEING KERATIN FIBRES USING A DIRECT DYE BEARING A DISULFIDE/THIOL/PROTECTED THIOL FUNCTION AND WATER VAPOUR

This is a national stage application of PCT/EP2011/071742, filed internationally on Dec. 5, 2011, which claims priority to French Application FR 1060527, filed on Dec. 15, 2010.

The invention relates to a process for dyeing and/or lightening keratin fibres such as the hair, using i) at least one cationic direct dye bearing a disulfide, thiol or protected thiol function and ii) water vapour. The invention also relates to the use i) of at least one cationic direct dye bearing a disulfide, thiol or protected thiol function combined with ii) water vapour, for dyeing and lightening keratin fibres, and to the use of water vapour for grafting onto keratin fibres cationic direct dyes bearing a disulfide, thiol or protected thiol function.

The process used and the use of thiol, protected thiol or disulfide dyes combined with water vapour makes it possible especially to obtain a long-lasting coloration on keratin fibres without the use of a reducing agent and without odour.

It is known practice to dye keratin fibres by direct dyeing or semi-permanent dyeing. Direct dyeing or semi-permanent dyeing consists in introducing colour via a coloured molecule that becomes adsorbed onto the surface of the hair or that penetrates into the hair. Thus, the process conventionally used in direct dyeing consists in applying to keratin fibres direct dyes, which are coloured and colouring molecules that have affinity for the fibres, leaving the fibres in contact with the colouring molecules and then rinsing the fibres. Generally, this technique leads to chromatic colorations.

Scientific research has been conducted for several years to modify the colour of keratin materials, especially keratin fibres, and in particular to mask white fibres, to modify the colour of the fibres permanently or temporarily, and to satisfy new desires and needs in terms of colours and durability.

Patent applications EP 1 647 580, WO 2005/097 051, EP 2 004 759, EP 2 075 289, WO 2007/110 541, WO 2007/110 540, WO 2007/110 539, WO 2007/110 538, WO 2007/110 537, WO 2007/110 536, WO 2007/110 535, WO 2007/110 534, WO 2007/110 533, WO 2007/110 532, WO 2007/110 531, EP 2 070 988, WO 2009/040 354 and WO 2009/034 059 disclose direct dyes bearing a disulfide, thiol or protected thiol function, which may be grafted onto the hair using a reductive treatment. Now, the majority of reducing agents have a tendency to impair the integrity of keratin fibres, having the effect of making them brittle. In addition, when combined with dyes bearing a disulfide function, reducing agents generally generate unpleasant odours.

It is also known practice to use water vapour combined with a carrier gas, and cationic direct dyes for dyeing the hair (EP 0 705 597). The colorations obtained with this process are not sufficiently satisfactory especially in terms of remanence of the coloration.

The aim of the present invention is to provide novel hair dyeing systems for obtaining odourless or virtually odourless colorations, which are fast with respect to external agents, homogeneous and very strong, and/or which do not impair the cosmetic properties of keratin fibres, and to do so without the use of a reducing agent and/or of a chemical oxidizing agent.

Another aim of the invention is to provide a dyeing system for obtaining visible colorations on naturally or artificially dark keratin fibres, with lightening effects even in the absence of a chemical oxidizing agent, without degradation of the fibre, and whose coloration remains remanent with respect to external agents such as shampoos.

These aims are achieved with the present invention, a first subject of which is a process for dyeing keratin fibres, especially human keratin fibres such as the hair, comprising steps i) and ii) below:

i) applying to the fibres at least one cationic direct dye bearing a disulfide function, a thiol function or a protected thiol function, especially of formula (I):

$$A\text{-}(X)_p\text{—}C_{sat}\text{—}S\text{—}U \tag{I}$$

salts thereof with an organic or mineral acid, optical or geometric isomers thereof, tautomers thereof, and solvates thereof such as the hydrates, in which formula (I):

U represents a radical chosen from:
a) —S—$C'_{sat}$—$(X')_{p'}$-A'; and
b) —Y;

A and A', which may be identical or different, represent a radical containing at least one cationic chromophore;

Y represents i) a hydrogen atom; or ii) a thiol-function protecting group;

X and X', which may be identical or different, represent a linear or branched, saturated or unsaturated divalent $C_1$-$C_{30}$ hydrocarbon-based chain, optionally interrupted and/or optionally terminated at one or both of its ends with one or more divalent groups or combinations thereof chosen from:
—N(R)—, —N$^+$(R)(R)—, —O—, —S—, —CO—, —SO$_2$— with R, which may be identical or different, chosen from a hydrogen and a $C_1$-$C_4$ alkyl, hydroxyalkyl or aminoalkyl radical;
an aromatic or non-aromatic, saturated or unsaturated, fused or non-fused (hetero)cyclic radical optionally comprising one or more identical or different, optionally substituted heteroatoms;

p and p', which may be identical or different, are equal to 0 or 1;

$C_{sat}$ and $C'_{sat}$, which may be identical or different represent an optionally cyclic, optionally substituted linear or branched $C_1$-$C_{18}$ alkylene chain; and ii) applying water vapour to the fibres;

steps i) and ii) may be performed together or separately.

Another subject of the invention is the use for dyeing keratin fibres, especially the hair, i) of at least one cationic direct dye bearing a disulfide function, a thiol function or a protected thiol function, especially of formula (I) as defined previously, and ii) water vapour.

A subject of the invention is also the use of water vapour for grafting cationic direct dyes bearing a disulfide, thiol or protected thiol function onto keratin fibres.

The dyeing process of the invention in particular makes it possible to dye in a remanent and odourless manner human keratin fibres such as the hair, while at the same time respecting the integrity of the fibres.

The colorations obtained are aesthetic, very strong and very fast with respect to common attacking factors such as sunlight, perspiration, sebum and other hair treatments such as successive shampooing, while at the same time respecting the keratin fibres. The intensity obtained is particularly noteworthy. The same is true for the colour homogeneity.

FIG. 1 demonstrates results of a study of Protocol 1/dye 2 with water vapour treatment.

Figure 2:
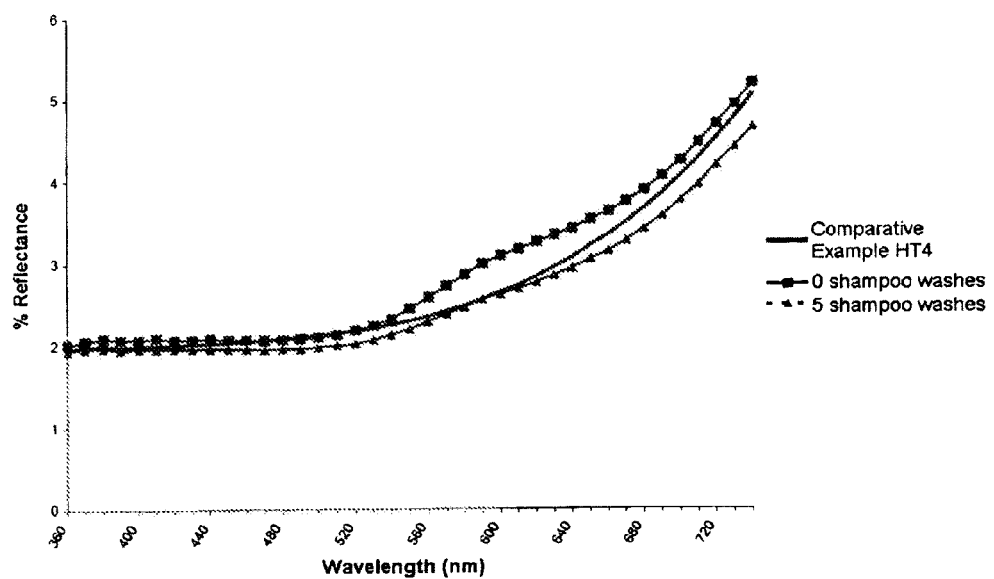

FIG. 2 demonstrates results of a study of Protocol 1/dye 2 without water vapour treatment.

Figure 3:
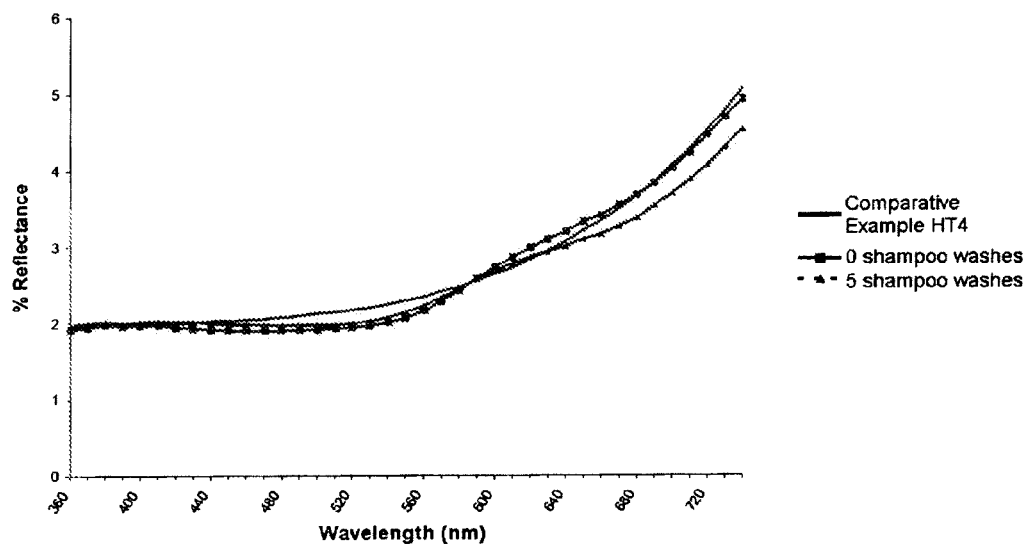

FIG. 3 demonstrates results of a study of Protocol 1/dye 1 without water vapour treatment.

Figure 4:
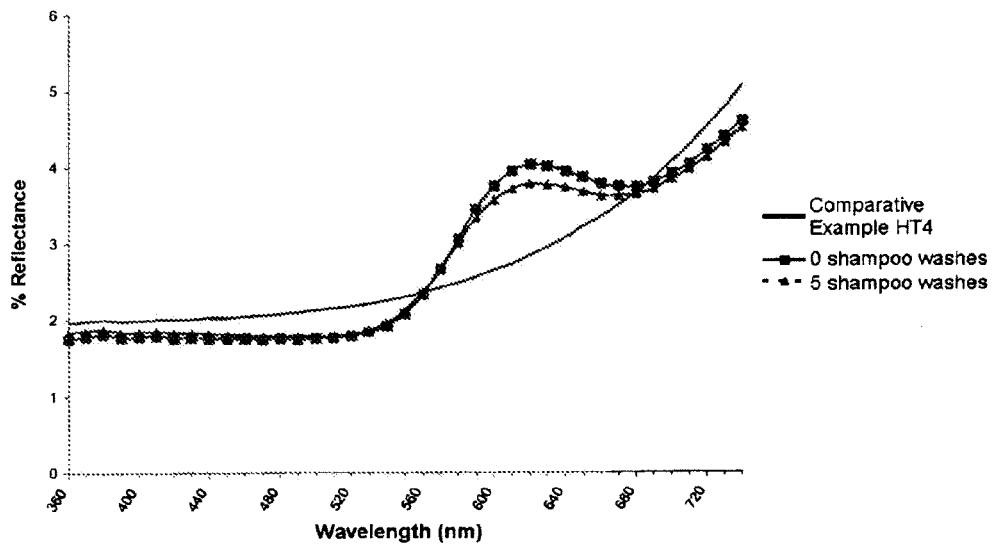

FIG. 4 demonstrates results of a study of Protocol 1/dye 1 with water vapour treatment.

Figure 5:
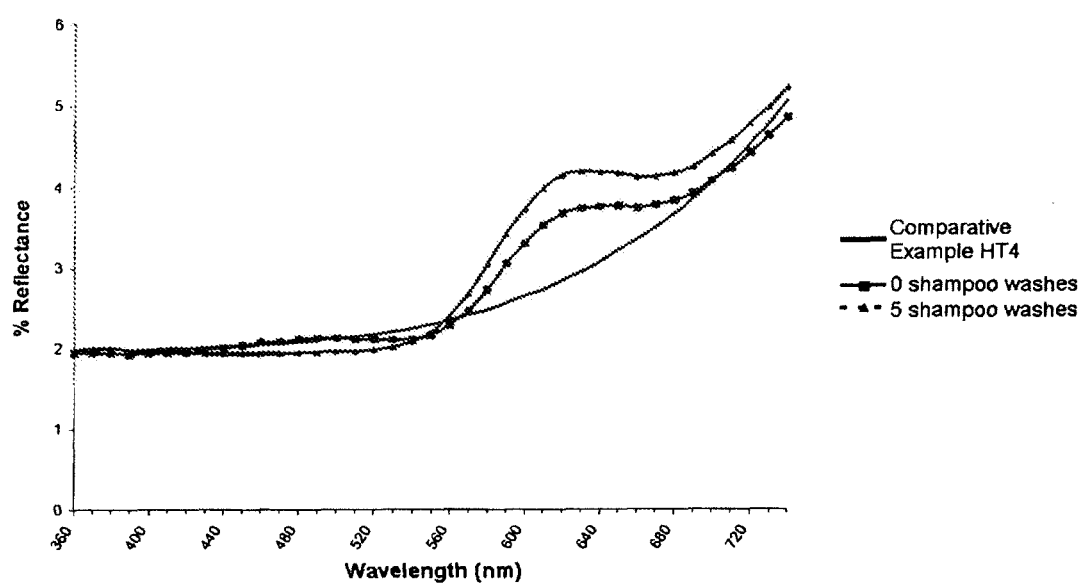

FIG. 5 demonstrates results of a study of Protocol 2/dye 1 without water vapour treatment.

For the purposes of the present invention, and unless otherwise indicated:

- a "cationic direct dye bearing a disulfide function" is a direct dye comprising one or more cationic chromophores that absorb light in the visible spectrum, and comprising a disulfide bond: —S—S— between two carbon atoms and is indirectly bonded to the chromophore(s) of the dye, i.e. between the chromophores and the —S—S— function there is at least one methylene group;
- a "direct dye bearing a protected thiol function" is a direct dye comprising a chromophore, comprising a protected thiol function —SY in which Y is a protecting group known to those skilled in the art, for instance those described in the publications "*Protective Groups in Organic Synthesis*", T. W. Greene, John Wiley & Sons ed., NY, 1981, pp. 193-217; "*Protecting Groups*", P. Kocienski, Thieme, 3$^{rd}$ ed., 2005, chap. 5; and Ullmann's Encyclopedia, "*Peptide Synthesis*", pp. 4-5, 2005 Wiley-VCH Verlag GmbH & Co. KGaA, Weinheim 10.1002/14356007.a19 157; it being understood that the said protected thiol function is indirectly bonded to the chromophore of the dye, i.e. between the chromophore and the function —SY there is at least one methylene group;
- a "direct dye bearing a thiol function" is a direct dye comprising a chromophore, and comprising a thiol function —SY' in which Y' is i) a hydrogen atom; ii) an alkali metal; iii) an alkaline-earth metal; iv) an ammonium group: $N^+R^\alpha R^\beta R^\gamma R^\delta$ or a phosphonium group: $P^+R^\alpha R^\beta R^\gamma R^\delta$ with $R^\alpha$, $R^\beta$, $R^\gamma$ and $R^\delta$, which may be identical or different, representing a hydrogen atom or a group ($C_1$-$C_4$)alkyl, preferentially comprising a thiol function —SH, it being understood that the said thiol function is indirectly bonded to the chromophore of the dye, i.e. between the chromophore and the function —SY' there is at least one methylene group;
- a "chromophore" is a radical derived from a dye, i.e. a radical derived from the molecule that absorbs light in the visible radiation range that is visually and physiologically perceptible by man, i.e. an absorption wavelength $\lambda_{abs}$ inclusively between 400 and 800 nm; the chromophore may be fluorescent, i.e. it is capable of absorbing in the UV and visible radiation range at a wavelength $\lambda_{abs}$ of between 250 and 800 nm and capable of re-emitting in the visible at an emission wavelength $\lambda_{em}$ of between 400 and 800 nm;
- a "chromophore" is said to be "cationic" if it comprises at least one cationic aryl or heteroaryl group as defined below;
- the dyes according to the invention contain one or more chromophores, and these dyes are capable of absorbing light at a wavelength $\lambda_{abs}$ particularly of between 400 and 700 nm inclusive;
- the "fluorescent" dyes according to the invention are dyes containing at least one fluorescent chromophore, and these dyes are capable of absorbing in the visible range at a wavelength $\lambda_{abs}$ particularly between 400 and 800 nm and of re-emitting in the visible range at a longer wavelength $\lambda_{em}$ than that absorbed, of between 400 and 800 nm. The difference between the absorption and emission wavelengths, also known as the Stoke's shift, is between 1 nm and 100 nm. More preferentially, fluorescent dyes are dyes that are capable of absorbing at a wavelength $\lambda_{abs}$ of between 420 and 550 nm and of re-emitting in the visible range at a wavelength $\lambda_{em}$ between 470 and 600 nm;
- chromophores are said to be "different" when they differ in their chemical structure and may be chromophores derived from different families or from the same family on condition that they have different chemical structures: for example, the chromophores may be chosen from the family of azo dyes but differ in the chemical structure of the radicals constituting them or in the respective position of these radicals;
- an "alkylene chain" represents a divalent $C_1$-$C_{20}$, particularly $C_1$-$C_6$ and more particularly $C_1$-$C_2$ chain when the chain is linear; optionally substituted with one or more identical or different groups chosen from hydroxyl, ($C_1$-$C_2$)alkoxy, (poly)hydroxy($C_2$-$C_4$)alkoxy, (di)($C_1$-$C_2$)(alkyl)amino, $R^a$—$Z^a$—$C(Z^b)$—, and $R^a$—$Z^a$—$S(O)_t$— with $Z^a$, $Z^b$, which may be identical or different, representing an oxygen or sulfur atom, or a group $NR^{a'}$, $R^a$ representing an alkali metal, a hydrogen atom or an alkyl group, or alternatively is absent if another part of the molecule is cationic, and $R^{a'}$ representing a hydrogen atom or an alkyl group and t is equal to 1 or 2;
- an "optionally substituted saturated or unsaturated $C_1$-$C_{30}$ divalent hydrocarbon-based chain" represents a hydrocarbon-based chain, which is particularly a $C_1$-$C_8$ chain, optionally comprising one or more conjugated or unconjugated π double bonds, the hydrocarbon-based chain particularly being saturated; the said chain is optionally substituted with one or more identical or different groups chosen from hydroxyl, ($C_1$-$C_2$)alkoxy, (poly)hydroxy($C_2$-$C_4$)alkoxy, (di)($C_1$-$C_2$)(alkyl)amino, $R^a$—$Z^a$—$C(Z^b)$—, and $R^a$—$Z^a$—$S(O)_t$— with $Z^a$, $Z^b$, which may be identical or different, representing an oxygen or sulfur atom, or a group $NR^{a'}$, $R^a$ representing an alkali metal, a hydrogen atom or an alkyl group, or alternatively is absent if another part of the molecule is cationic, and $R^{a'}$ representing a hydrogen atom or an alkyl group and t is equal to 1 or 2;
- the "aryl" or "heteroaryl" radicals or the aryl or heteroaryl part of a radical may be substituted with at least one substituent borne by a carbon atom, chosen from:
  - a $C_1$-$C_{16}$ and preferably $C_1$-$C_8$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;
  - a halogen atom;
  - a hydroxyl group;
  - a $C_1$-$C_2$ alkoxy radical;
  - a $C_2$-$C_4$ (poly)hydroxyalkoxy radical;
  - an amino radical;
  - a 5- or 6-membered heterocycloalkyl radical;
  - an optionally cationic 5- or 6-membered heteroaryl radical, preferentially imidazolium, optionally substituted with a ($C_1$-$C_4$)alkyl radical, preferentially methyl;
  - an amino radical substituted with one or two identical or different $C_1$-$C_6$ alkyl radicals, optionally bearing at least:

i) a hydroxyl group,
ii) an amino group optionally substituted with one or two optionally substituted $C_1$-$C_3$ alkyl radicals, said alkyl radicals possibly forming with the nitrogen atom to which they are attached a saturated or unsaturated, optionally substituted 5- to 7-membered heterocycle, optionally comprising at least one other nitrogen or non-nitrogen heteroatom,
iii) a quaternary ammonium group —$N^+R'R''R'''$, $M^-$ for which R', R'' and R''', which may be identical or different, represent a hydrogen atom or a $C_1$-$C_4$ alkyl group; and $M^-$ represents the counterion of the organic or mineral acid or of the corresponding halide;
iv) or an optionally cationic 5- or 6-membered heteroaryl radical, preferentially imidazolium, optionally substituted with a ($C_1$-$C_4$)alkyl radical, preferentially methyl;

an acylamino radical (—NR—C(O)—R') in which the radical R is a hydrogen atom, a $C_1$-$C_4$ alkyl radical optionally bearing at least one hydroxyl group and the radical R' is a $C_1$-$C_2$ alkyl radical; a carbamoyl radical (($R)_2$N—C(O)—) in which the radicals R, which may be identical or different, represent a hydrogen atom, a $C_1$-$C_4$ alkyl radical optionally bearing at least one hydroxyl group; an alkylsulfonylamino radical (R'—S(O)$_2$—N(R)—) in which the radical R represents a hydrogen atom, a $C_1$-$C_4$ alkyl radical optionally bearing at least one hydroxyl group and the radical R' represents a $C_1$-$C_4$ alkyl radical or a phenyl radical; an aminosulfonyl radical (($R)_2$N—S(O)$_2$—) in which the radicals R, which may be identical or different, represent a hydrogen atom or a $C_1$-$C_4$ alkyl radical optionally bearing at least one hydroxyl group,
a carboxylic radical in acid or salified form (preferably with an alkali metal or a substituted or unsubstituted ammonium);
a cyano group;
a nitro or nitroso group;
a polyhaloalkyl group, preferentially trifluoromethyl; the cyclic or heterocyclic part of a non-aromatic radical may be substituted with at least one substituent chosen from the following groups:
hydroxyl,
$C_1$-$C_4$ alkoxy or $C_2$-$C_4$ (poly)hydroxyalkoxy;
$C_1$-$C_4$ alkyl;
alkylcarbonylamino (R—C(O)—NR'—) in which the radical R' is a hydrogen atom or a $C_1$-$C_4$ alkyl radical optionally bearing at least one hydroxyl group, and the radical R is a $C_1$-$C_2$ alkyl radical or an amino radical optionally substituted with two $C_1$-$C_4$ alkyl groups, which may be identical or different, optionally bearing at least one hydroxyl group, the said alkyl radicals possibly forming, with the nitrogen atom to which they are attached a saturated or unsaturated, optionally substituted 5- to 7-membered heterocycle optionally comprising at least one other nitrogen or non-nitrogen heteroatom;
alkylcarbonyloxy (R—C(O)—O—) in which the radical R is a $C_1$-$C_4$ alkyl radical or an amino group optionally substituted with one or two identical or different $C_1$-$C_4$ alkyl groups optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;
alkoxycarbonyl (R-G-C(O)—) in which the radical R is a $C_1$-$C_4$ alkoxy radical, G is an oxygen atom or an amino group optionally substituted with a $C_1$-$C_4$ alkyl group optionally bearing at least one hydroxyl group, the said alkyl radical possibly forming with the nitrogen atom to which they are attached a saturated or unsaturated, optionally substituted 5- to 7-membered heterocycle, optionally comprising at least one other nitrogen or non-nitrogen heteroatom;
a cyclic or heterocyclic radical, or a non-aromatic portion of an aryl or heteroaryl radical, may also be substituted with one or more oxo groups;
a hydrocarbon-based chain is unsaturated when it comprises one or more double bonds and/or one or more triple bonds;
an "aryl" radical represents a fused or non-fused monocyclic or polycyclic carbon-based group containing from 6 to 22 carbon atoms, and in which at least one ring is aromatic; preferentially, the aryl radical is a phenyl, biphenyl, naphthyl, indenyl, anthracenyl or tetrahydronaphthyl;
a "heteroaryl radical" represents a fused or non-fused, optionally cationic, 5- to 22-membered monocyclic or polycyclic group, comprising from 1 to 6 heteroatoms chosen from nitrogen, oxygen, sulfur and selenium, and at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthyl and the ammonium salt thereof;
a "cyclic radical" is a non-aromatic, monocyclic or polycyclic, fused or non-fused cycloalkyl radical, containing from 5 to 22 carbon atoms, which may comprise one or more unsaturations;
a "heterocyclic radical" or "heterocycle" is a fused or non-fused, 5- to 22-membered monocyclic or polycyclic non-aromatic radical, comprising from 1 to 6 heteroatoms chosen from nitrogen, oxygen, sulfur and selenium;
a "heterocycloalkyl radical" is a saturated heterocyclic radical;
a "cationic heteroaryl radical" is a heteroaryl group as defined previously, which comprises an endocyclic or exocyclic cationic group,
when the charge is endocyclic, it is included in the electron delocalization via the mesomeric effect, for example it is a pyridinium, imidazolium or indolinium

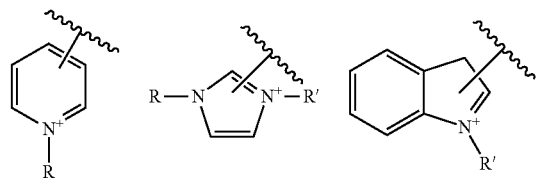

with R and R' being a heteroaryl substituent as defined previously and particularly a (hydroxy)($C_1$-$C_8$)alkyl group such as methyl;

when the charge is exocyclic, it is not included in the electron delocalization via the mesomeric effect, for example it is an ammonium or phosphonium substituent $R^+$ such as trimethylammonium, which is outside the heteroaryl such as pyridyl, indolyl, imidazolyl or naphthalimidyl in question;

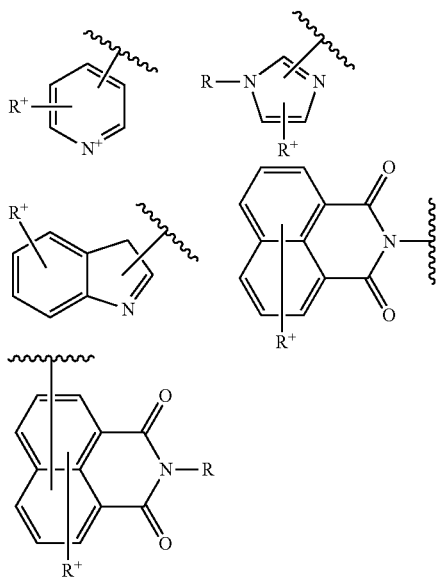

with R being a heteroaryl substituent as defined previously and $R^+$ an ammonium $R_aR_bR_cN^+$—, phosphonium $R_aR_bR_cP^+$— or ammonium $R_aR_bR_cN^+$—($C_1$-$C_6$)alkylamino group with $R_a$, $R_b$ and $R_c$, which may be identical or different, representing a hydrogen atom or a group ($C_1$-$C_8$)alkyl such as methyl;

a "cationic aryl bearing an exocyclic charge" means an aryl ring whose cationic group is outside the said ring: it is especially an ammonium or phosphonium substituent $R^+$ such as trimethylammonium outside the aryl such as phenyl or naphthyl:

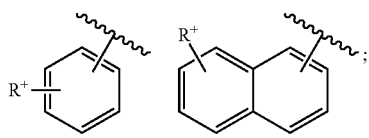

an "alkyl radical" is a linear or branched $C_1$-$C_{20}$ and preferably $C_1$-$C_8$ hydrocarbon-based radical;

an "alkenylene radical" is an alkyl radical as defined previously, which may contain from 1 to 4 conjugated or unconjugated double bonds —C=C—; the alkenylene group particularly contains 1 or 2 unsaturations;

the term "optionally substituted" applied to the alkyl radical implies that the said alkyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, the said alkyl radicals possibly forming with the nitrogen atom that bears them a 5- to 7-membered heterocycle optionally comprising another nitrogen or non-nitrogen heteroatom; v) or a quaternary ammonium group —$N^+R'R''R'''$, $M^-$ for which R', R" and R''', which may be identical or different, represent a hydrogen atom or a $C_1$-$C_4$ alkyl group, or alternatively —$N^+R'R''R'''$ forms a heteroaryl such as imidazolium optionally substituted with a $C_1$-$C_4$ alkyl group, and $M^-$ represents the counterion of the organic or mineral acid or of the corresponding halide;

an "alkoxy radical" is an alkyl-oxy or alkyl-O— radical for which the alkyl radical is a linear or branched $C_1$-$C_{16}$ and preferentially $C_1$-$C_8$ hydrocarbon-based radical;

when the alkoxy group is optionally substituted, this implies that the alkyl group is optionally substituted as defined hereinabove;

the "tone depth" is the unit known to hairstyling professionals, published in the book *Sciences des traitements capillaires* [Hair treatment sciences] by Charles Zviak, 1988, published by Masson, pp. 215 and 278; the tone depths range from 1 (black) to 10 (very light blond), one unit corresponding to one tone; the higher the figure, the lighter the shade;

a "dark" keratin fibre is a keratin fibre whose lightness $L^*$ measured in the CIEL $L^*a^*b^*$ system is less than or equal to 45 and preferably less than or equal to 40, given that $L^*=0$ is equivalent to black and $L^*=100$ is equivalent to white;

"naturally or artificially dark hair" means hair whose tone depth is less than or equal to 6 (dark blond) and preferably less than or equal to 4 (chestnut-brown). Artificially dyed hair is hair whose colour has been modified by a coloration treatment, for example a coloration with direct dyes or oxidation dyes.

The expression "at least one" means "one or more".

1.1. Direct Dyes Bearing a Disulfide or Thiol Function of the Invention:

According to one preferred mode of the invention, the direct dye(s) bearing a disulfide, thiol or protected thiol function used in the invention is/are of formula (I) as defined previously.

One particular mode of the invention concerns the dyes bearing a disulfide function of formula (I) as defined previously, i.e. for which U represents the following radical $$-S-C'_{sat}-(X')_{p'}-A'.\qquad\text{a)}$$

According to another particular mode, the invention concerns the dyes of formula (I) bearing a thiol function as defined previously, i.e. U representing the radical b) Y.

Another particular embodiment of the invention relates to fluorescent dyes bearing a disulfide, thiol or protected thiol function, for dyeing and/or lightening dark keratin fibres.

More particularly, the fluorescent dyes bear a disulfide function.

1.1.1. Y:

According to one particular embodiment of the invention, the cationic direct dye of formula (I) is a thiol dye, i.e. Y represents i) a hydrogen atom.

In accordance with another particular embodiment of the invention, in the abovementioned formula (I), Y is a protecting group known to those skilled in the art, for instance those described in the publications "*Protective Groups in Organic Synthesis*", T. W. Greene, published by John Wiley & Sons, NY, 1981, pp. 193-217; "Protecting Groups", P. Kocienski, Thieme, 3rd edition, 2005, chapter 5, and Ullmann's Encyclopedia, "*Peptide Synthesis*", pp. 4-5, 2005 Wiley-VCH Verlag GmbH & Co. KGaA, Weinheim 10.1002/14356007.a19 157;

In particular, Y represents a thiol-function protecting group chosen from the following radicals:
- $(C_1-C_4)$alkylcarbonyl;
- $(C_1-C_4)$alkylthiocarbonyl;
- $(C_1-C_4)$alkoxycarbonyl;
- $(C_1-C_4)$alkoxythiocarbonyl;
- $(C_1-C_4)$alkylthio-thiocarbonyl;
- $(di)(C_1-C_4)$(alkyl)aminocarbonyl;
- $(di)(C_1-C_4)$(alkyl)aminothiocarbonyl;
- arylcarbonyl, for instance phenylcarbonyl;
- aryloxycarbonyl;
- aryl$(C_1-C_4)$alkoxycarbonyl;
- $(di)(C_1-C_4)$(alkyl)aminocarbonyl for instance dimethylaminocarbonyl;
- $(C_1-C_4)$(alkyl)arylaminocarbonyl;
- carboxyl;
- $SO_3^-$; $M^+$ with $M^+$ representing an alkali metal such as sodium or potassium, or alternatively a counterion of the cationic chromophore A and $M^+$ are absent;
- optionally substituted aryl such as phenyl, dibenzosuberyl or 1,3,5-cycloheptatrienyl;
  - optionally substituted heteroaryl; especially including the following cationic or non-cationic heteroaryl radicals comprising from 1 to 4 heteroatoms:
    - i) 5-, 6- or 7-membered monocyclic radicals such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl, imidazolium;
    - ii) 8- to 11-membered bicyclic radicals such as indolyl, indolinium, benzimidazolyl, benzimidazolium, benzoxazolyl, benzoxazolium, dihydrobenzoxazolinyl, benzothiazolyl, benzothiazolium, pyridoimidazolyl, pyridoimidazolium, thienocycloheptadienyl, these monocyclic or bicyclic groups being optionally substituted with one or more groups such as $(C_1-C_4)$alkyl, for instance methyl, or polyhalo$(C_1-C_4)$alkyl, for instance trifluoromethyl;
    - iii) or the following tricyclic ABC radical:

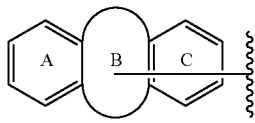

in which the two rings A and C optionally comprise a heteroatom, and ring B is a 5-, 6- or 7-membered ring, particularly a 6-membered ring, and contains at least one heteroatom, for instance piperidyl or pyranyl;
- optionally cationic, optionally substituted heterocycloalkyl, the heterocycloalkyl group especially represents a saturated or partially saturated 5-, 6- or 7-membered monocyclic group comprising from 1 to 4 heteroatoms chosen from oxygen, sulfur and nitrogen, such as di/tetrahydrofuryl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidyl, morpholinyl, di/tetra/hexahydroazepinyl, di/tetrahydropyrimidinyl, these groups being optionally substituted with one or more groups such as $(C_1-C_4)$ alkyl, oxo or thioxo; or the heterocycle represents the following group:

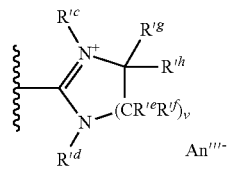

in which $R^{\prime c}$, $R^{\prime d}$, $R^{\prime e}$, $R^{\prime f}$, $R^{\prime g}$ and $R^{\prime h}$, which may be identical or different, represent a hydrogen atom or a $(C_1-C_4)$ alkyl group, or alternatively two groups $R^{\prime g}$ with $R^{\prime h}$, and/or $R^{\prime e}$ with $R^{\prime f}$, form an oxo or thioxo group, or alternatively $R^{\prime g}$ with $R^{\prime e}$ together form a cycloalkyl; and v represents an integer between 1 and 3 inclusive; preferentially, $R^{\prime c}$ to $R^{\prime h}$ represent a hydrogen atom; and $An^{\prime\prime\prime-}$ represents a counterion;
- $-C(NR^{\prime c}R^{\prime d})=N^+R^{\prime e}R^{\prime f}$; $An^{\prime\prime\prime-}$ with $R^{\prime c}$, $R^{\prime d}$, $R^{\prime e}$ and $R^{\prime f}$, which may be identical or different, representing a hydrogen atom or a $(C_1-C_4)$alkyl group; preferentially, $R^{\prime c}$ to $R^{\prime f}$ represent a hydrogen atom; and $An^{\prime\prime\prime-}$ represents a counterion;
- $-C(NR^{\prime c}R^{\prime d})=NR^{\prime e}$; with $R^{\prime c}$, $R^{\prime d}$ and $R^{\prime e}$ as defined previously;
- optionally substituted (di)aryl$(C_1-C_4)$alkyl such as 9-anthracenylmethyl, phenylmethyl or diphenylmethyl optionally substituted with one or more groups especially chosen from $(C_1-C_4)$ alkyl, $(C_1-C_4)$ alkoxy such as methoxy, hydroxyl, alkylcarbonyl or $(di)(C_1-C_4)$(alkyl)amino such as dimethylamino;
- optionally substituted (di)heteroaryl$(C_1-C_4)$alkyl, the heteroaryl group especially being a cationic or non-cationic, 5- or 6-membered monocyclic radical comprising from 1 to 4 heteroatoms chosen from nitrogen, oxygen and sulfur, such as pyrrolyl, furanyl, thiophenyl, pyridyl, pyridyl N-oxide such as 4-pyridyl or 2-pyridyl-N-oxide, pyrylium, pyridinium or triazinyl groups, optionally substituted with one or more groups such as alkyl, particularly methyl; advantageously, the (di)heteroaryl$(C_1-C_4)$alkyl is (di)heteroarylmethyl or (di)heteroarylethyl;
- $CR^1R^2R^3$ with $R^1$, $R^2$ and $R^3$, which may be identical or different, representing a halogen atom or a group chosen from:
  - $(C_1-C_4)$alkyl;
  - $(C_1-C_4)$alkoxy;
  - optionally substituted aryl such as phenyl optionally substituted with one or more groups, for instance $(C_1-C_4)$alkyl, $(C_1-C_4)$alkoxy or hydroxyl;
  - optionally substituted heteroaryl such as thiophenyl, furanyl, pyrrolyl, pyranyl or pyridyl, optionally substituted with a $(C_1-C_4)$alkyl group;
- $P(Z^1)R^{\prime 1}R^{\prime 2}R^{\prime 3}$ with $R^{\prime 1}$ and $R^{\prime 2}$, which may be identical or different, representing a hydroxyl, $(C_1-C_4)$ alkoxy or alkyl group, $R^{\prime 3}$ representing a hydroxyl or $(C_1-C_4)$alkoxy group, and $Z^1$ representing an oxygen or sulfur atom;

a sterically hindered ring; and optionally substituted alkoxyalkyl, such as methoxymethyl (MOM), ethoxyethyl (EOM) and isobutoxymethyl.

According to one particular embodiment, the thiol-protected dyes of formula (I) comprise a group Y chosen from i) aromatic cationic 5- or 6-membered monocyclic heteroaryl comprising from 1 to 4 heteroatoms chosen from oxygen, sulfur and nitrogen, such as oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinyl, pyrazinium, pyridazinium, triazinium, tetrazinium, oxazepinium, thiepinyl, thiepinium, imidazolium; ii) cationic 8- to 11-membered bicyclic heteroaryl such as indolinium, benzimidazolium, benzoxazolium, benzothiazolium, these monocyclic or bicyclic heteroaryl groups optionally being substituted with one or more groups such as alkyls, for instance methyl, or polyhalo($C_1$-$C_4$)alkyl such as trifluoromethyl; iii) or the following heterocyclic:

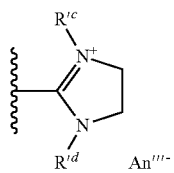

in which $R'^c$ and $R'^d$, which may be identical or different, represent a hydrogen atom or a group ($C_1$-$C_4$)alkyl; preferentially $R'^c$ to $R'^d$ represent a group ($C_1$-$C_4$)alkyl such as methyl; and An''' represents a counterion.

In particular, Y represents a group chosen from oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinium, pyridazinium, triazinium and imidazolium, benzimidazolium, benzoxazolium, benzothiazolium, these groups being optionally substituted with one or more ($C_1$-$C_4$)alkyl groups, especially methyl.

In particular, Y represents a protecting group such as:

($C_1$-$C_4$)alkylcarbonyl, for instance methylcarbonyl or ethylcarbonyl;

arylcarbonyl, for instance phenylcarbonyl;

($C_1$-$C_4$)alkoxycarbonyl;

aryloxycarbonyl;

aryl($C_1$-$C_4$)alkoxycarbonyl;

(di)($C_1$-$C_4$)(alkyl)aminocarbonyl, for instance dimethylaminocarbonyl;

($C_1$-$C_4$)(alkyl)arylaminocarbonyl;

optionally substituted aryl such as phenyl;

5- or 6-membered monocyclic heteroaryl such as imidazolyl or pyridyl;

cationic 5- or 6-membered monocyclic heteroaryl such as pyrylium, pyridinium, pyrimidinium, pyrazinium, pyridazinium, triazinium, imidazolium; these groups being optionally substituted with one or more identical or different ($C_1$-$C_4$)alkyl groups such as methyl;

cationic 8- to 11-membered bicyclic heteroaryl such as benzimidazolium or benzoxazolium; these groups being optionally substituted with one or more identical or different ($C_1$-$C_4$)alkyl groups such as methyl;

cationic heterocycle having the following formula:

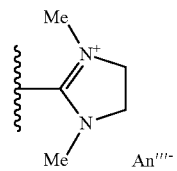

—C(NH$_2$)=N$^+$H$_2^-$; An''''$^-$; with An''''$^-$ being an anionic counterion as defined previously;

—C(NH$_2$)=NH;

SO$_3^-$, M$^+$ with M$^+$ representing an alkali metal such as sodium or potassium.

1.1.2. $C_{sat}$ and $C'_{sat}$

As indicated previously, in formula (I), $C_{sat}$ and $C'_{sat}$, independently of each other, represent a linear or branched, optionally substituted, optionally cyclic $C_1$-$C_{18}$ alkylene chain.

Substituents that may be mentioned include amino groups, ($C_1$-$C_4$)alkylamino groups, ($C_1$-$C_4$)dialkyl amino groups, or the group $R^a$—$Z^a$—C($Z^b$)— (in which $Z^a$, $Z^b$, which may be identical or different, represent an oxygen or sulfur atom or a group NR$^{a_1}$, and $R^a$ represents an alkali metal, a hydrogen atom or a $C_1$-$C_4$ alkyl group and $R^{a_1}$ represents a hydrogen atom or a $C_1$-$C_4$ alkyl group) preferably present on the carbon in the beta or gamma position relative to the sulfur atoms.

Preferably, in the case of formula (I), $C_{sat}$ and $C'_{sat}$ represent a chain —(CH$_2$)$_k$— with k being an integer between 1 and 8 inclusive.

1.1.3. X and X':

In accordance with one particular embodiment of the invention, in the abovementioned formula (I), when p and p' is equal to 1, the radicals X and X', which may be identical or different, represent the following sequence:

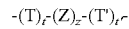

the said sequence being linked in formula (I) symmetrically as follows:

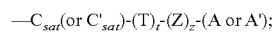

in which:

T and T', which may be identical or different, represent one or more radicals or combinations thereof chosen from: —O—; —S—; —N(R)—; —N$^+$(R)(R$^o$)—; —S(O)—; —S(O)$_2$—; —C(O)—; with R, R$^o$, which may be identical or different, representing a hydrogen atom, a $C_1$-$C_4$ alkyl radical, $C_1$-$C_4$ hydroxyalkyl radical or an aryl($C_1$-$C_4$)alkyl radical; and a cationic or non-cationic, preferentially monocyclic heterocycloalkyl or heteroaryl radical, preferentially containing two heteroatoms (more preferentially two nitrogen atoms) and preferentially being 5- to 7-membered, more preferentially imidazolium;

the indices t and t', which may be identical or different, are equal to 0 or 1;

Z represents:

—(CH$_2$)$_m$— radical with m being an integer between 1 and 8;

—(CH$_2$CH$_2$O)$_q$— or —(OCH$_2$CH$_2$)$_q$— in which q is an integer between 1 and 5 inclusive;

an aryl, alkylaryl or arylalkyl radical in which the alkyl radical is $C_1$-$C_4$ and the aryl radical is preferably $C_6$, being optionally substituted with at least one group SO$_3$M with M representing a hydrogen atom, an alkali metal or an ammonium group substituted with one or more identical or different, linear or branched $C_1$-$C_{18}$ alkyl radicals optionally bearing at least one hydroxyl;

z is 0 or 1.

Moreover, according to one particular embodiment of the invention, Z represents:

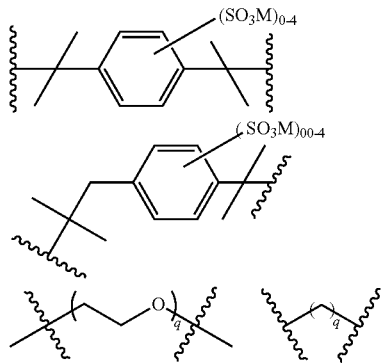

in which M represents a hydrogen atom, an alkali metal or an ammonium group or an ammonium group substituted with one or more identical or different, linear or branched $C_1$-$C_{10}$ alkyl radicals optionally bearing at least one hydroxyl; 0-4 represents an integer between 0 and 4 inclusive, and q represents an integer between 1 and 6.

1.1.4. A and A':

The radicals A and/or A' of formula (I) contain at least one cationic chromophore.

According to one preferred embodiment of the invention, the dyes (I) according to the invention are disulfides and comprise identical or cationic chromophores A and A'.

More particularly, the dyes of formula (I) according to the invention are symmetrical disulfides, i.e. they contain a C2 axis of symmetry, i.e. formula (I) is such that:

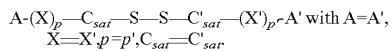

As cationic chromophores that are useful, mention may be made of those derived from the following dyes: acridines; acridones; anthrapyrimidines; anthranthrones; anthrapyrimidines; anthraquinones; azines; (poly)azos, hydrazono or hydrazones, in particular arylhydrazones; azomethines; benzanthrones; benzimidazoles; benzimidazolones; benzindoles; benzoxazoles; benzopyrans; benzothiazoles; benzoquinones; bisazines; bis-isoindolines; carboxanilides; coumarins; cyanins such as azacarbocyanins, diazacarbocyanins, diazahemicyanins, hemicyanin, or tetraazacarbocyanins; diazines; diketopyrrolopyrroles; dioxazines; diphenylamines; diphenylmethanes; dithiazines; flavonoids such as flavanthrones and flavones; fluorindines; formazans; indamines; indanthrones; indigoids and pseudo-indigoids; indophenols; indoanilines; isoindolines; isoindolinones; isoviolanthrones; lactones; (poly)methines such as dimethines of stilbene or styryl type; naphthalimides; naphthanilides; naphtholactams; naphthoquinones; nitro, especially nitro (hetero)aromatics; oxadiazoles; oxazines; perilones; perinones; perylenes; phenazines; phenoxazine; phenothiazines; phthalocyanin; polyenes/carotenoids; porphyrins; pyranthrones; pyrazolanthrones; pyrazolones; pyrimidinoanthrones; pyronines; quinacridones; quinolines; quinophthalones; squaranes; tetrazoliums; thiazines, thioindigo; thiopyronines; triarylmethanes, or xanthenes.

Among the cationic azo chromophores, mention may be made particularly of those derived from the cationic dyes described in the *Kirk Othmer Encyclopedia of Chemical Technology*, "Dyes, Azo", J. Wiley & Sons, updated on Apr. 19, 2010.

Among the cationic azo chromophores A and/or A' which can be used according to the invention, mention may be made of the cationic azo dyes described in patent applications WO 95/15144, WO-95/01772 and EP-714954.

According to one preferred embodiment of the invention, the coloured chromophore A and/or A' is chosen from cationic chromophores, preferentially those derived from dyes known as "basic dyes".

Among the azo chromophores, mention may be made of those described in the Colour Index International 3rd edition, and especially the following compounds:

Basic Red 22
Basic Red 76
Basic Yellow 57
Basic Brown 16
Basic Brown 17

Among the cationic quinone chromophores A and/or A', those mentioned in the abovementioned Colour Index International are suitable for use, and among those, mention may be made, inter alia, of the radicals derived from the following dyes:

Basic Blue 22
Basic Blue 99

Among the cationic azine chromophores A and/or A', those listed in the Colour Index International are suitable for use, and among those, for example the radicals derived from the following dyes:

Basic Blue 17
Basic Red 2.

Among the cationic triarylmethane chromophores A and/or A' that may be used according to the invention, mention may be made, besides those listed in the Colour Index, of the radicals derived from the following dyes:

Basic Green 1
Basic Violet 3
Basic Violet 14
Basic Blue 7
Basic Blue 26.

Mention may also be made of the cationic chromophores derived from the dyes described in documents U.S. Pat. No. 5,888,252, EP 1 133 975, WO 03/029 359, EP 860 636, WO 95/01772, WO 95/15144 and EP 714 954. Mention may also be made of those listed in the encyclopaedia "The chemistry of synthetic dye" by K. Venkataraman, 1952, Academic press vol. 1 to 7, in Kirk Othmer's encyclopaedia "Chemical technology", in the chapter "Dyes and dye intermediates", 1993, Wiley and sons, and in various chapters of "Ullmann's encyclopedia of Industrial chemistry" 7th edition, Wiley and sons.

Preferably, the cationic chromophores A and/or A' are chosen from those derived from dyes of azo and hydrazono type.

According to one particular embodiment, the cationic radicals A and/or A' in formula (I) comprise at least one cationic azo chromophore derived from a dye described in EP 850 636, FR 2 788 433, EP 920 856, WO 99/48465, FR 2 757 385, EP 85/0637, EP 91/8053, WO 97/44004, FR 2 570 946, FR 2 285 851, DE 2 538 363, FR 2 189 006, FR 1 560 664, FR 1 540 423, FR 1 567 219, FR 1 516 943, FR 1 221 122, DE 4 220 388, DE 4 137 005, WO 01/66646, U.S. Pat. No. 5,708,151, WO 95/01772, WO 515 144, GB 1 195 386, U.S. Pat. No. 3,524,842, U.S. Pat. No. 5,879,413, EP 1 062 940, EP 1 133

976, GB 738 585, DE 2 527 638, FR 2 275 462, GB 1974-27645, Acta Histochem. (1978), 61(1), 48-52; Tsitologiya (1968), 10(3), 403-5; Zh. Obshch. Khim. (1970), 40(1), 195-202; Ann. Chim. (Rome) (1975), 65(5-6), 305-14; Journal of the Chinese Chemical Society (Taipei) (1998), 45(1), 209-211; Rev. Roum. Chim. (1988), 33(4), 377-83; Text. Res. J. (1984), 54(2), 105-7; Chim. Ind. (Milan) (1974), 56(9), 600-3; Khim. Tekhnol. (1979), 22(5), 548-53; Ger. Monatsh. Chem. (1975), 106(3), 643-8; MRL Bull. Res. Dev. (1992), 6(2), 21-7; Lihua Jianyan, Huaxue Fence (1993), 29(4), 233-4; Dyes Pigm. (1992), 19(1), 69-79; Dyes Pigm. (1989), 11(3), 163-72.

According to one variant, A and/or A' of formula (I) contain at least one cationic radical borne by, or included in, at least one of the chromophores.

Preferably, the cationic radical is a quaternary ammonium; more preferentially, the cationic charge is endocyclic.

These cationic radicals are, for example, a cationic radical:
  bearing an exocyclic (di/tri)($C_1$-$C_8$)alkylammonium charge, or
  bearing an endocyclic charge, such as the following cationic heteroaryl groups: acridinium, benzimidazolium, benzobistriazolium, benzopyrazolium, benzopyridazinium, benzoquinolium, benzothiazolium, benzotriazolium, benzoxazolium, bipyridinium, bis-tetrazolium, dihydrothiazolium, imidazopyridinium, imidazolium, indolium, isoquinolium, naphthoimidazolium, naphthoxazolium, naphthopyrazolium, oxadiazolium, oxazolium, oxazolopyridinium, oxonium, phenazinium, phenoxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

Mention may be made of the hydrazono cationic chromophores of formulae (II) and (III'), and the azo cationic chromophores (IV), (IV'), (V) and (V') below:

(*)-Het⁺-C($R^a$)=N—N($R^b$)—Ar,Q⁻     (II)

Q⁻,Het⁺-C($R^a$)=N—N($R^b$)—Ar'-(*),     (II')

(*)-Het⁺-N($R^a$)—N=C($R^b$)—Ar,Q⁻     (III)

Q⁻,Het⁺-N($R^a$)—N=C($R^b$)—Ar'-(*),     (III')

(*)-Het⁺-N=N—Ar,Q⁻     (IV)

Q⁻,Het⁺-N=N—Ar'-(*),     (IV')

(*)—Ar⁺—N=N—Ar'',Q⁻     (V)

Q⁻,Ar⁺—N=N—Ar''-(*)     (V')

formulae (II) to (V') with:
  Het⁺ representing a cationic heteroaryl radical, preferentially bearing an endocyclic cationic charge, such as imidazolium, indolium or pyridinium, optionally substituted, preferentially with one or more ($C_1$-$C_8$) alkyl groups such as methyl;
  Ar⁺ representing an aryl radical, such as phenyl or naphthyl, bearing an exocyclic cationic charge, preferentially ammonium, particularly tri($C_1$-$C_8$)alkylammonium such as trimethylammonium;
  Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;
  Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy;
  Ar'' is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;
  $R^a$ and $R^b$, which may be identical or different, represent a hydrogen atom or a group ($C_1$-$C_8$)alkyl, which is optionally substituted, preferentially with a hydroxyl group; or alternatively the substituent $R^a$ with a substituent of Het⁺ and/or $R^b$ with a substituent of Ar form, together with the atoms that bear them, a (hetero)cycloalkyl; particularly, $R^a$ and $R^b$ represent a hydrogen atom or a group ($C_1$-$C_4$) alkyl, which is optionally substituted with a hydroxyl group;
  Q⁻ represents an organic or mineral anionic counterion such as a halide or an alkyl sulfate;
  (*) represents the part of the chromophore linked to the rest of the molecule of formula (I).

In particular, mention may be made of the azo and hydrazono chromophores bearing an endocyclic cationic charge of formulae (II) to (IV') as defined previously, more particularly those of formulae (II) to (IV') derived from the dyes described in patent applications WO 95/15144, WO 95/01772 and EP-714954. Preferentially the following chromophores:

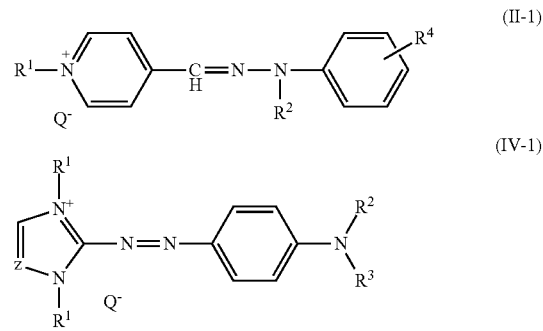

(II-1)

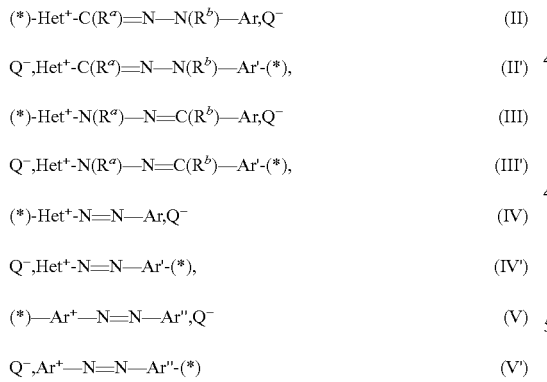

(IV-1)

formulae (III-1) and (IV-1) with:
  $R^1$ representing a group ($C_1$-$C_4$)alkyl such as methyl;
  $R^2$ and $R^3$, which may be identical or different, representing a hydrogen atom or a group ($C_1$-$C_4$)alkyl such as methyl; and
  $R^4$ representing a hydrogen atom or an electron-donating group such as optionally substituted ($C_1$-$C_8$)alkyl, optionally substituted ($C_1$-$C_8$)alkoxy, or (di)($C_1$-$C_8$) (alkyl)amino optionally substituted on the alkyl group(s) with a hydroxyl group; particularly, $R^4$ is a hydrogen atom,
  Z represents a group CH or a nitrogen atom, preferentially CH,
  Q⁻ is as defined previously;
it being understood that the chromophore (II-1) or (IV-1) is linked to the rest of the molecule of formula (I) by $R^2$, $R^1$ or $R^4$ in which case one of the hydrogen atoms of $R^2$, $R^1$ or $R^4$ is substituted with X or X' if p=1 or p'=1 or alternatively with $C_{sat}$ or $C_{sat'}$ if p=0 or p'=0.

Particularly, the chromophores (II-1) and (IV-1) are derived from Basic Red 51, Basic Yellow 87 and Basic Orange 31 or derivatives thereof:

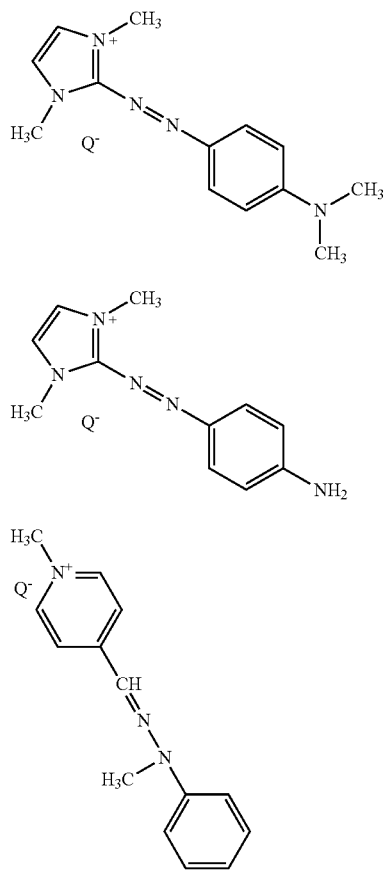

Basic Red 51

Basic Orange 31

Basic Yellow 87 with Q' being an anionic counterion as defined previously, particularly a halide such as chloride or an alkyl sulfate such as methyl sulfate or mesityl.

According to one particular embodiment of the invention, the dyes of formula (I) are fluorescent, i.e. they contain at least one fluorescent chromophore as defined previously.

As fluorescent chromophores A and/or A' that are useful in the present invention, mention may be made of radicals derived from the following dyes: acridines, acridones, benzanthrones, benzimidazoles, benzimidazolones, benzindoles, benzoxazoles, benzopyrans, benzothiazoles, coumarins, difluoro{2-[(2H-pyrrol-2-ylidene-kN)methyl]-1H-pyrrolato-kN}bores (BODIPY®), diketopyrrolopyrroles, fluorindines, (poly)methines (especially cyanins and styryls/hemicyanins), naphthalimides, naphthanilides, naphthylamine (such as dansyls), oxadiazoles, oxazines, perilones, perinones, perylenes, polyenes/carotenoids, squaranes, stilbenes and xanthenes.

Mention may also be made of the fluorescent dyes A and/or A' described in documents EP 1 133 975, WO 03/029 359, EP 860 636, WO 95/01772, WO 95/15144, EP 714 954 and those listed in the encyclopaedia "The chemistry of synthetic dye" by K. Venkataraman, 1952, Academic Press, vol. 1 to 7, in Kirk Othmer's encyclopaedia "Chemical Technology", in the chapter "Dyes and dye Intermediates", 1993, Wiley and Sons, and in various chapters of "Ullmann's Encyclopedia of Industrial Chemistry" 7th edition, Wiley and Sons, and in *The Handbook—A Guide to Fluorescent Probes and Labeling Technologies,* 10th Ed Molecular Probes/Invitrogen—Oregon 2005 circulated on the Internet or in the preceding printed editions.

According to one preferred variant of the invention, the cationic fluorescent chromophore A and/or A' comprises at least one quaternary ammonium radical such as those derived from the polymethine dyes of formulae (VI) and (VI') below:

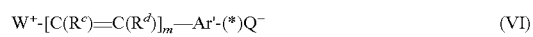  (VI)

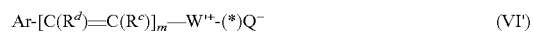  (VI')

formula (VI) or (VI') with:

$W^+$ representing a cationic heterocyclic or heteroaryl group, particularly comprising a quaternary ammonium optionally substituted with one or more groups $(C_1-C_8)$ alkyl optionally substituted especially with one or more hydroxyl groups;

$W'^+$ representing a divalent heterocyclic or heteroaryl radical as defined for $W^+$;

Ar representing an aryl group such as phenyl or naphthyl, optionally substituted preferentially with i) one or more halogen atoms such as chlorine or fluorine; ii) one or more groups $(C_1-C_8)$alkyl, preferably of $C_1-C_4$ such as methyl; iii) one or more hydroxyl groups; iv) one or more $(C_1-C_8)$alkoxy groups such as methoxy; v) one or more hydroxy$(C_1-C_8)$alkyl groups such as hydroxyethyl, vi) one or more amino groups or (di)$(C_1-C_8)$alkylamino, preferably with the $C_1-C_4$ alkyl part optionally substituted with one or more hydroxyl groups, such as (di)hydroxyethylamino, vii) with one or more acylamino groups; viii) one or more heterocycloalkyl groups such as piperazinyl, piperidyl or 5- or 6-membered heteroaryl such as pyrrolidinyl, pyridyl and imidazolinyl;

Ar' is a divalent aryl radical as defined for Ar;

m' represents an integer between 1 and 4 inclusive, particularly m is 1 or 2; more preferentially 1;

$R^c$ and $R^d$, which may be identical or different, represent a hydrogen atom or an optionally substituted group $(C_1-C_8)$alkyl, preferentially of $C_1-C_4$, or alternatively $R^c$ contiguous with $W^+$ or $W'^+$ and/or $R^d$ contiguous with Ar or Ar' form, with the atoms that bear them, a (hetero) cycloalkyl, particularly $R^c$ is contiguous with $W^+$ or $W'^+$ and forms a (hetero)cycloalkyl such as cyclohexyl;

$Q^-$ is an organic or mineral anionic counterion as defined previously;

(*) represents the part of the chromophore linked to the rest of the molecule of formula (I).

According to another variant, the disulfide, thiol or protected-thiol dye is a cationic fluorescent dye comprising at least one quaternary ammonium radical and such that, in formula (I) with p and p' equal to 1 and A and/or A' representing a naphthalimidyl radical bearing an exocyclic cationic charge of formula (VII) or (VII'):

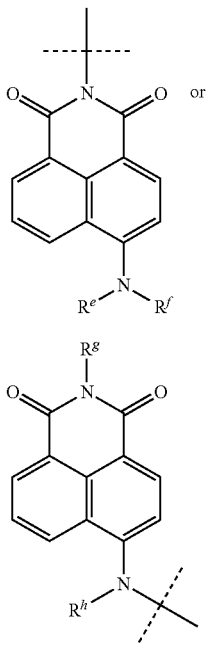

with †  representing the bond with the group X or X', $C_{sat}$ or $C'_{sat}$ in which formulae (VII) and (VII') $R^e$, $R^f$, $R^g$ and $R^h$, which may be identical or different, represent a hydrogen atom or a $C_1$-$C_6$ alkyl group which is optionally substituted, preferentially with a di($C_1$-$C_6$)alkylamino or tri($C_1$-$C_6$)alkylammonium group such as trimethylammonium.

According to one embodiment of the invention, p=1, z=t'=0, t=1 and T represents —N(R)—, preferably in the para position on Ar relative to the olefin function —C($R^c$)=C($R^d$)—.

Particularly, in one variant, p=1, z=t'=0, t=1 and T represents —N(R)—, preferably in the para position on Ar relative to the styryl function —C($R^c$)=C($R^d$)— and T' represents a group —N(R)— or —N$^+$(R)($R^o$)— or an imidazolium.

Preferably, $W^+$ or $W'^+$ is an imidazolium, pyridinium, benzimidazolium, pyrazolium, benzothiazolium or quinolinium optionally substituted with one or more identical or different $C_1$-$C_4$ alkyl radicals.

According to one particularly preferred embodiment of the invention, A and/or A' represent the chromophore (VI') as defined previously with m'=1, Ar representing a phenyl group substituted para to the styryl group —C($R^d$)=C($R^c$)— with a group (di)(hydroxy)($C_1$-$C_6$)(alkyl)amino such as dihydroxy ($C_1$-$C_4$)alkylamino, and representing an imidazolium or pyridinium group, preferentially ortho- or para-pyridinium.

As examples of dyes of the invention, mention may be made of the disulfide dyes chosen from formulae (VIII) to (XIV) and the thiol or protected-thiol dyes chosen from formulae (VIII') to (XIV') below:

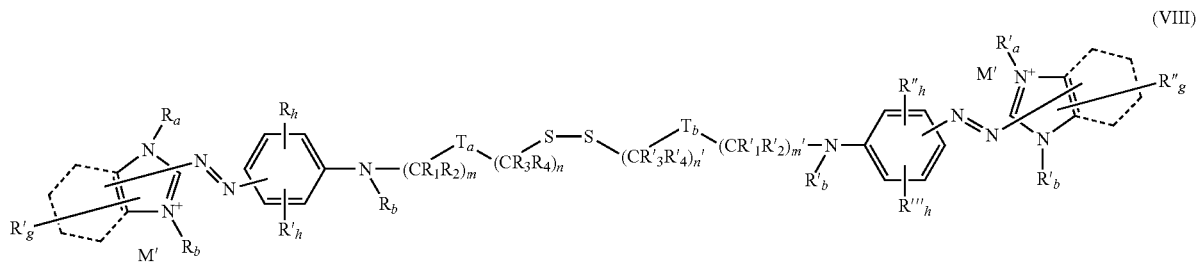
(VIII)

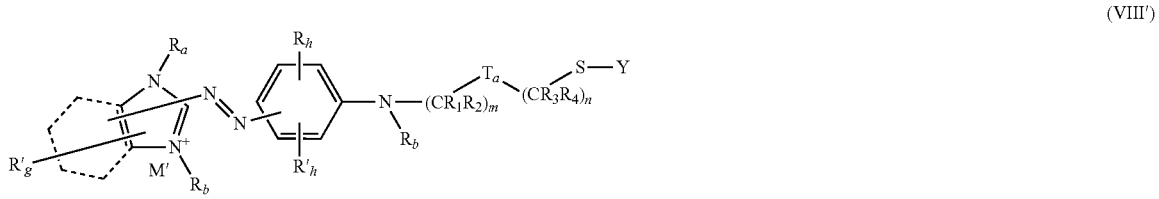
(VIII')

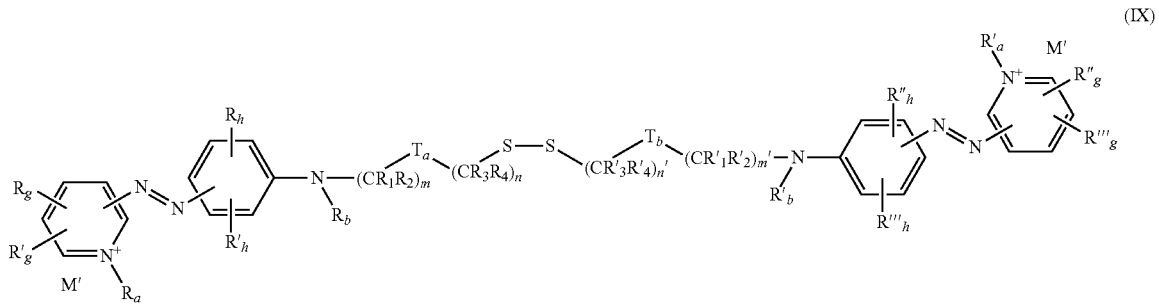
(IX)

-continued
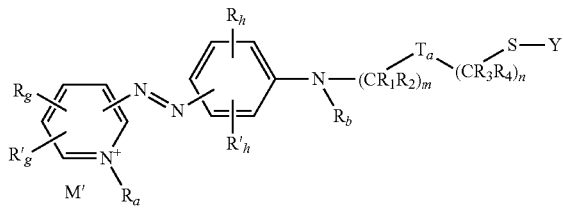
(IX')
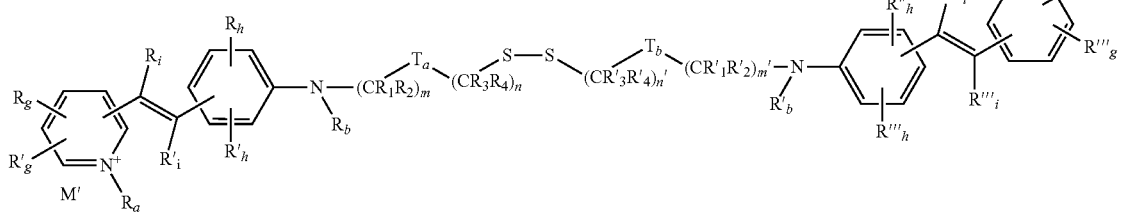
(X)
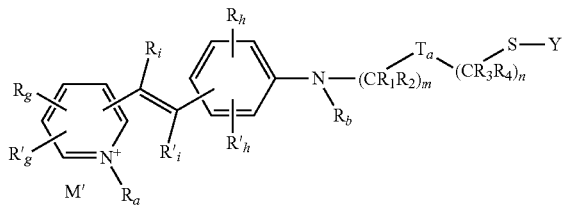
(X')
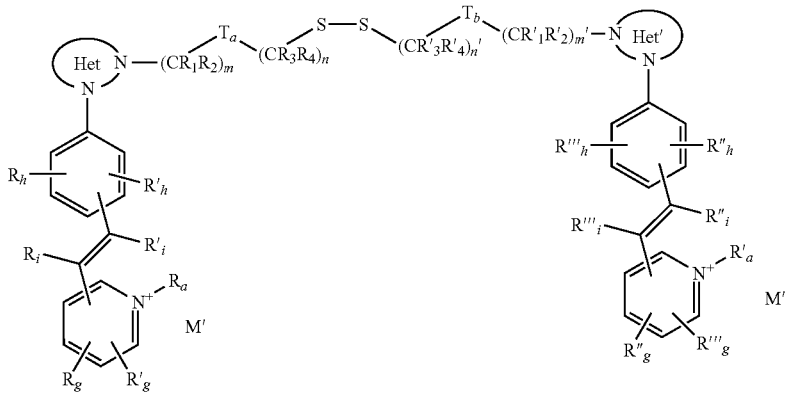
(XI)
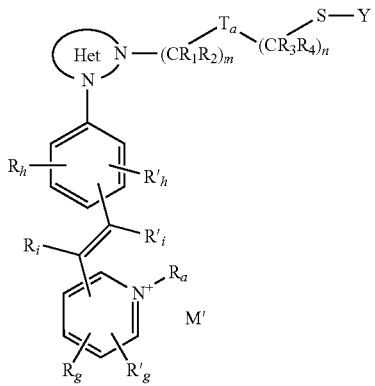
(XI')

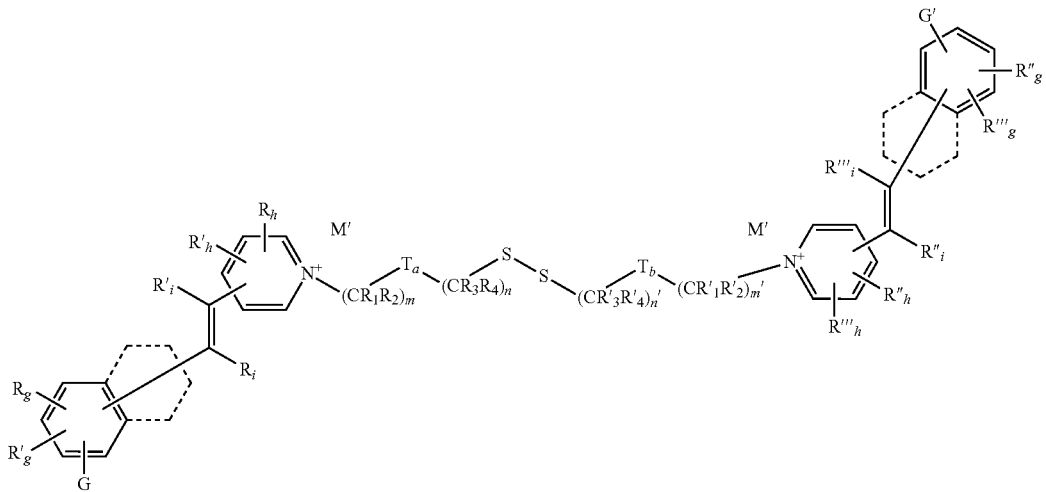
(XII)
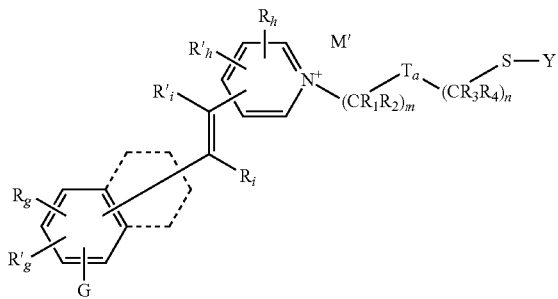
(XII')
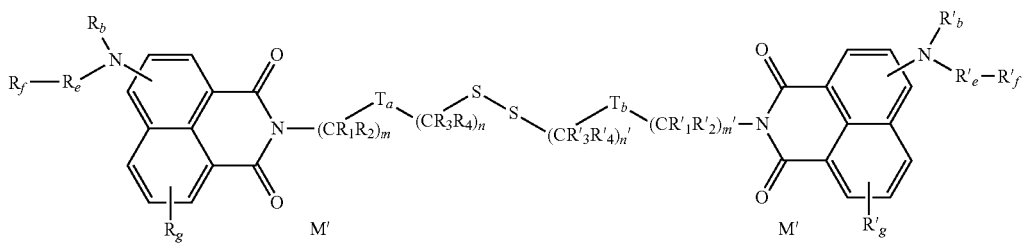
(XIII)
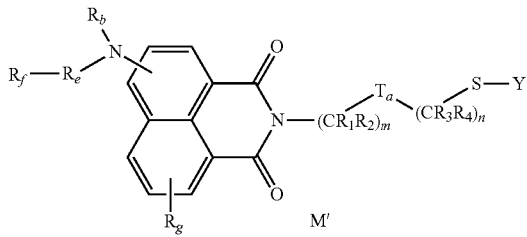
(XIII')
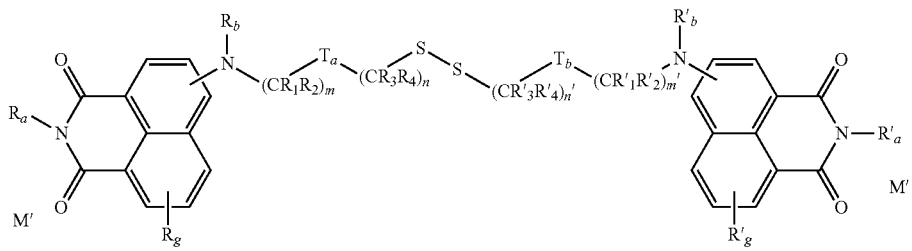
(XIV)

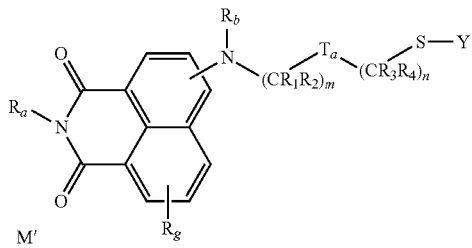

(XIV')

in which formulae (VIII) to (XIV) and (VIII') to (XIV'):
- G and G', which may be identical or different, represent a group —NR$_c$R$_d$, —NR'$_c$R'$_d$ or C$_1$-C$_6$ alkoxy which is optionally substituted, preferentially unsubstituted; preferentially, G and G' represent a group —NR$_c$R$_d$ or —NR'$_c$R'$_d$, respectively;
- R$^1$, R$^2$, R$^3$ and R$^4$, which may be identical or different, represent a hydrogen atom or a C$_1$-C$_6$ alkyl group; preferentially a hydrogen atom;
- R$_a$ and R'$_a$, which may be identical or different, represent an aryl(C$_1$-C$_4$)alkyl group or a C$_1$-C$_6$ alkyl group optionally substituted with a hydroxyl or amino, C$_1$-C$_4$ alkylamino or C$_1$-C$_4$ dialkyl amino group, the said alkyl radicals possibly forming, with the nitrogen atom that bears them, a 5- to 7-membered heterocycle, optionally comprising another nitrogen or non-nitrogen heteroatom; preferentially, R$_a$ and R'$_a$ represent a C$_1$-C$_3$ alkyl group optionally substituted with a hydroxyl group, or a benzyl group;
- R$_b$ and R'$_b$, which may be identical or different, represent a hydrogen atom, an aryl(C$_1$-C$_4$)alkyl group or a C$_1$-C$_6$ alkyl group that is optionally substituted; preferentially, R$_b$ and R'$_b$ represent a hydrogen atom or a C$_1$-C$_3$ alkyl or benzyl group;
- R$_c$, R'$_c$, R$_d$ and R'$_d$, which may be identical or different, represent a hydrogen atom, an aryl(C$_1$-C$_4$)alkyl or C$_1$-C$_6$ alkoxy group or a C$_1$-C$_6$ alkyl group that is optionally substituted; R$_c$, R'$_c$, R$_d$ and R'$_d$ preferentially represent a hydrogen atom, a hydroxyl, C$_1$-C$_3$ alkoxy, amino or C$_1$-C$_3$ (di)alkylamino group, or a C$_1$-C$_3$ alkyl group that is optionally substituted with i) a hydroxyl group, ii) amino, iii) C$_1$-C$_3$ (di)alkylamino, or iv) quaternary ammonium (R''')(R''')(R'''')N$^+$—;
- or alternatively two adjacent radicals R$_c$ and R$_d$, R'$_c$ and R'$_d$ borne by the same nitrogen atom together form a heterocyclic or heteroaryl group; preferentially, the heterocycle or heteroaryl is monocyclic and 5- to 7-membered; more preferentially, the groups are chosen from imidazolyl and pyrrolidinyl;
- R$_e$ and R'$_e$, which may be identical or different, represent a linear or branched, optionally unsaturated divalent C$_1$-C$_6$ alkylenyl hydrocarbon-based chain;
- R$_f$ and R'$_f$, which may be identical or different, represent a group di(C$_1$-C$_4$)alkylamino, (R'')(R''')N— or a quaternary ammonium group (R'')(R''')(R'''')N$^+$— in which R'', R''' and R'''', which may be identical or different, represent a hydrogen atom or a C$_1$-C$_4$ alkyl group or alternatively (R'')(R''')(R'''')N$^+$— represent an optionally substituted cationic heteroaryl group, preferentially an imidazolinium group optionally substituted with a C$_1$-C$_3$ alkyl group;
- R$_g$, R'$_g$, R''$_g$, R'''$_g$, R$_h$, R'$_h$, R''$_h$, and R'''$_h$, which may be identical or different, represent a hydrogen atom, a halogen atom, an amino, C$_1$-C$_4$ alkylamino, C$_1$-C$_4$ dialkylamino, cyano, carboxyl, hydroxyl or trifluoromethyl group, an acylamino, C$_1$-C$_4$ alkoxy, (poly)hydroxy(C$_2$-C$_4$)alkoxy, alkylcarbonyloxy, alkoxycarbonyl or alkylcarbonylamino radical, an acylamino, carbamoyl or alkylsulfonylamino radical, an aminosulfonyl radical, or a C$_1$-C$_{16}$ alkyl radical optionally substituted with a group chosen from C$_1$-C$_{12}$ alkoxy, hydroxyl, cyano, carboxyl, amino, C$_1$-C$_4$ alkylamino and C$_1$-C$_4$ dialkylamino, or alternatively two alkyl radicals borne by the nitrogen atom of the amino group form a 5- to 7-membered heterocycle optionally comprising another nitrogen or non-nitrogen heteroatom; preferentially, R$_g$, R'$_g$, R''$_g$, R∝''$_g$, R$_h$, R'$_h$, R''$_h$, and R'''$_h$ represent a hydrogen or halogen atom or a C$_1$-C$_3$ alkyl group;
- or alternatively two groups R$_g$ and R'$_g$, R''$_g$ and R'''$_g$, R$_h$, and R'$_h$; R''$_h$ and R'''$_h$ borne by two adjacent carbon atoms together form a benzo or indeno ring, a fused heterocycloalkyl or fused heteroaryl group; the benzo, indeno, heterocycloalkyl or heteroaryl ring being optionally substituted with a halogen atom, an amino, C$_1$-C$_4$ alkylamino, C$_1$-C$_4$ dialkylamino, nitro, cyano, carboxyl, hydroxyl or trifluoromethyl group, an acylamino, C$_1$-C$_4$ alkoxy, (poly) hydroxy(C$_2$-C$_4$)alkoxy, alkylcarbonyloxy, alkoxycarbonyl or alkylcarbonylamino radical, an acylamino, carbamoyl or alkylsulfonylamino radical, an aminosulfonyl radical, or a C$_1$-C$_{16}$ alkyl radical optionally substituted with: a group chosen from C$_1$-C$_{12}$ alkoxy, hydroxyl, cyano, carboxyl, amino, C$_1$-C$_4$ alkylamino, C$_1$-C$_4$ dialkylamino, or alternatively two alkyl radicals borne by the nitrogen atom of the amino group form a 5- to 7-membered heterocycle optionally comprising another nitrogen or non-nitrogen heteroatom; preferentially, R$_g$ and R'$_g$, R''$_g$ and R'''$_g$ together form a benzo group;
- or alternatively two groups R$_i$ and R$_g$, R'''$_i$ and R'''$_g$, R'$_i$ and R'$_h$; and/or R''$_i$ and R''$_h$ together form a fused (hetero)cycloalkyl, preferentially cycloalkyl such as cyclohexyl;
- or alternatively when G represents —NR$_c$R$_d$ and G' represents —NR'$_c$R'$_d$, two groups R$_c$ and R'$_g$; R'$_c$ and R''$_g$; R$_d$ and R$_g$, R'$_d$ and R'''$_g$ together form a saturated heteroaryl or heterocycle, optionally substituted with one or more groups (C$_1$-C$_6$)alkyl, preferentially a 5- to 7-membered heterocycle containing one or two heteroatoms chosen from nitrogen and oxygen; more preferentially the heterocycle is chosen from morpholinyl, piperazinyl, piperidyl and pyrrolidinyl groups;
- R$_i$, R'$_i$, R''$_i$, and R'''$_i$, which may be identical or different, represent a hydrogen atom or a C$_1$-C$_4$ alkyl group;
- R$_1$, R$_2$, R$_3$, R$_4$, R'$_1$, R'$_2$, R'$_3$, and R'$_4$, which may be identical or different, represent a hydrogen atom or a C$_1$-C$_4$ alkyl, C$_1$-C$_{12}$ alkoxy, hydroxyl, cyano, carboxyl, amino, C$_1$-C$_4$ alkylamino or C$_1$-C$_4$ dialkylamino group, the said alkyl radicals possibly forming with the nitrogen that bears them a 5- to 7-membered heterocycle optionally comprising another nitrogen or non-nitrogen heteroatom; preferentially, $R_1$, $R_2$, $R_3$, $R_4$, $R'_3$, and $R'_4$ are hydrogen atoms or an amino group; more preferentially, $R_1$, $R_2$, $R_3$, $R_4$, $R'_1$, $R'_2$, $R'_3$, and $R'_4$ represent a hydrogen atom;

$T_a$, $T_b$, which may be identical or different, represent i) either a covalent σ bond, ii) or one or more radicals or combinations thereof chosen from —$SO_2$—, —O—, —S—, —N(R)—, —$N^+(R)(R^\circ)$—, —CO—, with R, $R^\circ$, which may be identical or different, representing a hydrogen atom, a $C_1$-$C_4$ alkyl or $C_1$-$C_4$ hydroxyalkyl radical; or an aryl($C_1$-$C_4$)alkyl, preferentially, $T_a$ is identical to $T_b$ and represent a covalent σ bond or a group chosen from —N(R)—, —C(O)—N(R)—, —N(R)—C(O)—, —O—C(O)—, —C(O)—O— and —$N^+(R)(R^\circ)$—, with R, $R^\circ$, which may be identical or different, representing a hydrogen atom or a $C_1$-$C_4$ alkyl group; more preferentially, $T_a$ and $T_b$ represent a σ bond; iii) or a cationic or non-cationic, preferentially monocyclic, preferentially identical heterocycloalkyl or heteroaryl radical, preferentially containing two heteroatoms (more preferentially two nitrogen atoms) and preferentially being 5- to 7-membered, such as imidazolium;

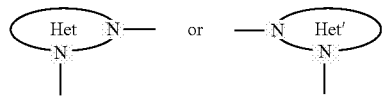

identical or different, represent an optionally substituted heterocyclic group; preferentially, the heterocycles are identical, monocyclic, saturated and 5- to 8-membered and comprise in total two nitrogen atoms;

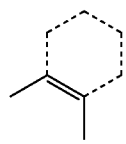

represent an aryl or heteroaryl group fused to the imidazolium or phenyl ring; or alternatively is absent from the imidazolium or phenyl ring; preferentially, when the ring is present, the ring is a benzo;

m, m', n and n', which may be identical or different, represent an integer between 0 and 6 inclusive, with m+n and m'+n', which may be identical or different, represents an integer between 1 and 10 inclusive; preferentially, m+n=m'+n'=an integer between 2 and 4 inclusive; more preferentially, m+n=m'+n'=an integer equal to 2;

Y is as defined previously; in particular, Y represents a hydrogen atom or a protecting group such as:
($C_1$-$C_4$)alkylcarbonyl, for instance methylcarbonyl or ethylcarbonyl;
arylcarbonyl, for instance phenylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl, for instance dimethylaminocarbonyl;
($C_1$-$C_4$)(alkyl)arylaminocarbonyl;
optionally substituted aryl such as phenyl;
5- or 6-membered monocyclic heteroaryl such as imidazolyl or pyridyl;
cationic 5- or 6-membered monocyclic heteroaryl such as pyrylium, pyridinium, pyrimidinium, pyrazinium, pyridazinium, triazinium, imidazolium; these groups being optionally substituted with one or more identical or different ($C_1$-$C_4$)alkyl groups such as methyl;
cationic 8- to 11-membered bicyclic heteroaryl such as benzimidazolium or benzoxazolium; these groups being optionally substituted with one or more identical or different ($C_1$-$C_4$)alkyl groups such as methyl;
cationic heterocycle having the following formula:

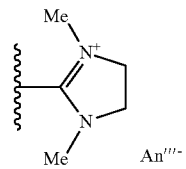 [SMILES: *C1=[N+](C)CCN1C]

—$C(NH_2)=N^+H_2$; $An'''^-$; with $An'''^-$ being an anionic counterion as defined previously;
—$C(NH_2)=NH$;
$SO_3^-$, $M^+$ with $M^+$ representing an alkali metal such as sodium or potassium. and
M' representing an anionic counterion, derived from a salt of an organic or mineral acid, or from an organic or mineral base that ensures the electrical neutrality of the molecule.

In particular, the dyes of formula (I) are chosen from dyes with a naphthalimidyl disulfide, thiol or protective-thiol chromophore, chosen from formulae (XIII), (XIII'), (XIV) and (XIV') as defined previously.

According to one preferred mode of the invention, the dyes of formula (I) are chosen from disulfide, thiol or protected-thiol dyes chosen from formulae (XV) to (XV') below:

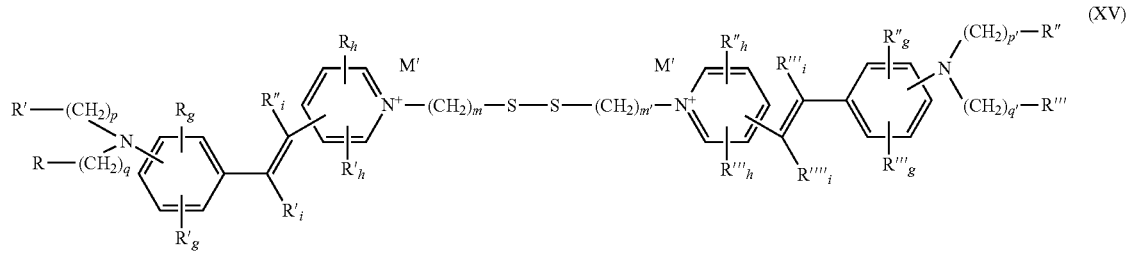

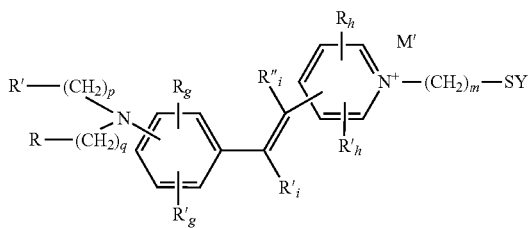

(XV')

the organic or mineral acid salts, optical isomers, geometrical isomers, and solvates such as hydrates thereof;
in which formulae (XV) and (XV'):

- R and R''', which may be identical or different, represent a hydroxyl group, an amino group ($NR_aR_b$) or an ammonium group ($N^+R_aR_bR_c$), $An^-$; preferentially hydroxyl; with $R_a$, $R_b$ and $R_c$, which may be identical or different, representing a hydrogen atom or a ($C_1$-$C_4$)alkyl group; or alternatively two alkyl groups $R_a$ and $R_b$ of the amino or ammonium group form a 5- to 7-membered heterocycle optionally comprising another nitrogen or non-nitrogen heteroatom, such as morpholinyl, piperazinyl, piperidyl, pyrrolyl, morpholinium, piperazinium, piperidinium or pyrrolinium, and $An^-$ representing an anionic counterion;
- R' and R'', which may be identical or different, represent a hydrogen atom or a group as defined for R and R''', respectively;
- $R_g$, $R'_g$, $R''_g$, $R'''_g$, $R_h$, $R'_h$, $R''_h$, and $R'''_h$, which may be identical or different, represent a hydrogen atom, a halogen atom, an amino, di($C_1$-$C_4$)alkylamino, cyano, carboxyl, hydroxyl or trifluoromethyl group, an acylamino, $C_1$-$C_4$ alkoxy, (poly)hydroxy($C_2$-$C_4$)alkoxy, ($C_1$-$C_4$)alkylcarbonyloxy, ($C_1$-$C_4$)alkoxycarbonyl, ($C_r$-$C_4$)alkylcarbonylamino, acylamino, carbamoyl or ($C_1$-$C_4$)alkylsulfonylamino radical, an aminosulfonyl radical, or a ($C_1$-$C_{16}$)alkyl radical optionally substituted with a group chosen from ($C_1$-$C_{12}$)alkoxy, hydroxyl, cyano, carboxyl, amino and di($C_1$-$C_4$)alkylamino, or alternatively the two alkyl radicals borne by the nitrogen atom of the amino group form a 5- to 7-membered heterocycle optionally comprising another nitrogen or non-nitrogen heteroatom; in particular, $R_g$, $R'_g$, $R''_g$, $R'''_g$, $R_h$, $R'_h$, $R''_h$, and $R'''_h$ represent a hydrogen or halogen atom or a ($C_1$-$C_4$)alkyl group;
- $R'_i$, $R''_i$, $R'''_i$ and $R''''_i$, which may be identical or different, represent a hydrogen atom or a ($C_1$-$C_4$)alkyl group; in particular $R'_i$, $R''_i$, $R'''_i$, and $R''''_i$ represent a hydrogen atom;
- m, m', which may be identical or different, represent an integer between 1 and 10 inclusive; in particular an integer between 2 and 4 inclusive; preferentially, m and m' are equal to 2;
- p, p', q and q', which may be identical or different, represent an integer between 1 and 6 inclusive;
- M' representing an anionic counterion; and
- Y is as defined previously;
- it being understood that when the compound of formula (XV) or (XV') contains other cationic parts, it is combined with one or more anionic counterions that afford formula (XV) or (XV') electrical neutrality.

According to one particular mode of the invention, the dyes of the invention belong to formula (XVa) or (XV'a) which bear an ethylene group connecting the pyridinium part to the phenyl ortho or para to the pyridinium, i.e. 2-4', 4-2', 4-4':

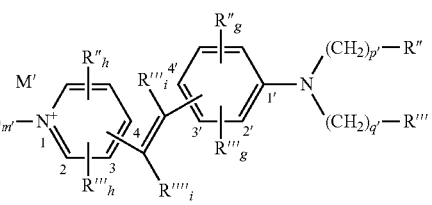

(XVa)

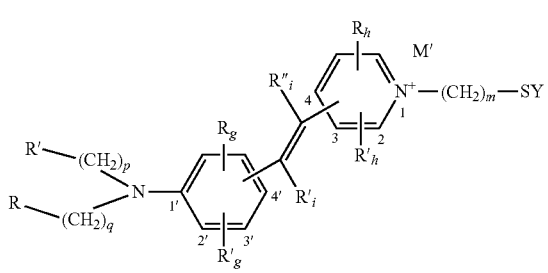

(XV'a)

with R, R', R", R'", $R_g$, $R'_g$, $R''_g$, $R'''_g$, $R_h$, $R'_h$, $R''_h$, $R'''_h$, $R'_i$, $R''_i$, $R'''_i$, $R''''_i$, m, m', p, p', q, q', Y and M' as defined previously in formulae (XV) and (XV'). In particular, $R_h$ and $R''_h$ are ortho to the pyridinium group and $R'_h$ and $R'''_h$ represent a hydrogen atom. Another aspect of the invention concerns the dyes of formula (XVa) or (XV'a) bearing groups $R_g$, $R''_g$ in position 3' and $R'_g/R'''_g$ which represent a hydrogen atom.

Advantageously, the dyes of formulae (XVa) and (XV'a) bear their ethylene group para to the phenyl bearing the amino group: $R'(CH_2)_p$—N—$(CH_2)_q$—R and/or $R'''(CH_2)_{p'}$—N—$(CH_2)_{q'}$—R''', i.e. in position 4', preferentially bear an ethylene or styryl group linking the pyridinium part to the phenyl ortho to the pyridinium, i.e. 2-4'.

According to another particular mode of the invention, the dyes of the invention belong to formula (XVI) or (XVI'):

hydroxy($C_1$-$C_4$)alkyl and/or —C(O)OR' group with R' representing a hydrogen atom, a $C_1$-$C_4$ alkyl group or a group —C(O)—$O^-$ and, in the latter case, an anionic counterion $An^-$ is absent; such as pyrrolidinyl and piperidyl;

$R_3$ represents a hydrogen atom or a group —C(O)OR" with R" representing a hydrogen atom, an alkali metal or a $C_1$-$C_6$ alkyl group or alternatively $R_3$ represents a group —C(O)—$O^-$ and, in the latter case, an anionic counterion $An^-$ is absent;

Z represents a divalent amido group —C(O)—N(R)—, —N(R)—C(O)—, or a divalent $C_1$-$C_{10}$ alkylene group interrupted with an amido group —C(O)—N(R)—, —N(R)—C(O)— such as —$(CH_2)_n$—C(O)—N(R)—$(CH_2)_p$—, —$(CH_2)_{n'}$—N(R)—C(O)—$(CH_2)_p$—, with

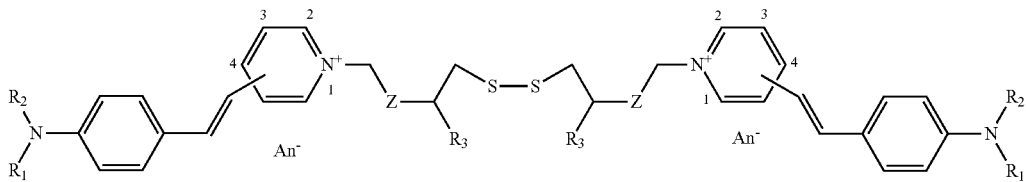

(XVI)

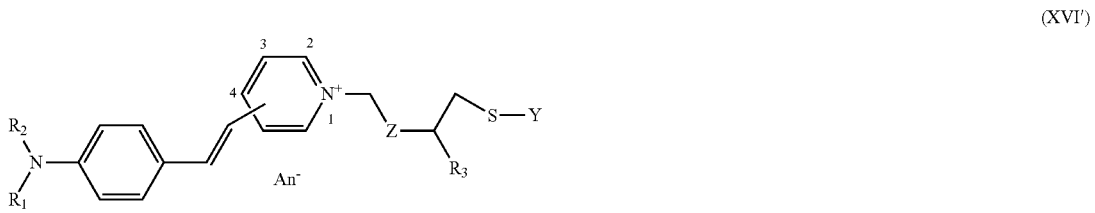

(XVI')

in which formula (XVI) or (XVI'):

$R_1$ represents a $C_1$-$C_6$ alkyl group substituted with one or more hydroxyl groups or —C(O)OR' with R' representing a hydrogen atom, a $C_1$-$C_4$ alkyl group or a group —C(O)—$O^-$ and, in the latter case, an anionic counterion $An^-$ is absent; in particular $R_1$ represents a $C_1$-$C_6$ alkyl group substituted with one or more hydroxyl groups and more specifically with only one hydroxyl group;

$R_2$ represents a $C_1$-$C_6$ alkyl group optionally substituted with one or more hydroxyl groups;

or alternatively the groups $R_1$ and $R_2$ form, together with the nitrogen atom that bears them, a saturated heterocyclic radical substituted with at least one hydroxyl, (poly)

n' representing an integer between 0 and 3 inclusive; preferentially, n' is equal to 0, 2, 3; p representing an integer between 0 and 4 inclusive, n" representing an integer between 0 and 3 inclusive and especially n'=n"=p=0 and R representing a hydrogen atom or a $C_1$-$C_6$ alkyl group;

$An^-$ represents an anionic counterion;

Y is as defined previously;

it being understood that when the compound of formula (XVI) or (XVI') contains other cationic parts, it is combined with one or more anionic counterions that afford formula (XVI) or (XVI') electrical neutrality.

According to another particular mode of the invention, the dyes of the invention belong to formula (XVIa) or (XVI'a):

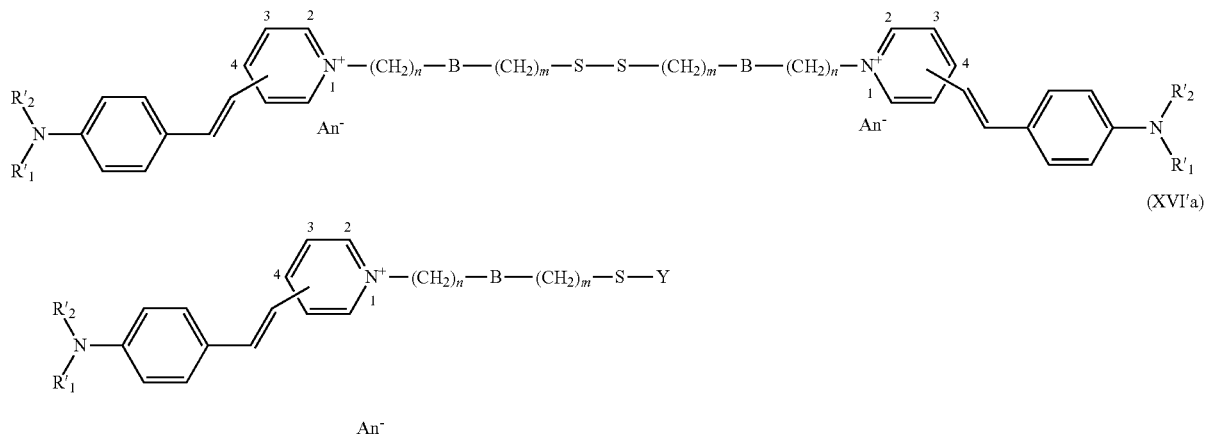

formulae (Ia) and (Ib) in which:
- $R'_1$ represents a $C_1$-$C_4$ alkyl group substituted with one or more hydroxyl groups, particularly with only one hydroxyl group, or —C(O)OR' with R' representing a hydrogen atom, a $C_1$-$C_4$ alkyl group or a group —C(O)—O⁻ and, in the latter case, an anionic counterion An⁻ is absent; preferentially, $R'_1$ represents a $C_1$-$C_4$ alkyl group substituted with a hydroxyl group;
- $R'_2$ represents a $C_1$-$C_4$ alkyl group optionally substituted with one or more hydroxyl groups, particularly with only one hydroxyl group; more particularly, $R'_1$ and $R'_2$ are identical;
- An⁻ represents an anionic counterion as defined previously;
- B, represent a divalent amido group —C(O)—N(R)—, —N(R)—C(O)—, with R representing a hydrogen atom or a group ($C_1$-$C_6$)alkyl; preferentially, R=H;
- n and m, which may be identical or different, represent an integer between 1 and 4 inclusive; preferentially, n is equal to 3 and m is equal to 2;
- Y is as defined previously;

it being understood that the bond between the pyridinium ring and the double bond of the ethylene or styryl group is located in position 2 or 4 of the pyridinium, preferably at 4.

As examples of disulfide, thiol and protected-thiol direct dyes of formula (I) of the invention, mention may be made of those having the following chemical structures:

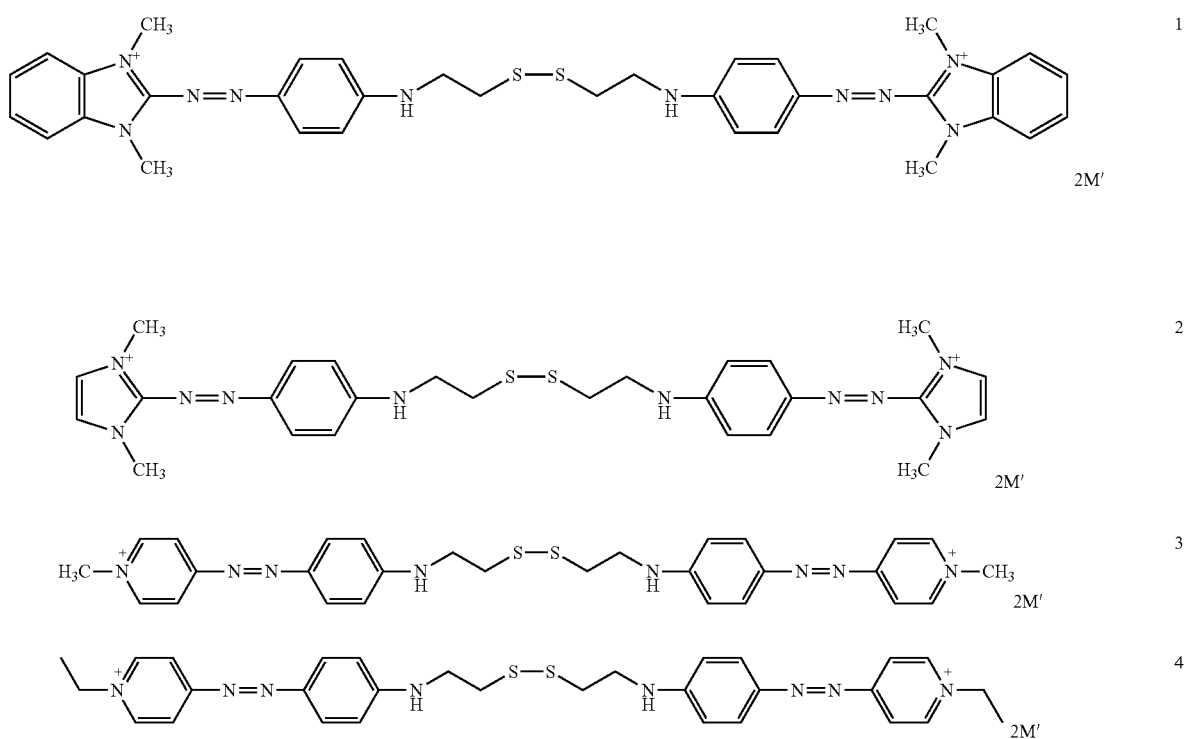

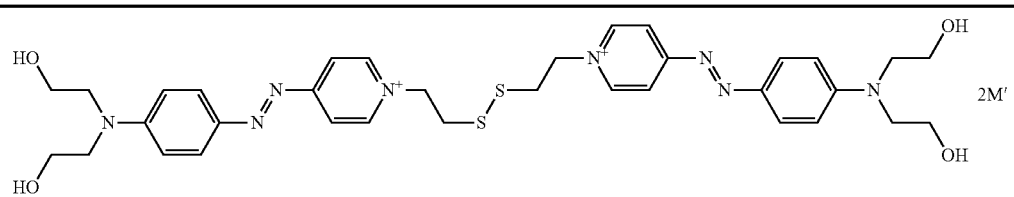
5
2M'
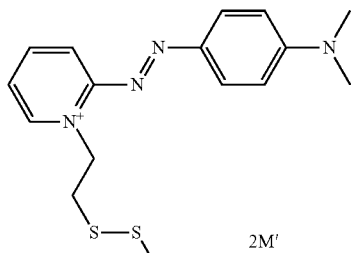
6
2M'
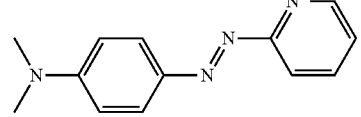
7
2M'
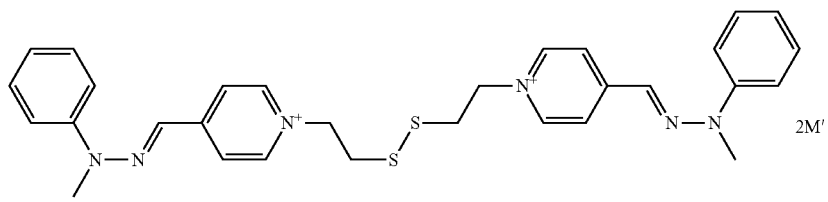 [SMILES: CN(/N=C/c1cc[n+](CCSSCC[n+]2ccc(/C=N/N(C)c3ccccc3)cc2)cc1)c1ccccc1]
8
2M'
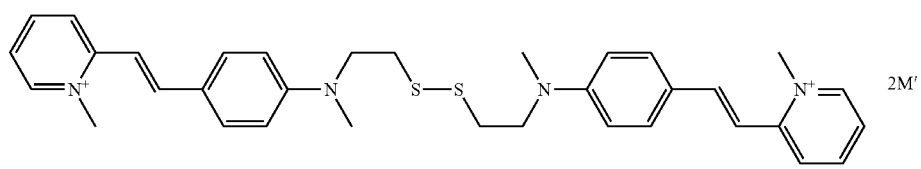 [SMILES: CN(CCSSCCN(C)c1ccc(/C=C/c2cccc[n+]2C)cc1)c1ccc(/C=C/c2cccc[n+]2C)cc1]
9
2M'
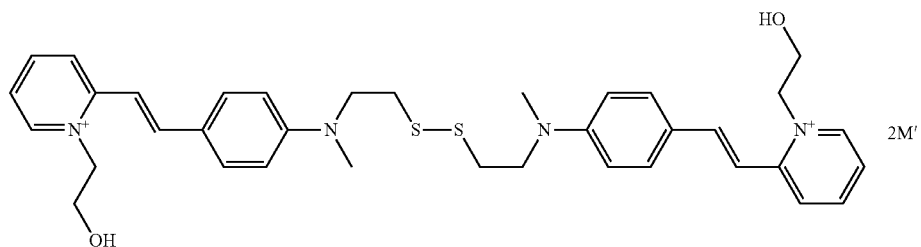 [SMILES: CN(CCSSCCN(C)c1ccc(/C=C/c2cccc[n+]2CCO)cc1)c1ccc(/C=C/c2cccc[n+]2CCO)cc1]
10
2M'
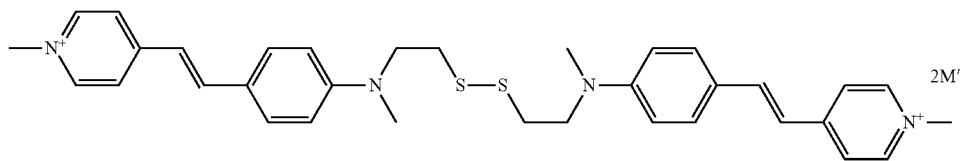
11
2M'

-continued
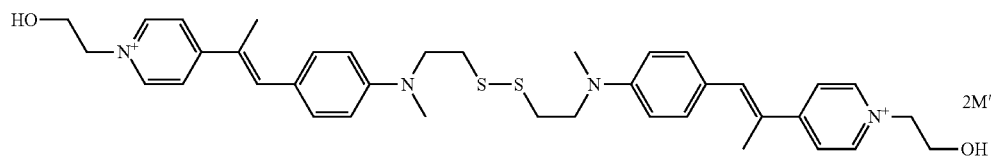 [SMILES: C/C(=C\c1ccc(N(C)CCSSCCN(C)c2ccc(/C=C(\C)c3cc[n+](CCO)cc3)cc2)cc1)c1cc[n+](CCO)cc1] 12
2M'
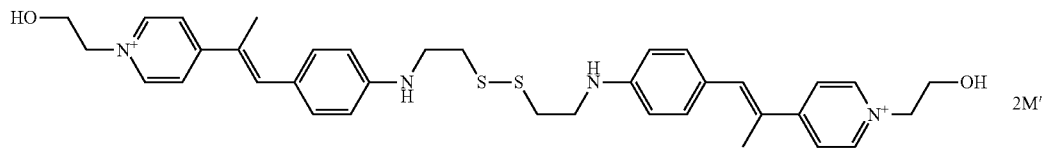 [SMILES: C/C(=C\c1ccc(NCCSSCCNc2ccc(/C=C(\C)c3cc[n+](CCO)cc3)cc2)cc1)c1cc[n+](CCO)cc1] 13
2M'
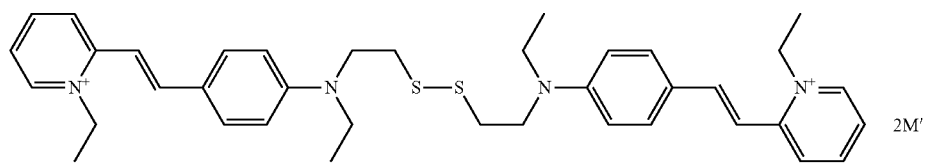 [SMILES: CCN(CCSSCCN(CC)c1ccc(/C=C/c2cccc[n+]2CC)cc1)c1ccc(/C=C/c2cccc[n+]2CC)cc1] 14
2M'
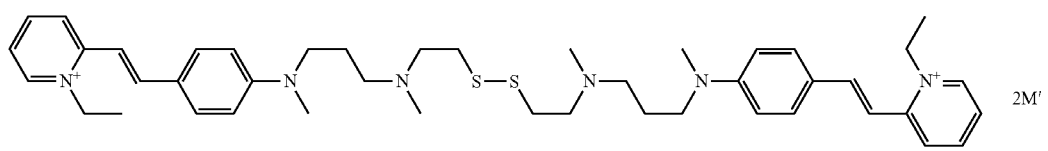 [SMILES: CC[n+]1ccccc1/C=C/c1ccc(N(C)CCCN(C)CCSSCCN(C)CCCN(C)c2ccc(/C=C/c3cccc[n+]3CC)cc2)cc1] 15
2M'
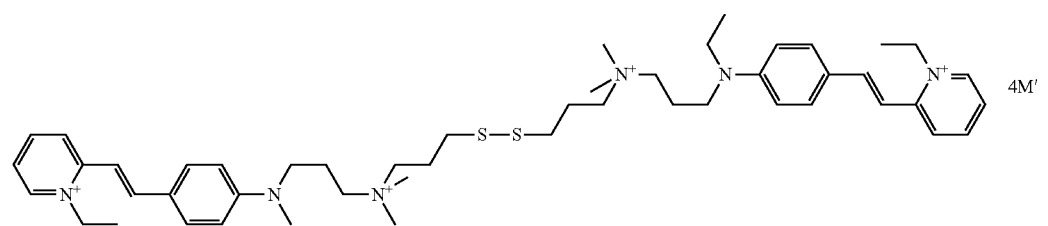 [SMILES: CCN(CCC[N+](C)(C)CCCSSCCC[N+](C)(C)CCCN(C)c1ccc(/C=C/c2cccc[n+]2CC)cc1)c1ccc(/C=C/c2cccc[n+]2CC)cc1] 16
4M'
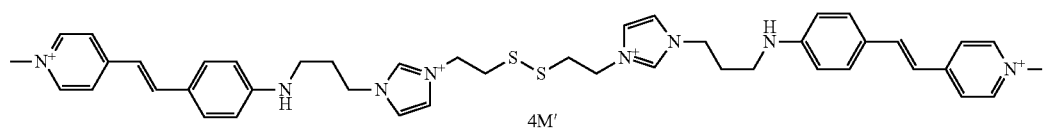 17
4M'
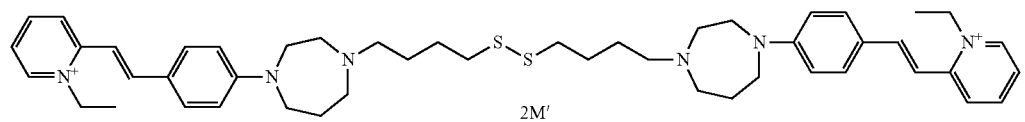 [SMILES: CC[n+]1ccccc1/C=C/c1ccc(N2CCCN(CCCCSSCCCCN3CCCN(c4ccc(/C=C/c5cccc[n+]5CC)cc4)CC3)CC2)cc1] 18
2M'
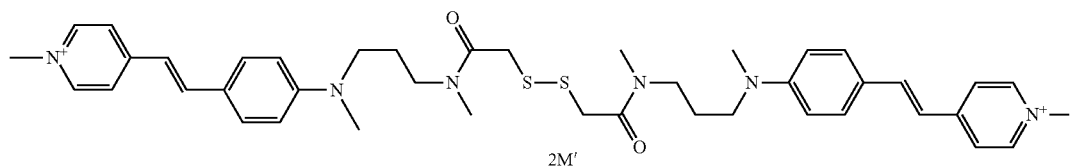 19
2M'

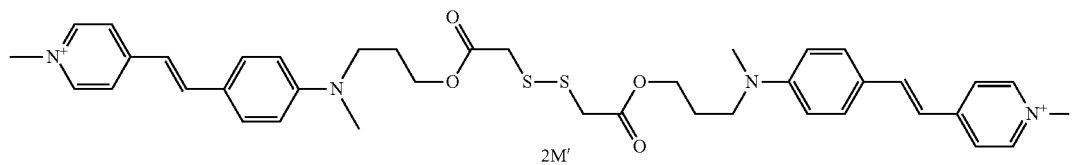
20
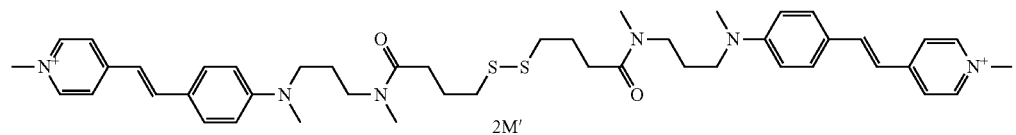
21
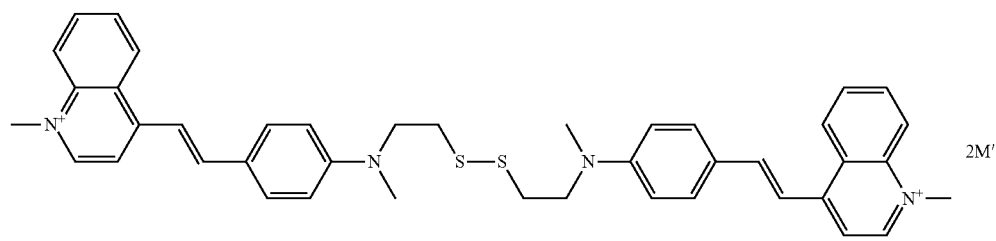
22
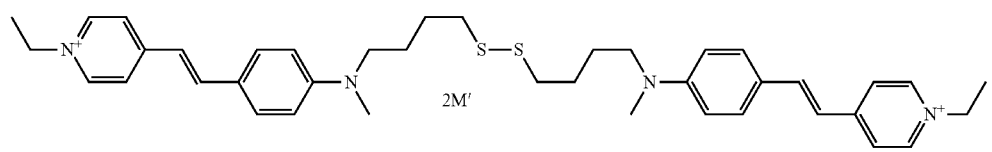 [SMILES: CC[n+]1ccc(/C=C/c2ccc(N(C)CCCCSSCCCCN(C)c3ccc(/C=C/c4cc[n+](CC)cc4)cc3)cc2)cc1]
23
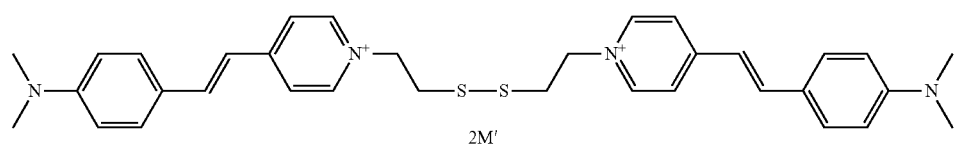
24
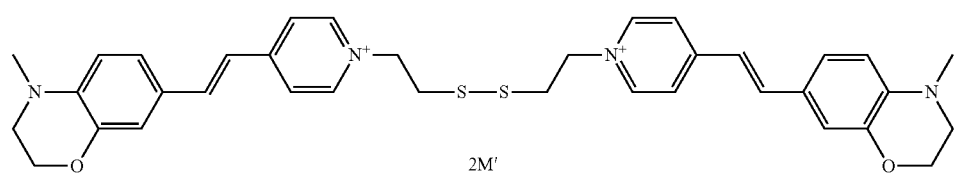 [SMILES: CN1CCOc2cc(/C=C/c3cc[n+](CCSSCC[n+]4ccc(/C=C/c5ccc6c(c5)OCCN6C)cc4)cc3)ccc21]
25
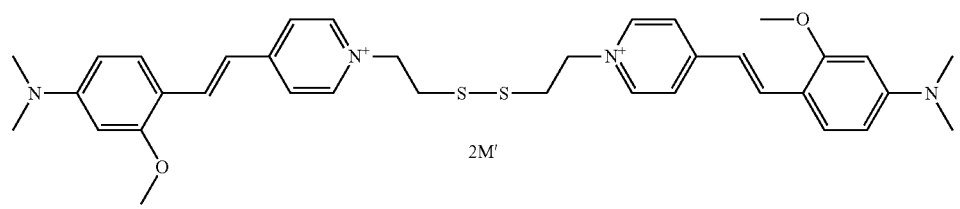
26
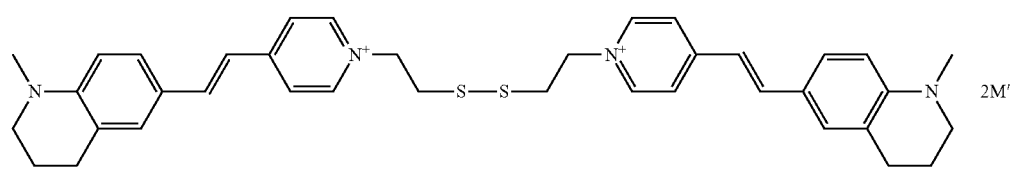 [SMILES: CN1CCCc2cc(/C=C/c3cc[n+](CCSSCC[n+]4ccc(/C=C/c5ccc6c(c5)CCCN6C)cc4)cc3)ccc21]
27
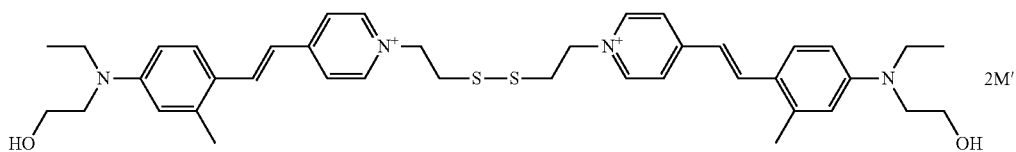 [SMILES: CCN(CCO)c1ccc(/C=C/c2cc[n+](CCSSCC[n+]3ccc(/C=C/c4ccc(N(CC)CCO)cc4C)cc3)cc2)c(C)c1]
28

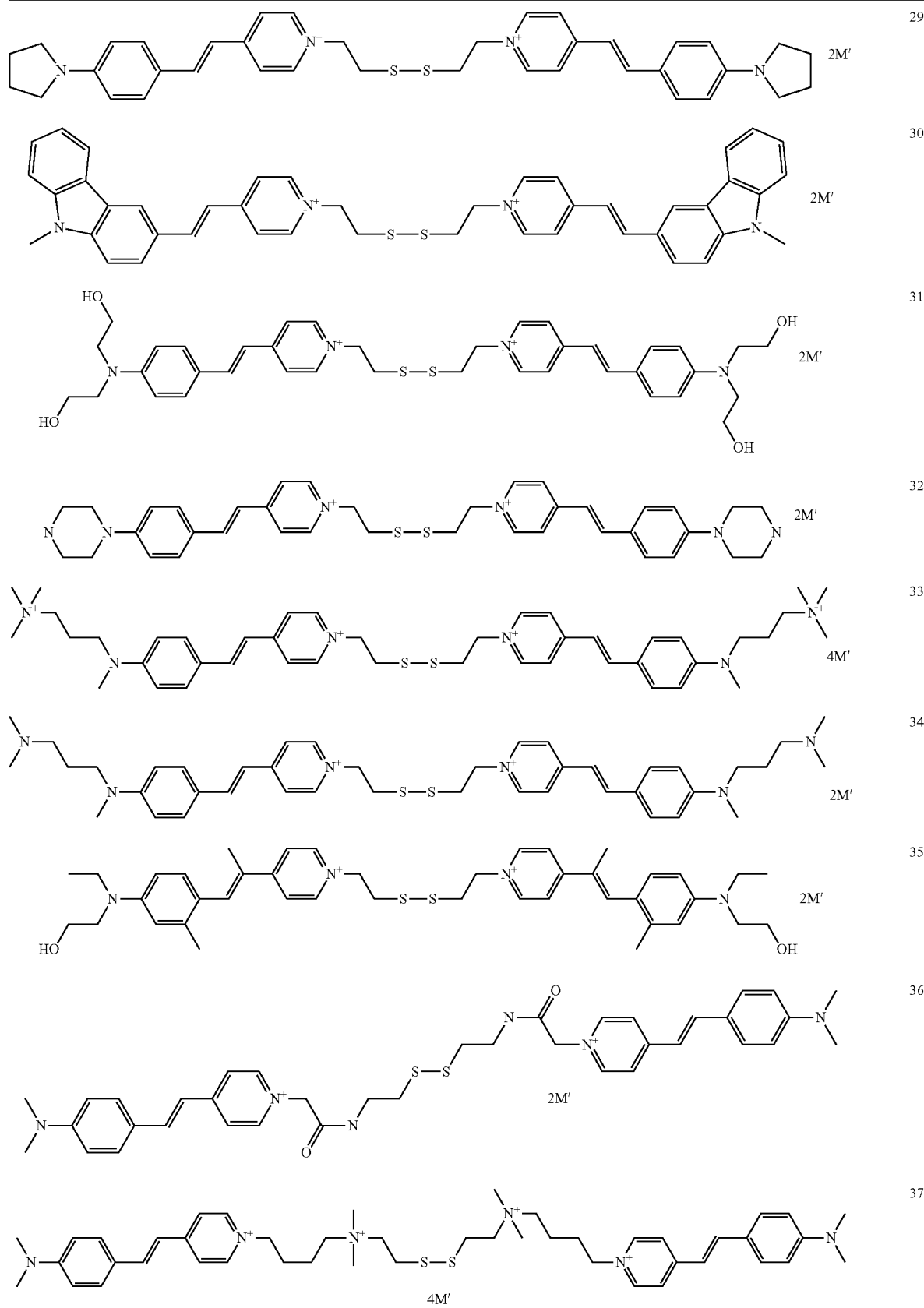

-continued
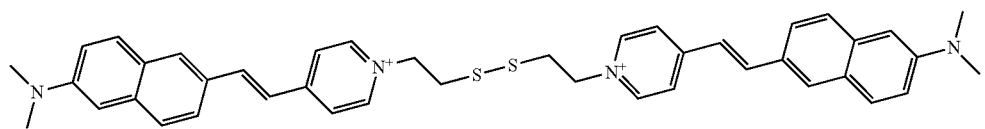
38
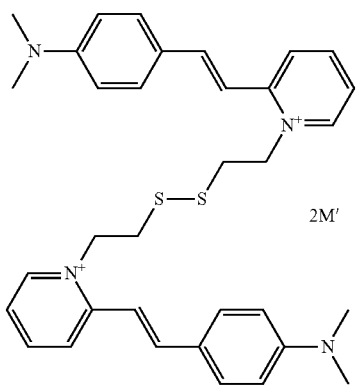 [SMILES: CN(C)c1ccc(/C=C/c2cccc[n+]2CCSSCC[n+]2ccccc2/C=C/c2ccc(N(C)C)cc2)cc1]
39
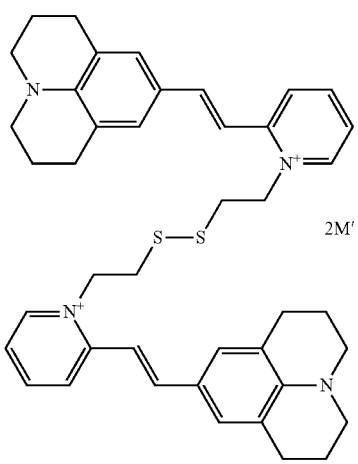 [SMILES: C(=C\c1cccc[n+]1CCSSCC[n+]1ccccc1/C=C/c1cc2c3c(c1)CCCN3CCC2)/c1cc2c3c(c1)CCCN3CCC2]
40
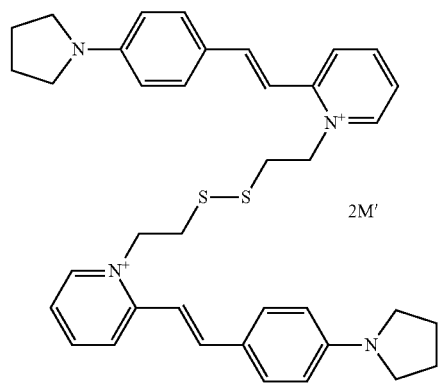 [SMILES: C(=C\c1cccc[n+]1CCSSCC[n+]1ccccc1/C=C/c1ccc(N2CCCC2)cc1)/c1ccc(N2CCCC2)cc1]
41

-continued
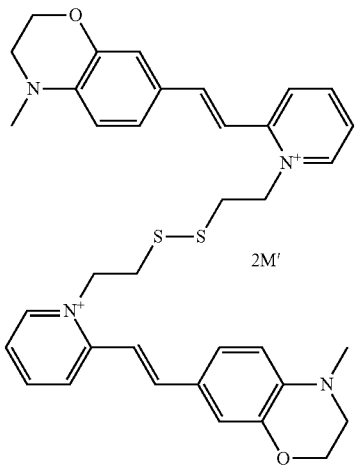 [SMILES: CN1CCOc2cc(/C=C/c3cccc[n+]3CCSSCC[n+]3ccccc3/C=C/c3ccc4c(c3)OCCN4C)ccc21]
42
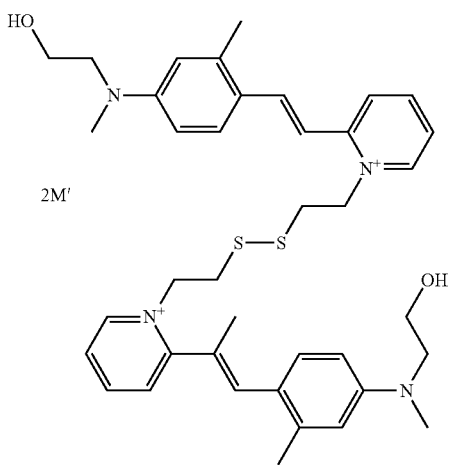 [SMILES: C/C(=C\c1ccc(N(C)CCO)cc1C)c1cccc[n+]1CCSSCC[n+]1ccccc1/C=C/c1ccc(N(C)CCO)cc1C]
43
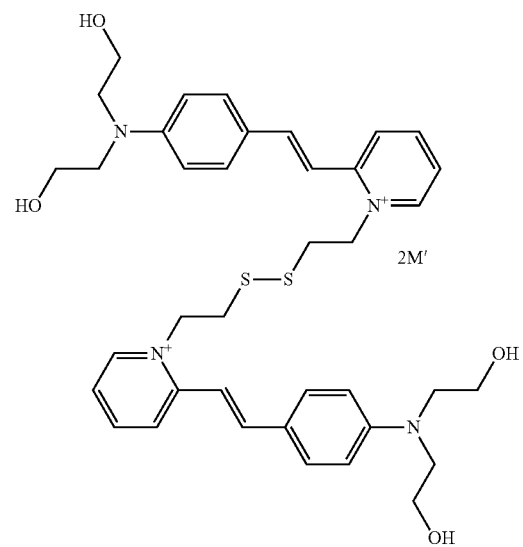 [SMILES: OCCN(CCO)c1ccc(/C=C/c2cccc[n+]2CCSSCC[n+]2ccccc2/C=C/c2ccc(N(CCO)CCO)cc2)cc1]
44

-continued
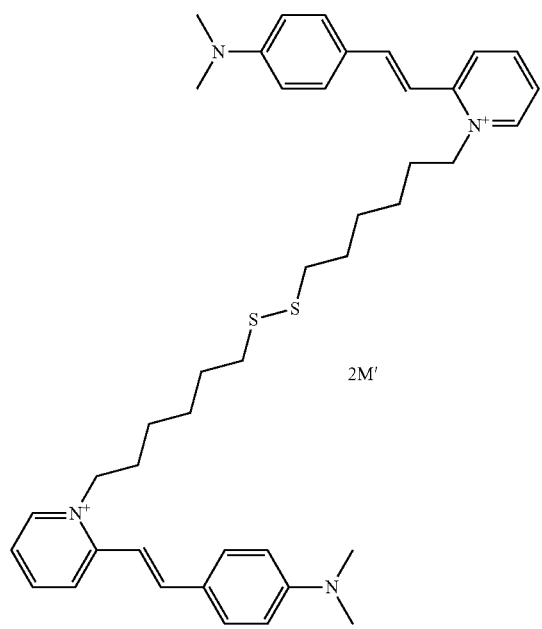 [SMILES: CN(C)c1ccc(/C=C/c2cccc[n+]2CCCCCCSSCCCCCC[n+]2ccccc2/C=C/c2ccc(N(C)C)cc2)cc1]
45
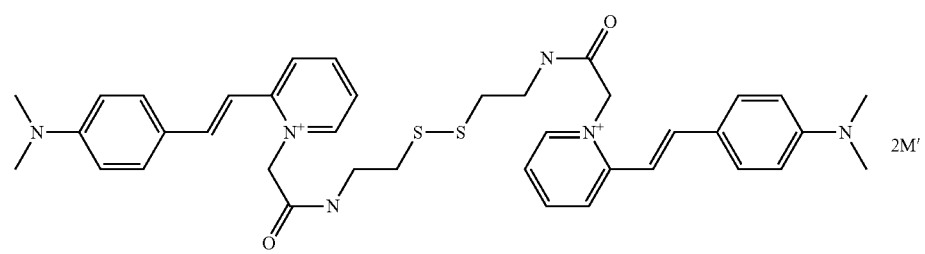
46
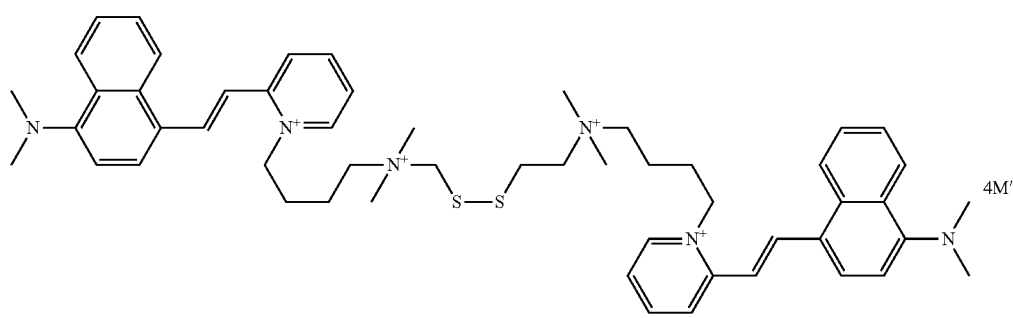
47

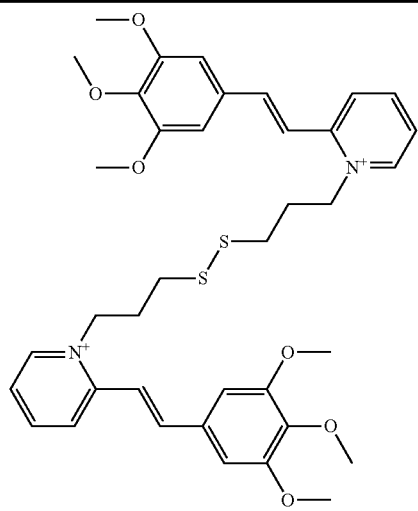
48
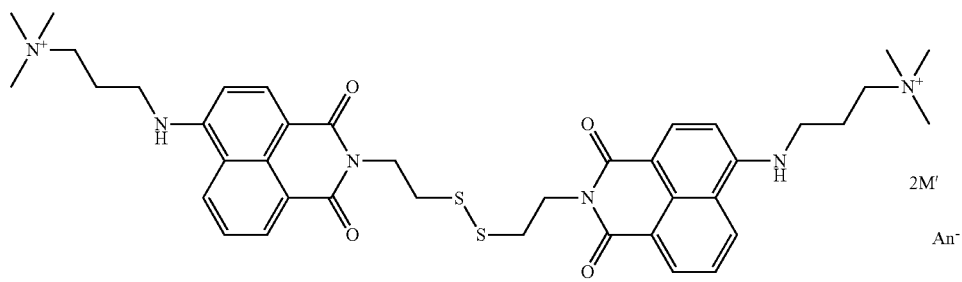
49
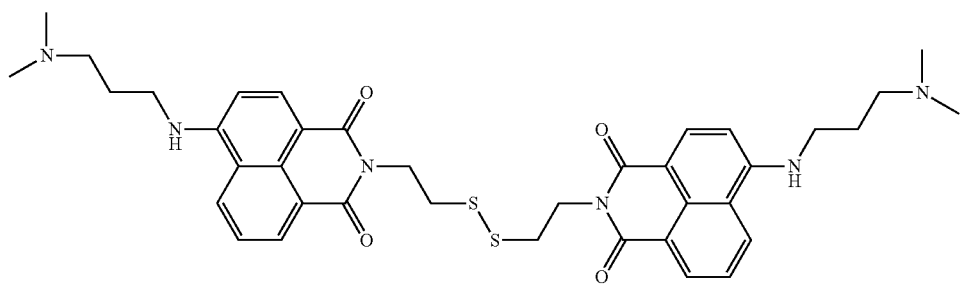
49a
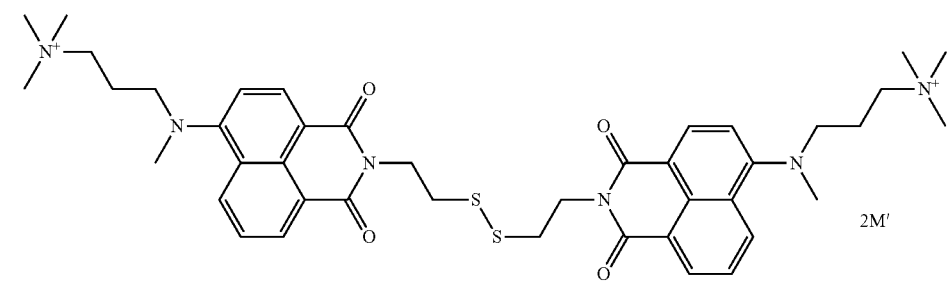
50
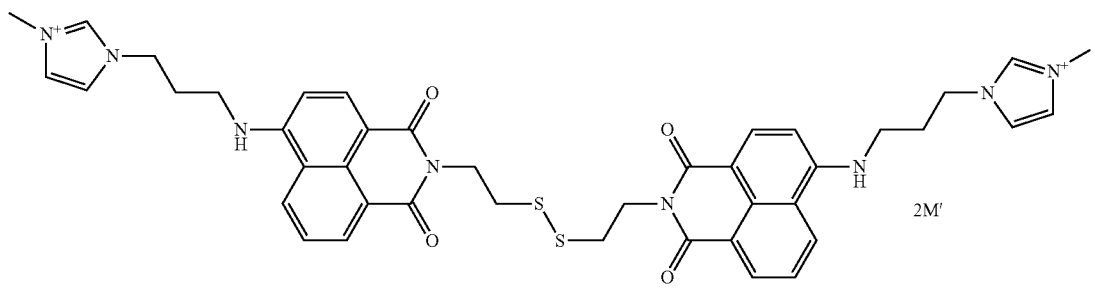
51

-continued
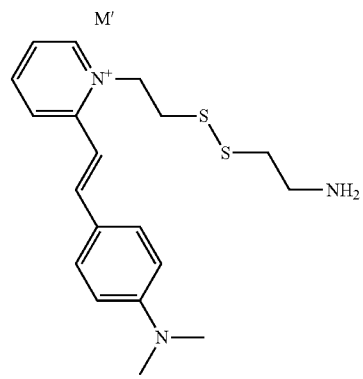 [SMILES: CN(C)c1ccc(/C=C/c2cccc[n+]2CCSSCCN)cc1]
52
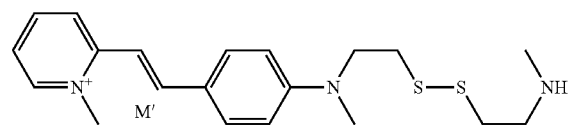 [SMILES: CNCCSSCCN(C)c1ccc(/C=C/c2cccc[n+]2C)cc1]
53
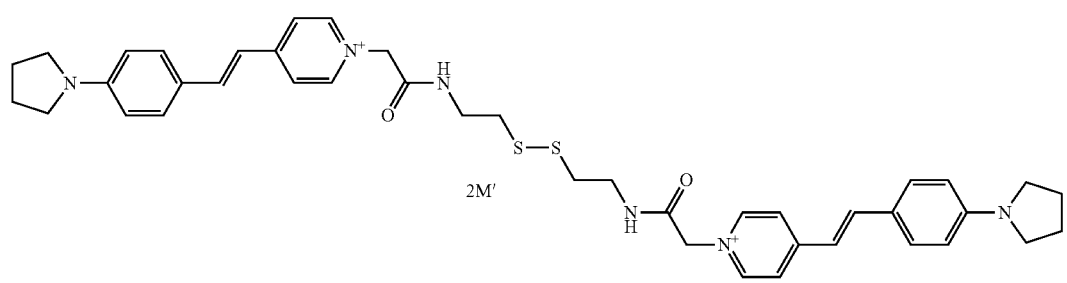 [SMILES: O=C(C[n+]1ccc(/C=C/c2ccc(N3CCCC3)cc2)cc1)NCCSSCCNC(=O)C[n+]1ccc(/C=C/c2ccc(N3CCCC3)cc2)cc1]
54
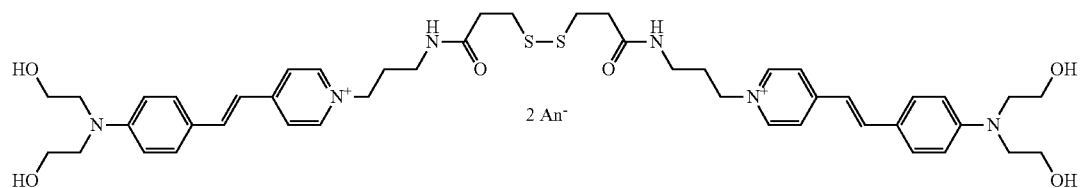 [SMILES: O=C(CCSSCCC(=O)NCCC[n+]1ccc(/C=C/c2ccc(N(CCO)CCO)cc2)cc1)NCCC[n+]1ccc(/C=C/c2ccc(N(CCO)CCO)cc2)cc1]
55
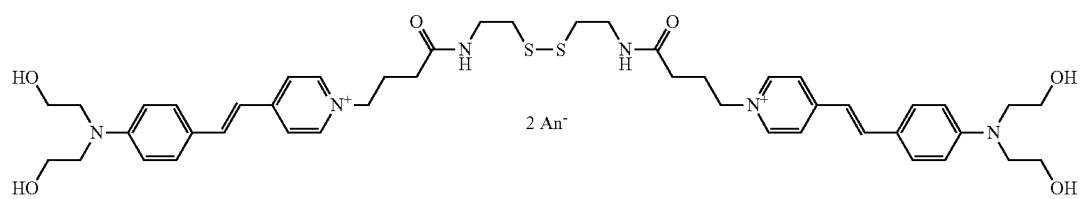 [SMILES: O=C(CCC[n+]1ccc(/C=C/c2ccc(N(CCO)CCO)cc2)cc1)NCCSSCCNC(=O)CCC[n+]1ccc(/C=C/c2ccc(N(CCO)CCO)cc2)cc1]
56
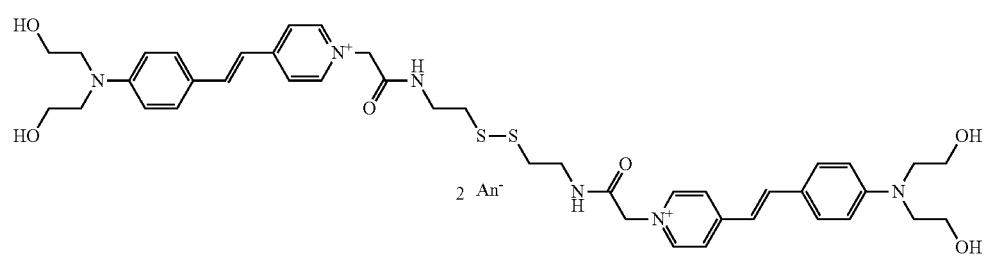 [SMILES: O=C(C[n+]1ccc(/C=C/c2ccc(N(CCO)CCO)cc2)cc1)NCCSSCCNC(=O)C[n+]1ccc(/C=C/c2ccc(N(CCO)CCO)cc2)cc1]
57

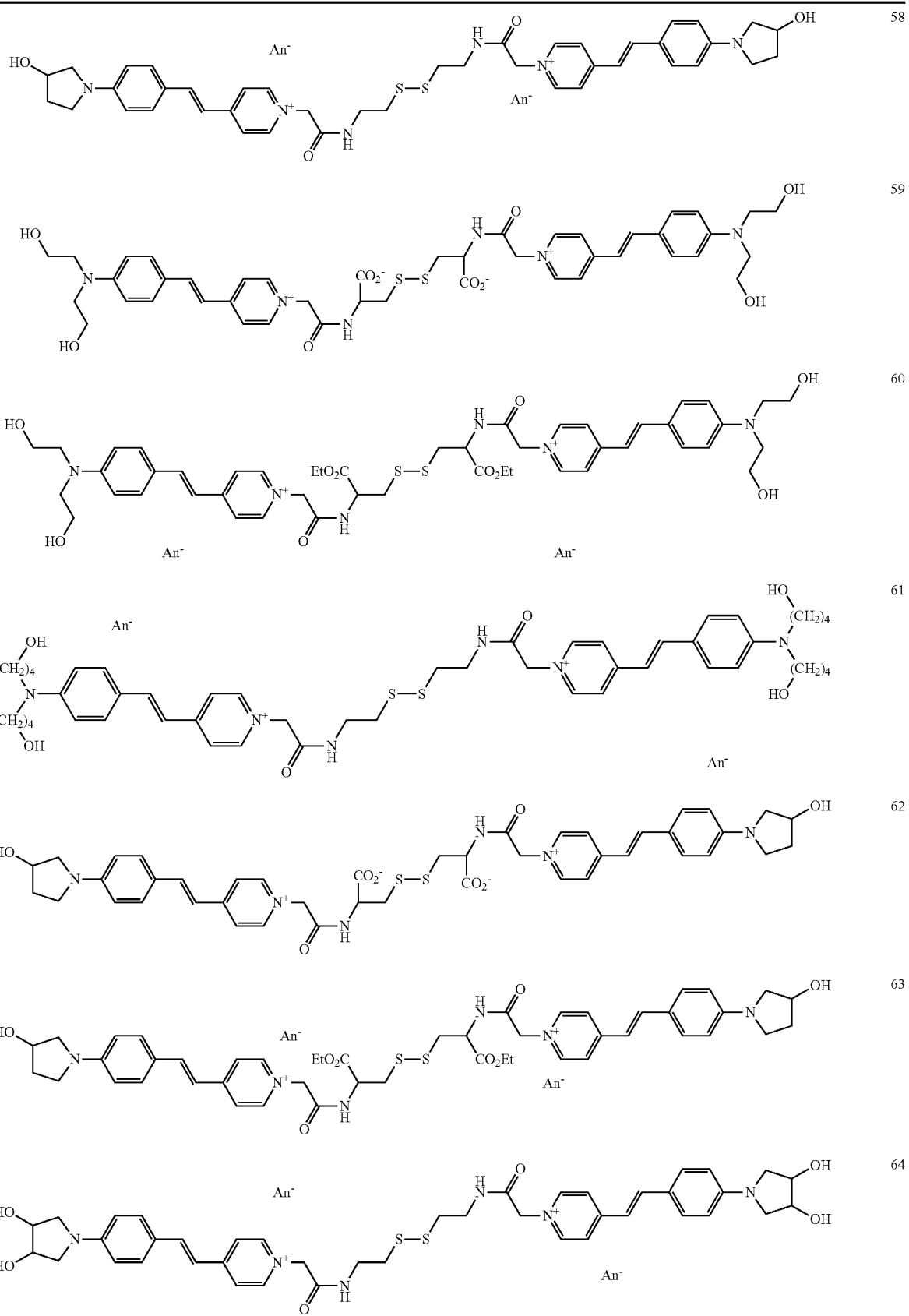

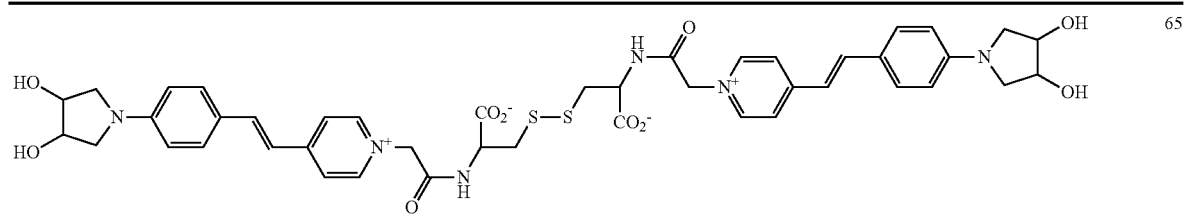
65
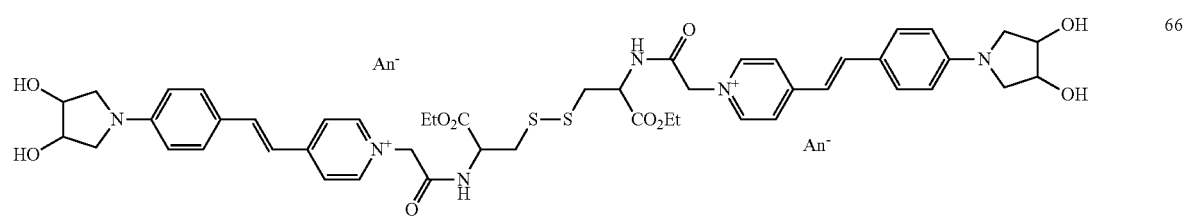
66
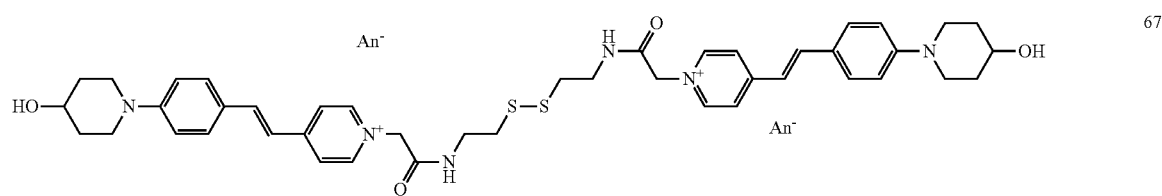
67
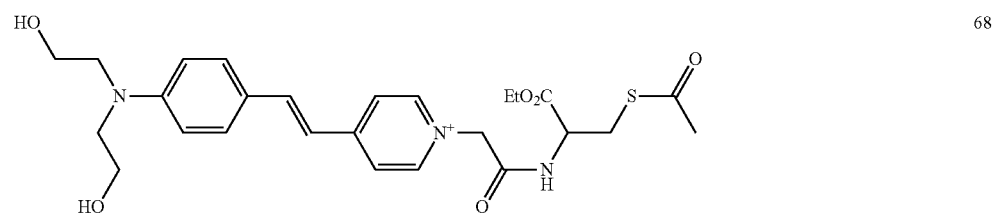
68
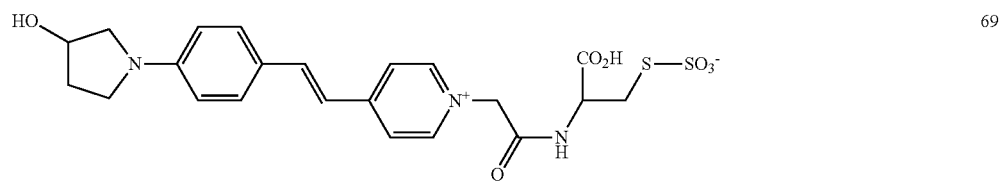
69
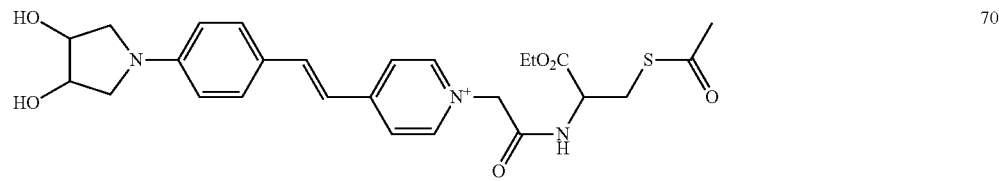
70

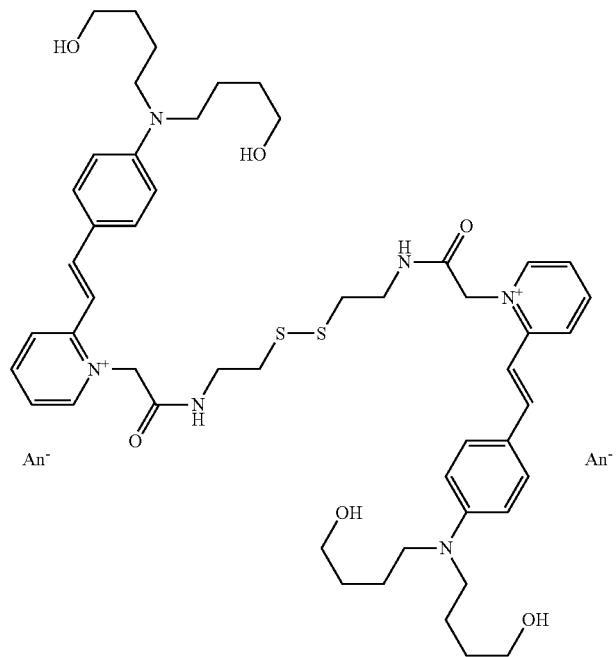 [SMILES: O=C(C[n+]1ccccc1/C=C/c1ccc(N(CCCCO)CCCCO)cc1)NCCSSCCNC(=O)C[n+]1ccccc1/C=C/c1ccc(N(CCCCO)CCCCO)cc1]
71
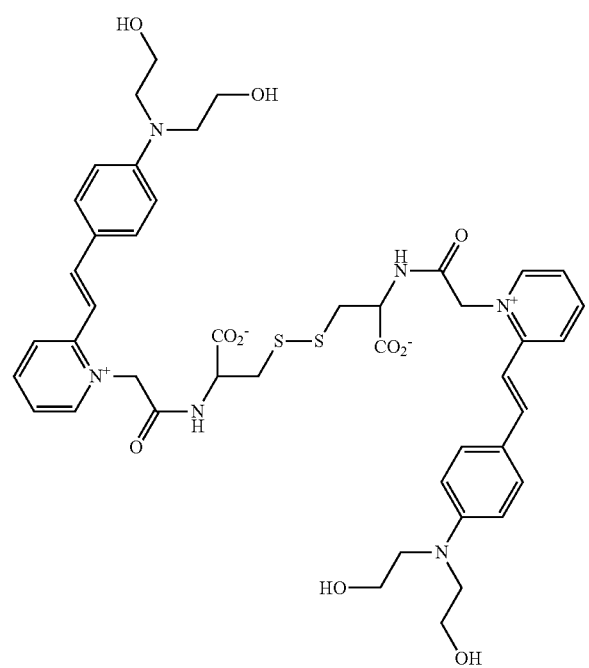
72

73
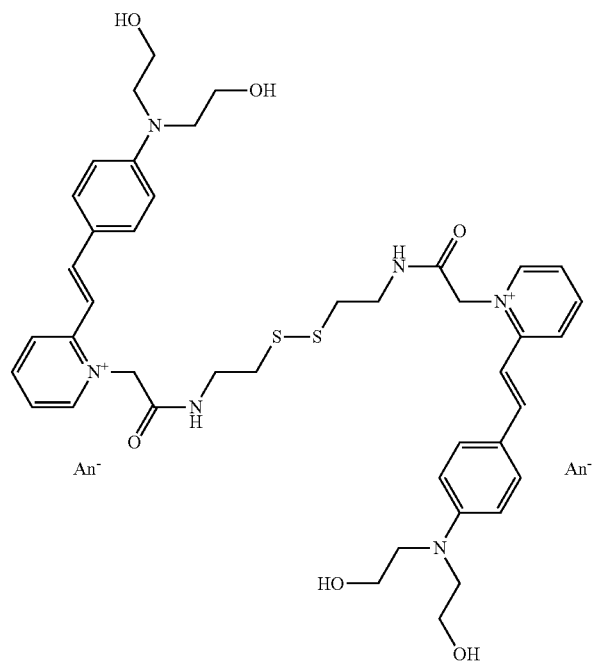 [SMILES: O=C(C[n+]1ccccc1/C=C/c1ccc(N(CCO)CCO)cc1)NCCSSCCNC(=O)C[n+]1ccccc1/C=C/c1ccc(N(CCO)CCO)cc1]
74
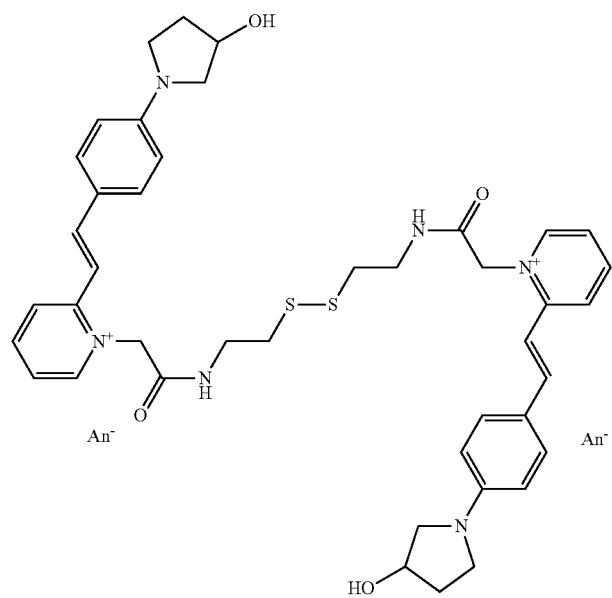 [SMILES: O=C(C[n+]1ccccc1/C=C/c1ccc(N2CCC(O)C2)cc1)NCCSSCCNC(=O)C[n+]1ccccc1/C=C/c1ccc(N2CCC(O)C2)cc1]

-continued
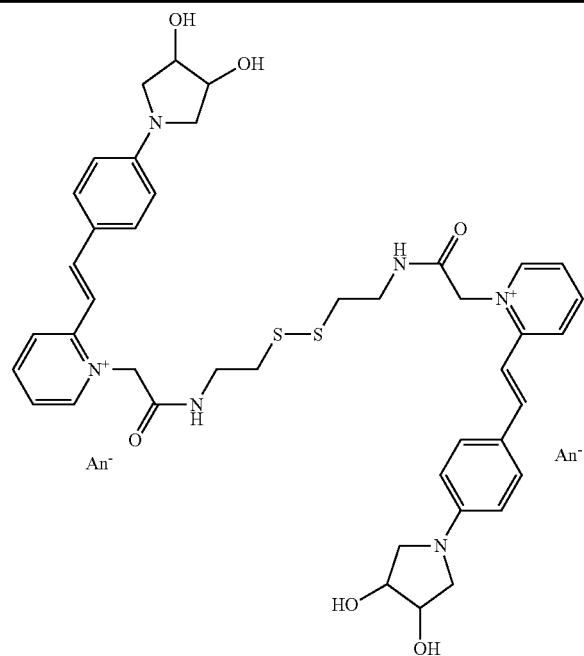
75
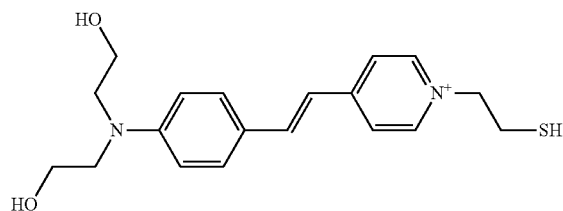 [SMILES: OCCN(CCO)c1ccc(/C=C/c2cc[n+](CCS)cc2)cc1]
76
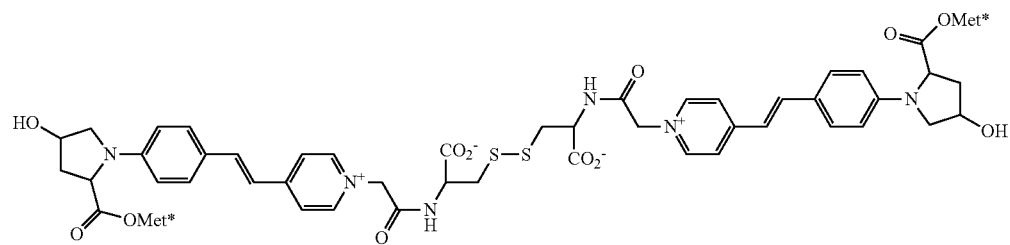
77
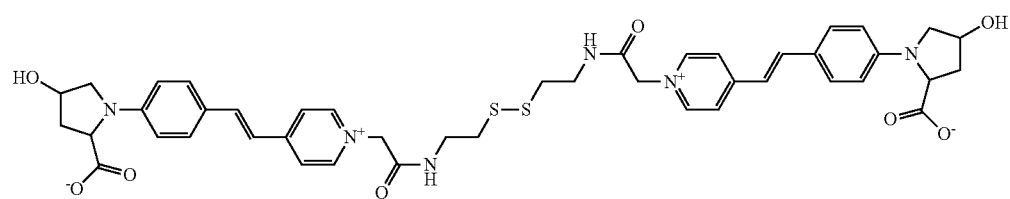
78

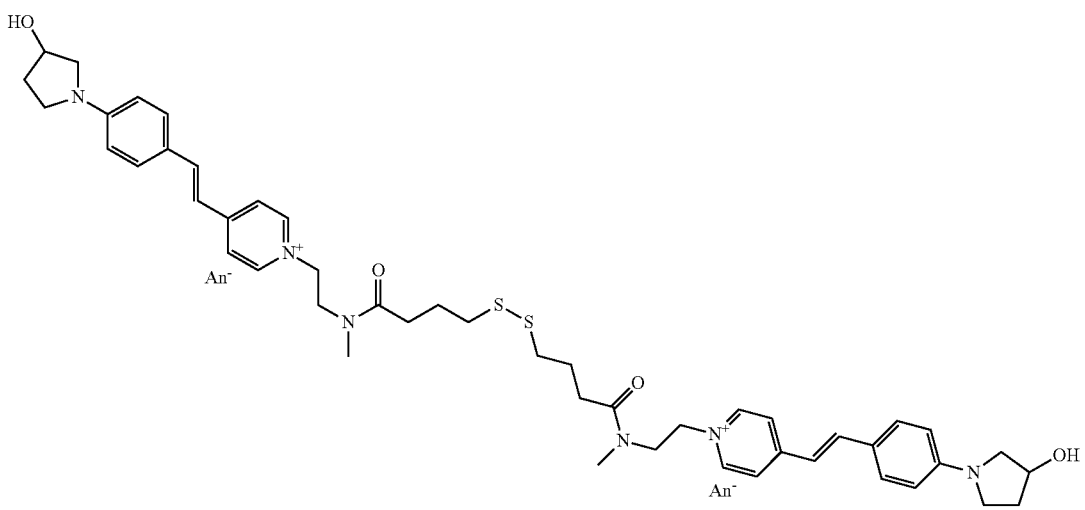 [SMILES: CN(CC[n+]1ccc(/C=C/c2ccc(N3CCC(O)C3)cc2)cc1)C(=O)CCCSSCCCC(=O)N(C)CC[n+]1ccc(/C=C/c2ccc(N3CCC(O)C3)cc2)cc1]
79
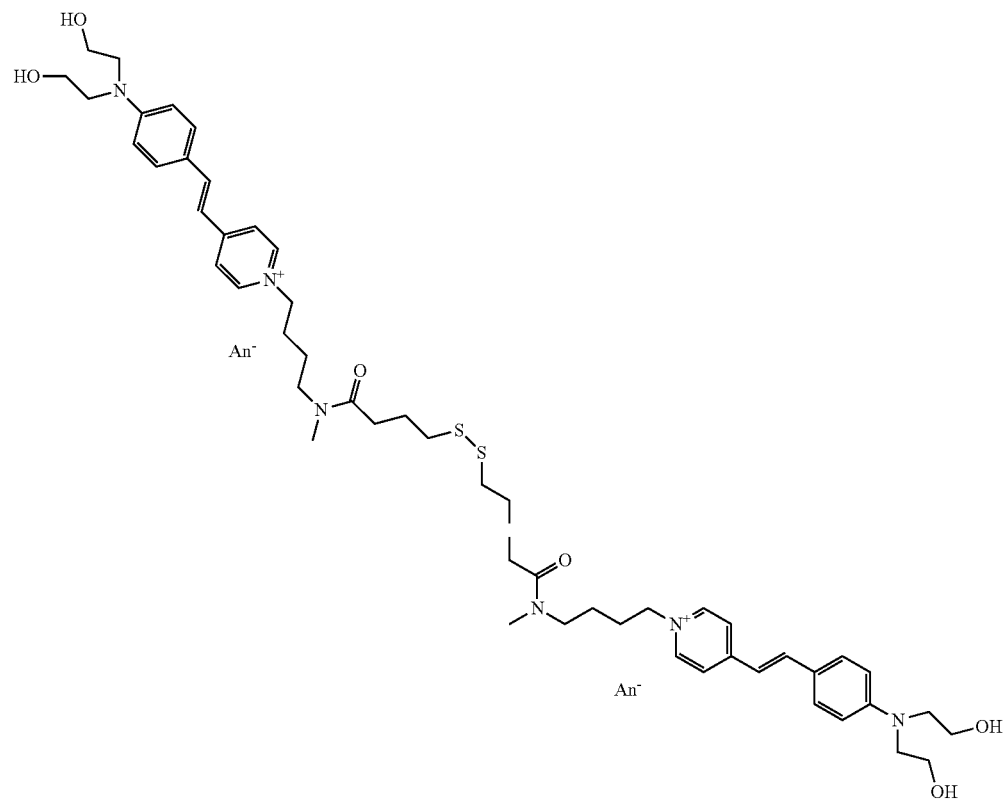 [SMILES: CN(CCCC[n+]1ccc(/C=C/c2ccc(N(CCO)CCO)cc2)cc1)C(=O)CCCSSCCCC(=O)N(C)CCCC[n+]1ccc(/C=C/c2ccc(N(CCO)CCO)cc2)cc1]
80

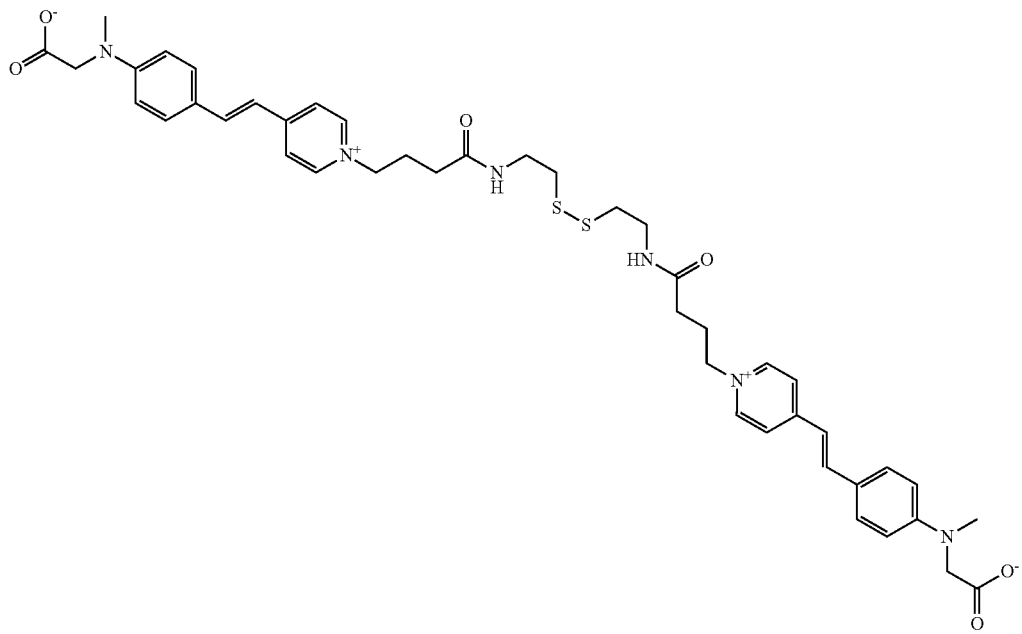 [SMILES: CN(CC(=O)[O-])c1ccc(/C=C/c2cc[n+](CCCC(=O)NCCSSCCNC(=O)CCC[n+]3ccc(/C=C/c4ccc(N(C)CC(=O)[O-])cc4)cc3)cc2)cc1]
81
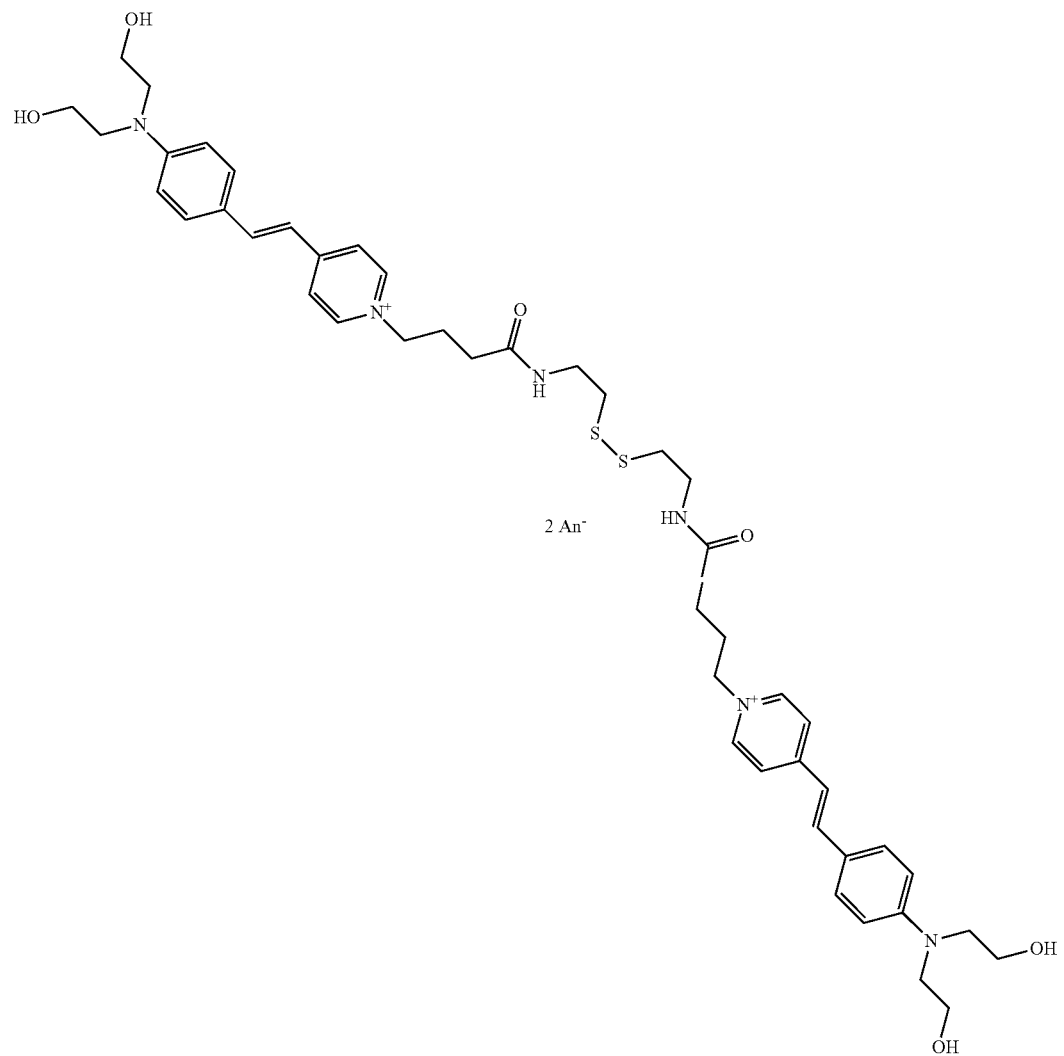 [SMILES: O=C(CCC[n+]1ccc(/C=C/c2ccc(N(CCO)CCO)cc2)cc1)NCCSSCCNC(=O)CCC[n+]1ccc(/C=C/c2ccc(N(CCO)CCO)cc2)cc1]
82

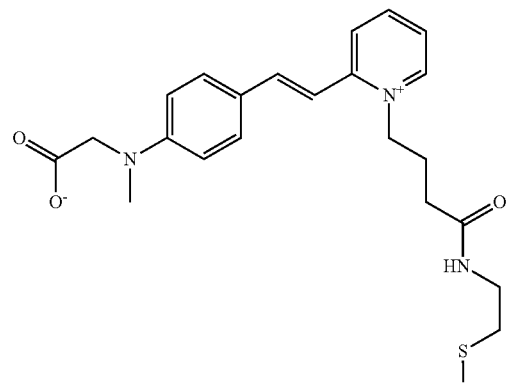
83
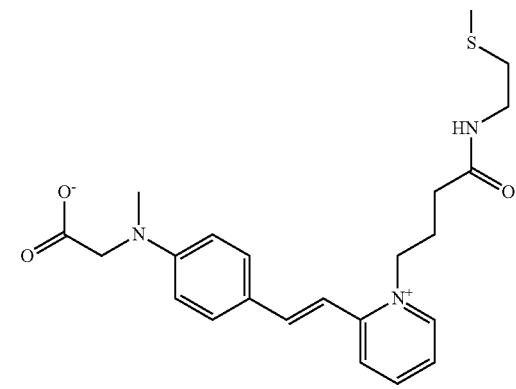
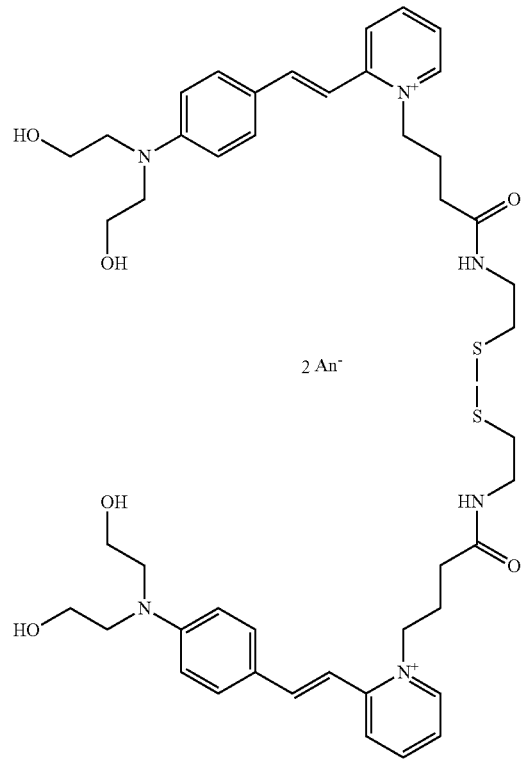 [SMILES: O=C(CCC[n+]1ccccc1/C=C/c1ccc(N(CCO)CCO)cc1)NCCSSCCNC(=O)CCC[n+]1ccccc1/C=C/c1ccc(N(CCO)CCO)cc1]
84

-continued
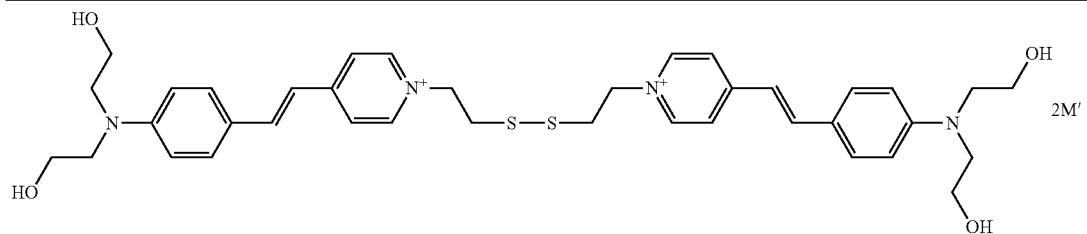
85
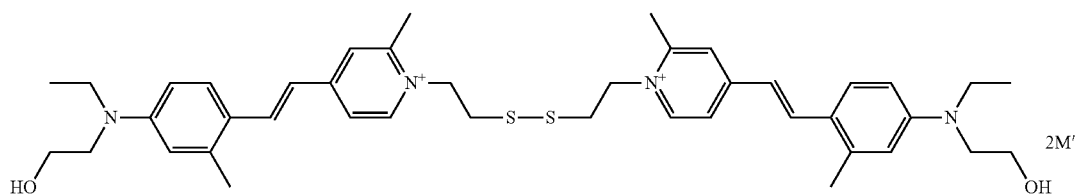 [SMILES: CCN(CCO)c1ccc(/C=C/c2cc[n+](CCSSCC[n+]3ccc(/C=C/c4ccc(N(CC)CCO)cc4C)cc3C)c(C)c2)c(C)c1]
86
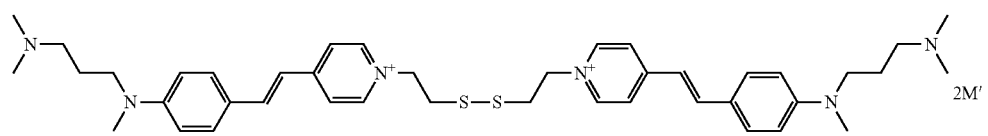
87
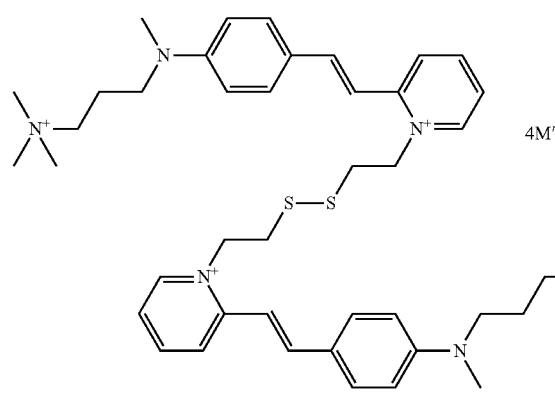
88
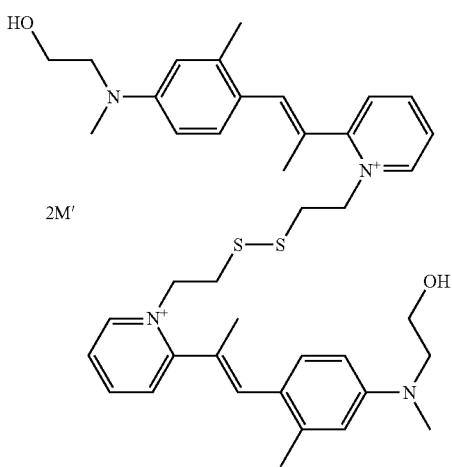 [SMILES: C/C(=C\c1ccc(N(C)CCO)cc1C)c1cccc[n+]1CCSSCC[n+]1ccccc1/C(C)=C/c1ccc(N(C)CCO)cc1C]
89

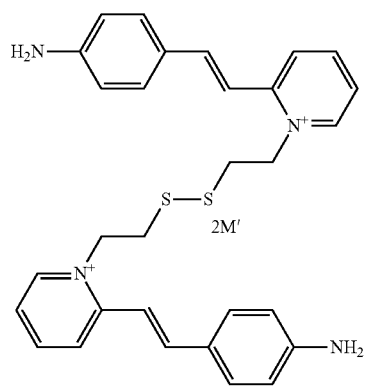 [SMILES: Nc1ccc(/C=C/c2cccc[n+]2CCSSCC[n+]2ccccc2/C=C/c2ccc(N)cc2)cc1]
90
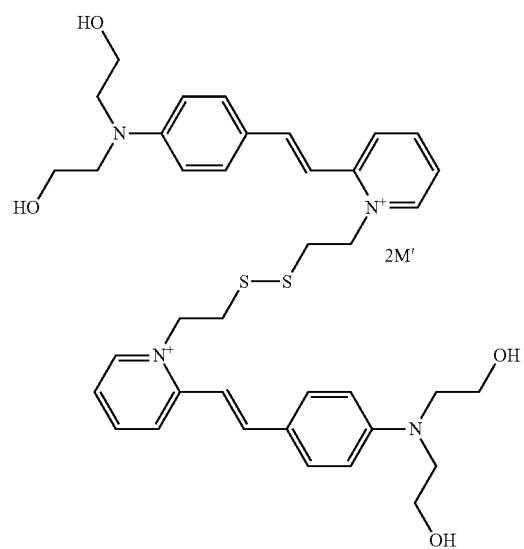 [SMILES: OCCN(CCO)c1ccc(/C=C/c2cccc[n+]2CCSSCC[n+]2ccccc2/C=C/c2ccc(N(CCO)CCO)cc2)cc1]
91
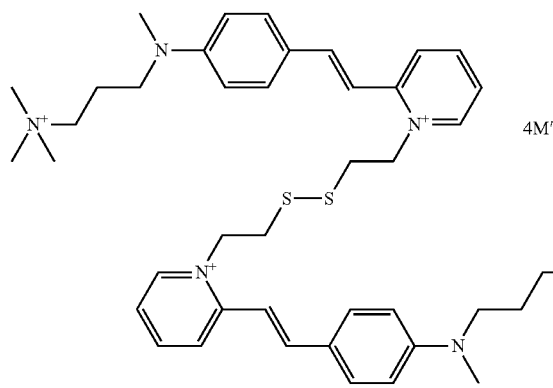
92
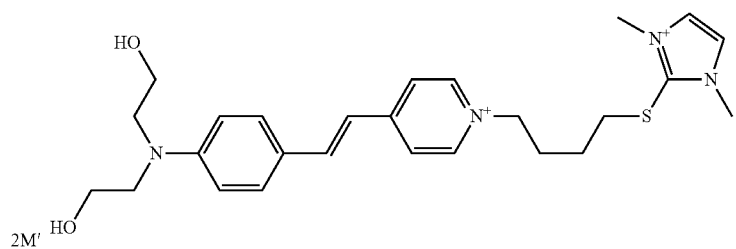 [SMILES: Cn1cc[n+](C)c1SCCCC[n+]1ccc(/C=C/c2ccc(N(CCO)CCO)cc2)cc1]
93

| | |
|---|---|
| 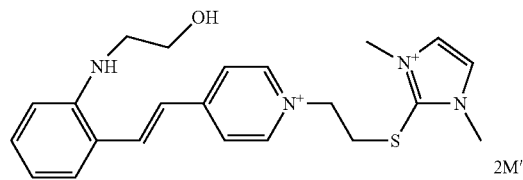 [SMILES: Cn1cc[n+](C)c1SCC[n+]1ccc(/C=C/c2ccccc2NCCO)cc1] 2M' | 94 |
| 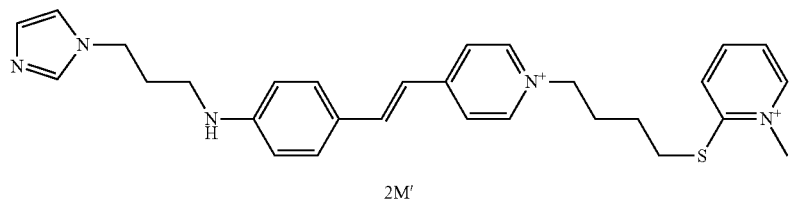 [SMILES: C[n+]1ccccc1SCCCC[n+]1ccc(/C=C/c2ccc(NCCCn3ccnc3)cc2)cc1] 2M' | 95 |
| 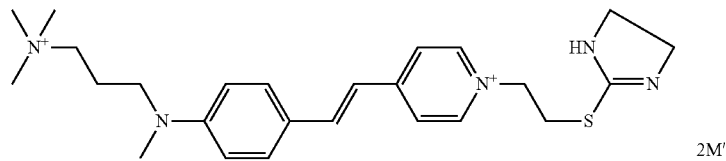 [SMILES: CN(CCC[N+](C)(C)C)c1ccc(/C=C/c2cc[n+](CCSC3=NCCN3)cc2)cc1] 2M' | 96 |
| 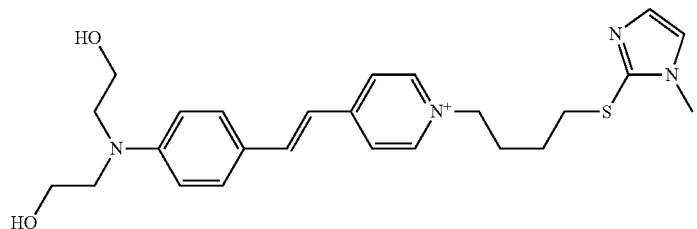 M' | 97 |
| 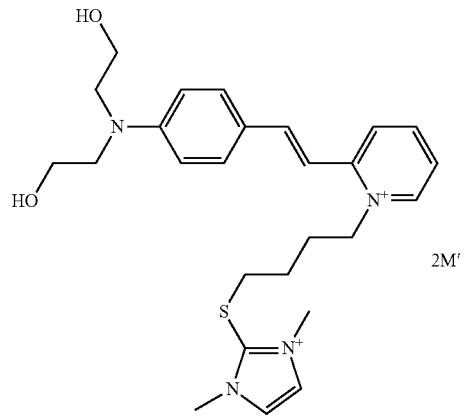 [SMILES: Cn1cc[n+](C)c1SCCCC[n+]1ccccc1/C=C/c1ccc(N(CCO)CCO)cc1] 2M' | 98 |
| 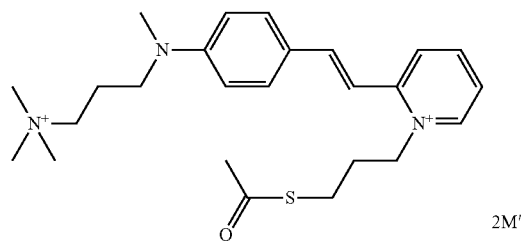 [SMILES: CC(=O)SCCC[n+]1ccccc1/C=C/c1ccc(N(C)CCC[N+](C)(C)C)cc1] 2M' | 99 |

-continued
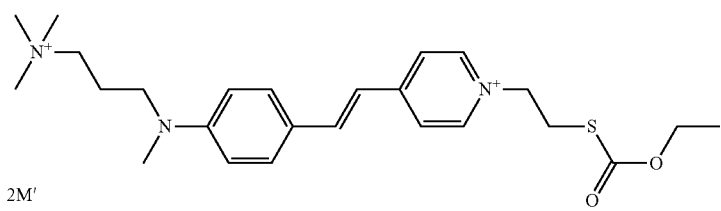 [SMILES: CCOC(=O)SCC[n+]1ccc(/C=C/c2ccc(N(C)CCC[N+](C)(C)C)cc2)cc1]
2M′
100
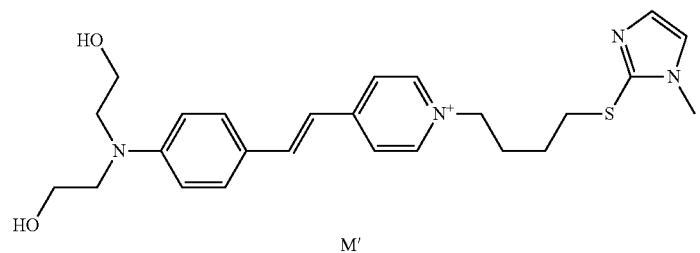 [SMILES: Cn1ccnc1SCCCC[n+]1ccc(/C=C/c2ccc(N(CCO)CCO)cc2)cc1]
M′
101
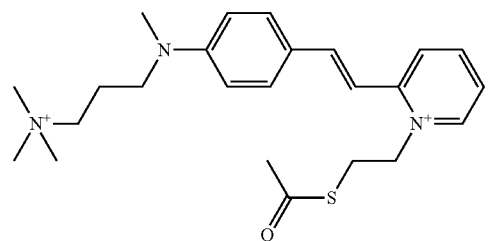
2M′
102
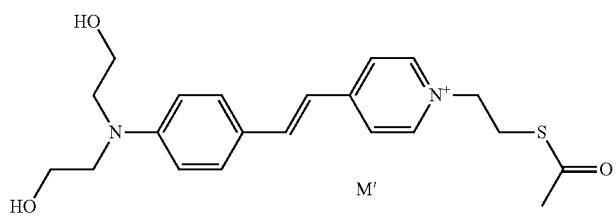
M′
102
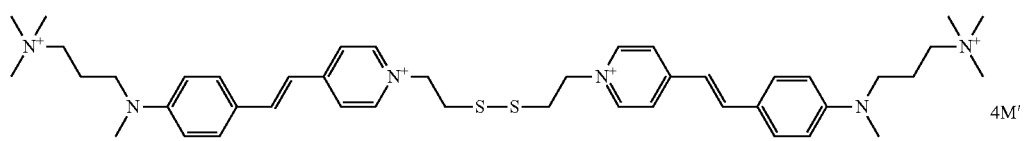
4M′
103
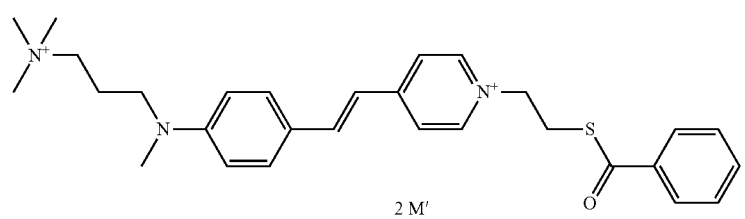 [SMILES: CN(CCC[N+](C)(C)C)c1ccc(/C=C/c2cc[n+](CCSC(=O)c3ccccc3)cc2)cc1]
2 M′
104
M′
105
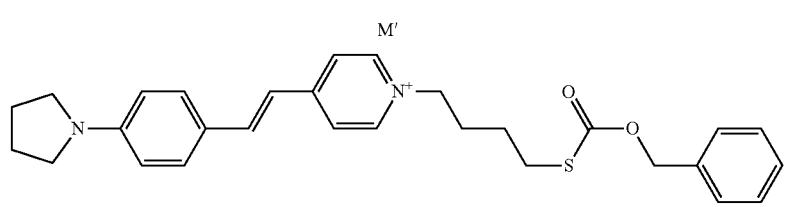 [SMILES: O=C(OCc1ccccc1)SCCCC[n+]1ccc(/C=C/c2ccc(N3CCCC3)cc2)cc1]

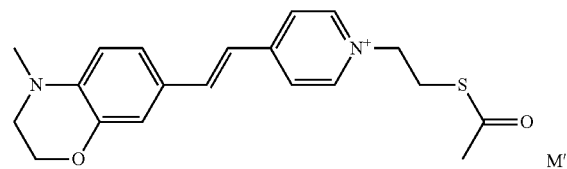 [SMILES: CC(=O)SCC[n+]1ccc(/C=C/c2ccc3c(c2)OCCN3C)cc1]
106
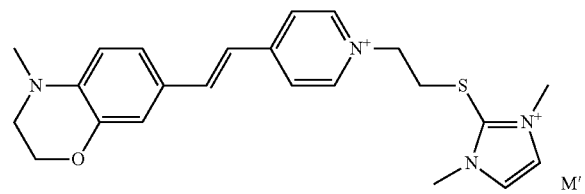 [SMILES: CN1CCOc2cc(/C=C/c3cc[n+](CCSc4n(C)cc[n+]4C)cc3)ccc21]
107
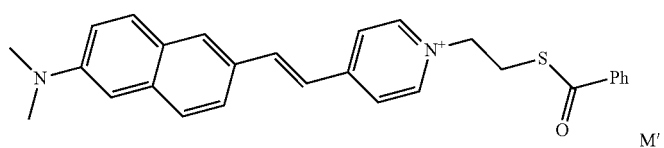 [SMILES: CN(C)c1ccc2cc(/C=C/c3cc[n+](CCSC(=O)c4ccccc4)cc3)ccc2c1]
108
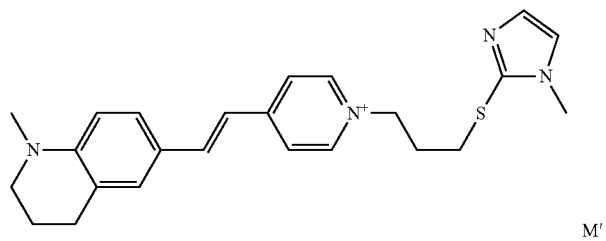 [SMILES: CN1CCCc2cc(/C=C/c3cc[n+](CCCSc4nccn4C)cc3)ccc21]
109
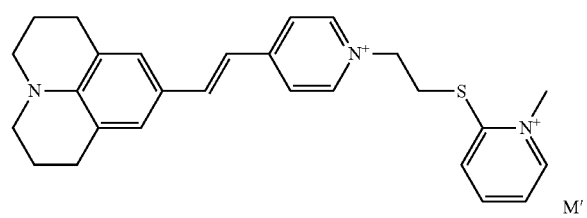 [SMILES: C[n+]1ccccc1SCC[n+]1ccc(/C=C/c2cc3c4c(c2)CCCN4CCC3)cc1]
110
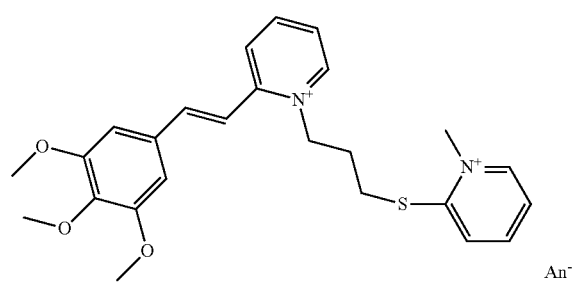 [SMILES: COc1cc(/C=C/c2cccc[n+]2CCCSc2cccc[n+]2C)cc(OC)c1OC]
111
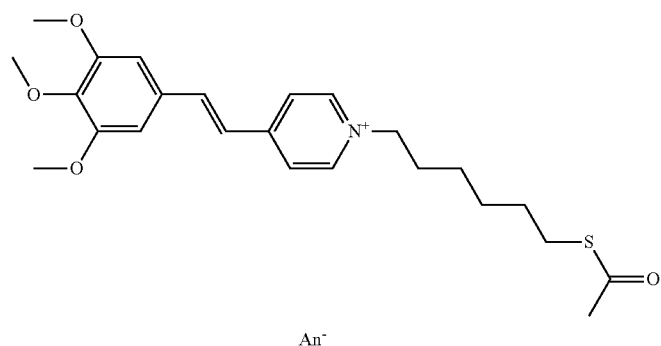 [SMILES: COc1cc(/C=C/c2cc[n+](CCCCCCSC(C)=O)cc2)cc(OC)c1OC]
112

-continued
| | |
|---|---|
| 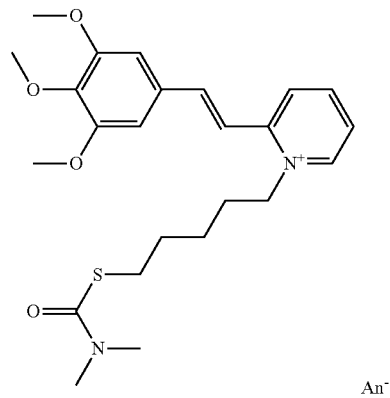 [SMILES: COc1cc(/C=C/c2cccc[n+]2CCCCCSC(=O)N(C)C)cc(OC)c1OC] An⁻ | 113 |
| 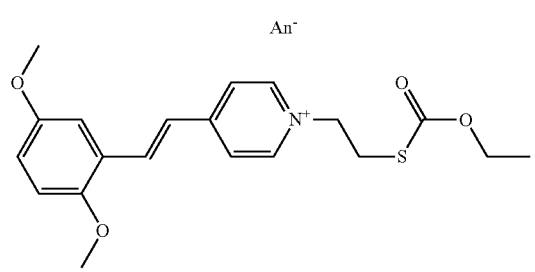 [SMILES: CCOC(=O)SCC[n+]1ccc(/C=C/c2cc(OC)ccc2OC)cc1] An⁻ | 114 |
| 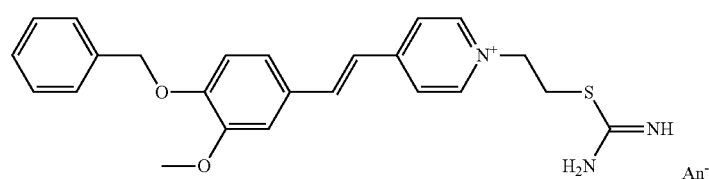 [SMILES: COc1cc(/C=C/c2cc[n+](CCSC(=N)N)cc2)ccc1OCc1ccccc1] An⁻ | 115 |
| 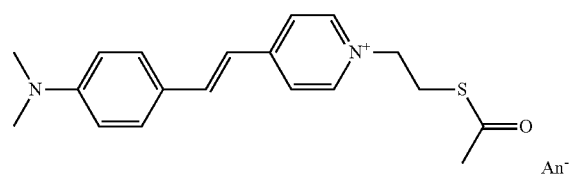 [SMILES: CC(=O)SCC[n+]1ccc(/C=C/c2ccc(N(C)C)cc2)cc1] An⁻ | 116 |
| 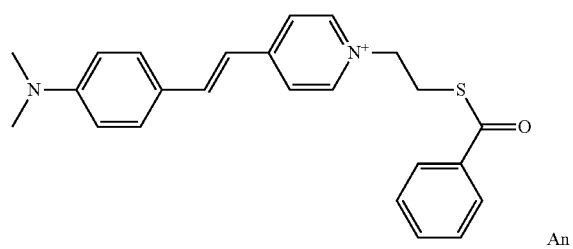 [SMILES: CN(C)c1ccc(/C=C/c2cc[n+](CCSC(=O)c3ccccc3)cc2)cc1] An⁻ | 117 |
| 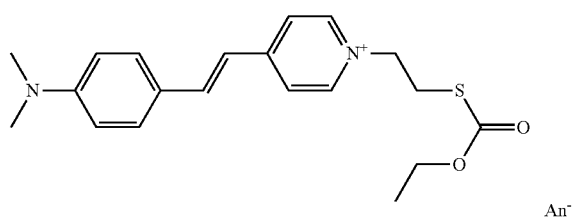 [SMILES: CCOC(=O)SCC[n+]1ccc(/C=C/c2ccc(N(C)C)cc2)cc1] An⁻ | 118 |

-continued

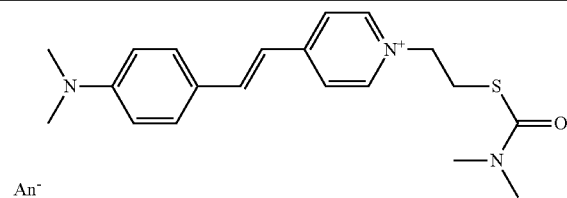

119

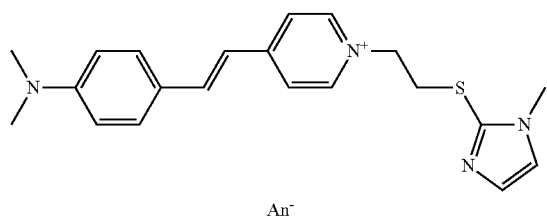

120

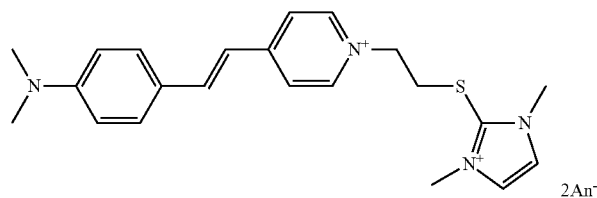

121

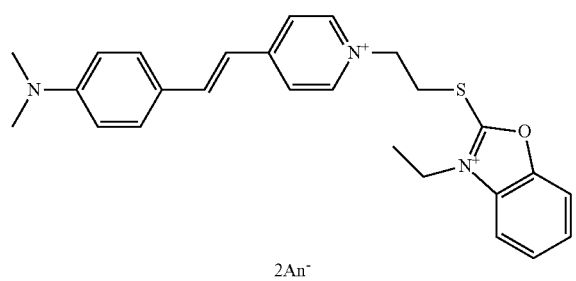 [SMILES: CC[n+]1c(SCC[n+]2ccc(/C=C/c3ccc(N(C)C)cc3)cc2)oc2ccccc21]

122

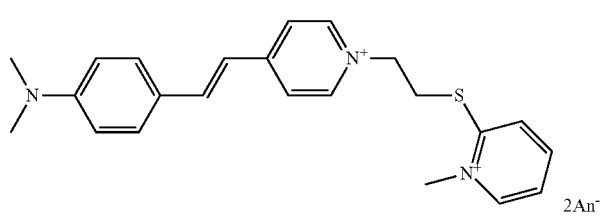 [SMILES: CN(C)c1ccc(/C=C/c2cc[n+](CCSc3cccc[n+]3C)cc2)cc1]

123 with An⁻ and M', which may be identical or different, preferentially identical, representing anionic counterions. More particularly, the anionic counterion is chosen from halides such as chloride, alkyl sulfates such as methyl sulfate, and mesylate.

1.1.5 The Cosmetically Acceptable Organic or Mineral Acid Salt of the Dyes of the Invention:

an "organic or mineral acid salt" is more particularly chosen from a salt derived from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)OH$; xiv) triflic acid $CF_3SO_3H$; and xv) tetrafluoroboric acid $HBF_4$;

an "anionic counterion" is an anion or an anionic group associated with the cationic charge of the dye; more particularly, the anionic counterion is chosen from: i) halides such as chloride or bromide; ii) nitrates; iii) sulfonates, including $C_1$-$C_6$ alkylsulfonates: Alk-S(O)$_2$O⁻ such as methanesulfonate or mesylate and ethanesulfonate; iv) arylsulfonates: Ar—S(O)$_2$O⁻ such as benzenesulfonate and toluenesulfonate or tosylate; v) citrate; vi) succinate; vii) tartrate; viii) lactate; ix) alkyl sulfates: Alk-O—S(O)O⁻ such as methyl sulfate and ethyl sulfate; x) aryl sulfates: Ar—O—S(O)O⁻ such as benzene sulfate and toluene sulfate; xi) alkoxy sulfates: Alk-O—S(O)$_2$O⁻ such as methoxy sulfate and ethoxy sulfate; xii) aryloxy sulfates: Ar—O—S(O)$_2$O$^{-1}$; xiii) phosphate; xiv) acetate; xv) triflate; and xvi) borates such as a tetrafluoroborate.

Moreover, the addition salts that may be used in the context of the invention are especially chosen from addition salts with a cosmetically acceptable base such as basifying agents as defined below, for instance alkali metal hydroxides such as sodium hydroxide, potassium hydroxide, aqueous ammonia, amines or alkanolamines.

1.2. The Composition of the Dyeing Process

The dye(s) bearing a disulfide, thiol or protected thiol function especially of formula (I) as defined previously may be applied directly to keratin fibres in powder form or may be in a liquid composition.

The dye composition that is useful then contains, in a cosmetically acceptable medium, an amount of the dyes bearing a disulfide, thiol or protected thiol function as defined previously especially of formula (I) as defined previously, generally of between 0.001% and 30% relative to the total weight of the composition.

Preferably, the amount of dyes bearing a disulfide, thiol or protected thiol function as defined previously, especially of formula (I), is between 0.01% and 5% by weight relative to the total weight of the composition. By way of example, the dye(s) are in an amount of between 0.01% and 2%.

Preferably, the composition of the dyeing and/or lightening process of the invention is in liquid form and contains one or more cationic direct dyes of formula (I) bearing a disulfide function as defined previously.

The Medium:

The medium that is suitable for dyeing, also known as the dye support, is a cosmetic medium generally formed from water or a mixture of water and one or more organic solvents or a mixture of organic solvents.

The term "organic solvent" means an organic substance capable of dissolving another substance without chemically modifying it.

1.2.1 The Organic Solvents:

Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

The solvents are preferably present in proportions preferably of between 1% and 40% by weight approximately and even more preferably between 5% and 30% by weight approximately relative to the total weight of the dye composition.

1.2.2 The Adjuvants:

The composition comprising the dye(s) bearing a disulfide, thiol or protected thiol function especially of formula (I) as defined previously of the process of the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic non-thiol and siliceous polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the dye composition in accordance with the invention are not, or are not substantially, adversely affected by the envisaged addition(s).

1.2.3 The Additional Dyes:

The composition comprising the dye(s) bearing a disulfide, thiol or protected thiol function especially of formula (I) as defined previously of the process of the invention may also contain one or more additional direct dyes other than the disulfide, thiol or protected-thiol direct dyes of formula (I) according to the invention. These direct dyes are chosen, for example, from those conventionally used in direct dyeing, and among which mention may be made of any commonly used aromatic and/or non-aromatic dye such as neutral, acidic or cationic nitrobenzene direct dyes, neutral, acidic or cationic azo direct dyes, natural direct dyes, neutral, acidic or cationic quinone and in particular anthraquinone direct dyes, azine, triarylmethane, indoamine, methine, styryl, porphyrin, metalloporphyrin, phthalocyanine, cyanine and methine direct dyes, and fluorescent dyes.

Among the natural direct dyes, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts, may also be used.

According to the invention, the additional direct dye(s) used according to the invention preferably represent from 0.001% to 10% by weight approximately relative to the total weight of the dye composition comprising the dye(s) bearing a disulfide, vinyl or protected thiol function especially of formula (I) as defined previously and even more preferentially from 0.05% to 5% by weight approximately.

The composition comprising the dye(s) bearing a disulfide, thiol or protected thiol function especially of formula (I) as defined previously of the process of the invention may also contain one or more oxidation bases and/or one or more couplers conventionally used for the dyeing of keratin fibres.

Among the oxidation bases, mention may be made of para-phenylenediamines, bis(phenyl)alkylenediamines, para-aminophenols, bis-para-aminophenols, ortho-aminophenols and heterocyclic bases, and the addition salts thereof.

Among these couplers, mention may be made especially of meta-phenylenediamines, meta-aminophenols, meta-diphenols, naphthalene-based couplers and heterocyclic couplers, and the addition salts thereof.

The coupler(s) are each generally present in an amount of between 0.001% and 10% by weight and preferably between 0.005% and 6% by weight relative to the total weight of the dye composition.

The oxidation base(s) present in the dye composition are each generally present in an amount of between 0.001% and 10% by weight and preferably between 0.005% and 6% by weight relative to the total weight of the dye composition.

In general, the addition salts of the oxidation bases and couplers used in the context of the invention are especially chosen from the salts of addition with an acid, such as the hydrochlorides, hydrobromides, sulfates, citrates, succinates, tartrates, lactates, tosylates, benzenesulfonates, phosphates and acetates, and the salts of addition with a base, such as alkali metal hydroxides, for instance sodium hydroxide, potassium hydroxide, ammonia, amines or alkanolamines.

According to one particular embodiment, the composition of the process of the invention contains at least one oxidation base and optionally at least one coupler as defined above.

The process of the invention may also use another composition that comprises one or more chemical oxidizing agents.

The term "chemical oxidizing agent" means chemical oxidizing agents other than atmospheric oxygen.

The chemical oxidizing agent may be chosen, for example, from hydrogen peroxide, urea peroxide, alkali metal bromates such as sodium bromate, persalts such as perborates and persulfates, and enzymes such as peroxidases and two-electron or four-electron oxidoreductases, for instance uricases, and four-electron oxidases such as laccases.

The use of hydrogen peroxide is particularly preferred.

The content of oxidizing agent is generally between 1% and 40% by weight relative to the weight of the composition and preferably between 1% and 20% by weight relative to the weight of the composition.

1.2.4 The pH:

The pH of the composition comprising the dye(s) bearing a disulfide, thiol or protected thiol function especially of formula (I) as defined previously according to the invention is generally between 2 and 12 approximately and preferably between 3 and 11 approximately. It may be adjusted to the desired value by means of acidifying or basifying agents usually used in the dyeing of keratin fibres, or alternatively using standard buffer systems.

The pH of the composition is preferentially between 6 and 9.

Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

Among the basifying agents, examples that may be mentioned include aqueous ammonia, alkali metal carbonates, alkanolamines such as monoethanolamine, diethanolamine and triethanolamine, and also derivatives thereof, sodium hydroxide, potassium hydroxide and the compounds of formula (a) below:

(α)

in which $W_a$ is a linear or branched, preferentially linear, divalent ($C_1$-$C_{10}$)alkylene group, optionally interrupted with one or more heteroatoms such as O, S and $NR_{a1}$ and/or optionally substituted with one or more hydroxyl groups; $R_{a1}$, $R_{a2}$, $R_{a3}$ and $R_{a4}$, which may be identical or different, represent a hydrogen atom or a $C_1$-$C_4$ alkyl or $C_1$-$C_4$ hydroxyalkyl radical; preferentially, $W_a$ represents a propylene group.

According to one particular embodiment of the invention, the dye composition contains alkaline agents including at least monoethanolamine.

1.2.5 Forms of the Composition:

The dye composition comprising the dye(s) bearing a disulfide, thiol or protected thiol function especially of formula (I) as defined previously may be in various galenical forms, such as in the form of a liquid, a lotion, a cream or a gel, or in any other form that is suitable for dyeing keratin fibres. They may also be conditioned under pressure in an aerosol can in the presence of a propellant and form a mousse.

1.3. The Mode of Application of the Dyes (I) and of the Water Vapour

A subject of the invention is a direct dyeing process that comprises i) the application to keratin materials, in particular keratin fibres such as dark hair, of one or more dyes bearing a disulfide, thiol or protected thiol function especially of formula (I) as defined previously, and ii) water vapour.

According to one particular embodiment of the invention, the step of applying or treating keratin fibres with water vapour is performed extemporaneously with that of the application or treatment of the keratin fibres with one or more dyes bearing a disulfide, thiol or protected thiol function especially of formula (I) as defined previously.

According to another particular embodiment of the process of the invention, the treatment of fibres with one or more dyes bearing a disulfide, thiol or protected thiol function especially of formula (I) as defined previously and the step of treating the keratin fibres is performed in two stages. In a first stage, the keratin fibres are treated with one or more dyes bearing a disulfide, thiol or protected thiol function especially of formula (I) as defined previously, and then, after a leave-on time, step ii) of treatment with water vapour is applied to the keratin fibres without intermediate rinsing. In particular, the dye(s) bearing a disulfide, thiol or protected thiol function especially of formula (I) as defined previously are in a dye composition as defined previously in liquid form (point 1.2). The leave-on time after application of the composition containing the dyes of formula (I) is set at between 5 minutes and 2 hours and preferentially between 15 minutes and 1 hour, such as 30 minutes.

The dye(s) bearing a disulfide, thiol or protected thiol function especially of formula (I) as defined previously may be applied directly in powder form, without adjuvant, or in pulverulent form with solid adjuvants, and then, after an optional leave-on time set at between 5 minutes and 2 hours and preferentially between 15 minutes and 1 hour, such as 30 minutes, water vapour is applied to the keratin fibres. In one variant, the water vapour is applied extemporaneously with the treatment of the keratin fibres with one or more dyes containing a disulfide, thiol or protected thiol function especially of formula (I) as defined previously, in powder form.

The application of one or more dyes bearing a disulfide, thiol or protected thiol function especially of formula (I) as defined previously is generally performed at room temperature. It may, however, be performed at temperatures ranging from 20 to 80° C. and preferentially between 20 and 60° C., and the keratin fibres are then subjected to a treatment with water vapour.

The fibres may be treated with an iron for straightening keratin fibres assisted with water vapour. These irons are those that may be obtained commercially or those of professionals.

According to the invention, the term "water vapour" means "dry" water vapour, i.e. water vapour at atmospheric pressure, originating from water in gaseous form by boiling water in liquid form, using a heating device preferably at a temperature above the boiling point of water, at a temperature that produces water vapour (temperature between 80° C. and 180° C. and preferably between 85° C. and 150° C.). The water vapour according to the invention is thus different from the saturating vapour of air at atmospheric pressure, also known as the hygrometry of the air, or air humidity.

The temperature of the water vapour is thus preferably greater than the boiling point of liquid water (100° C. at atmospheric pressure). It is thus constituted, at atmospheric pressure, solely of gaseous water; it is a dry vapour. (see, for example: http://fr.wikipedia.org/wiki/Vapeur_d'eau).

Preferably, the temperature of the water vapour at atmospheric pressure is greater than 80° C. and more particularly between 85° C. and 110° C. inclusive.

According to another embodiment of the invention, during step ii), a liquid water/water vapour mixture is applied to the keratin fibres. The latter mixture constitutes a mist. The said mixture may also contain at least one other gas such as oxygen or nitrogen, mixtures of gases such as air, or other vaporizable compounds.

The temperature of the liquid water/water vapour mixture is preferably greater than or equal to 40° C. and is more particularly between 40° C. and 75° C. approximately.

Preferably, the liquid water/water vapour mixture is placed in contact with the fibre for a time ranging from 1 second to 1 hour and more preferentially from 5 minutes to 15 minutes. Needless to say, the application of the said mixture may be repeated several times on the same fibre, each operation taking place for a time as indicated above.

The production of the liquid water/water vapour mixture used according to the invention may take place using any apparatus known per se intended for this purpose. However, according to the present invention, use is preferably made of apparatus comprising at least one water vapour generator directly connected to a hood that diffuses the liquid water/water vapour mixture onto the keratin fibres, in particular human hair. As types of apparatus, use will be made more particularly of the machine sold under the name Micromist® by the company Takara Belmont.

Another means is to arrange the keratin fibres treated beforehand with at least one dye bearing a disulfide, thiol or protected thiol function especially of formula (I) according to step i) as defined previously, over a source of water vapour such as a kettle, a boiling water container or a steam iron, for example the commercially available irons such as Joico K-Pak ReconstRx Vapor Iron and Babyliss Pro230 steam.

The treatment time of the keratin fibres with the water vapour is between 5 minutes and 2 hours and preferentially between 15 minutes and 1 hour, such as 30 minutes.

According to another process for dyeing keratin fibres, the composition that comprises at least one dye bearing a disulfide, thiol or protected thiol function especially of formula (I) as defined previously is an aqueous composition, this composition being applied to the hair followed by application of a straightening iron that generates water vapour in situ.

According to one variant of the process for dyeing keratin fibres, the composition that comprises at least one dye bearing a disulfide, thiol or protected thiol function especially of formula (I) as defined previously is applied to wet or moistened hair followed by application of a straightening iron that also generates water vapour in situ.

According to one embodiment of the process of the invention that uses one or more dyes bearing a protected thiol function especially of formula (I) as defined previously, the dyes are not deprotected beforehand. After a leave-on time on the keratin fibres as described previously, preferentially 30 minutes, the fibres are treated with water vapour preferentially for 30 minutes.

Preferentially, the process for dyeing keratin fibres does not use a reducing agent.

A treatment with a chemical oxidizing agent may optionally be combined as a post-treatment. Any type of oxidizing agent that is conventional in the field as described previously may be used. Thus, it may be chosen from hydrogen peroxide, urea peroxide, alkali metal bromates, persalts such as perborates and persulfates, and also enzymes, among which mention may be made of peroxidases, 2-electron oxidoreductases such as uricases, and 4-electron oxygenases such as laccases. The use of hydrogen peroxide is particularly preferred. The duration of the optional post-treatment with an oxidizing agent is between 1 second and 40 minutes and preferably between 1 and 10 minutes.

Preferentially, the chemical oxidizing agent(s), when they are present in the dyeing process of the invention, are in very mild concentrations, i.e. less than or equal to 5% by weight and preferentially 1% by weight relative to the total weight of the mixture comprising the dye(s) bearing a disulfide, thiol or protected thiol function especially of formula (I) as defined previously and the chemical oxidizing agent(s). According to one particular embodiment of the invention, the dyeing process does not involve any chemical oxidizing agent.

The application of the composition may be performed on dry hair or may be preceded by moistening of the hair.

According to one particular embodiment of the dyeing process, it is sought to lighten dark keratin fibres, especially with a tone depth of less than or equal to 6 and preferentially less than or equal to 4. To do this, the process for the dyeing and optical lightening of dark keratin fibres uses i) one or more dyes bearing a disulfide, thiol or protected thiol function especially of formula (I) as defined previously, which bear at least one fluorescent chromophore A and/or A' as defined previously; the step of treatment with water vapour ii) being performed either simultaneously or in a subsequent step after respecting a leave-on time between step i) and step ii) as mentioned previously.

Preferentially, the chemical oxidizing agent(s), when they are present in the lightening process according to the invention, are in very mild concentrations, i.e. less than or equal to 5% by weight and preferentially 1% by weight relative to the total weight of the mixture comprising the dye(s) bearing a disulfide, thiol or protected thiol function especially of formula (I) as defined previously and the chemical oxidizing agent(s). According to one particular embodiment of the invention, the dyeing process does not involve any chemical oxidizing agent.

In particular, the dyeing and/or lightening process of the invention that uses i) the dye(s) bearing a disulfide, thiol or protected thiol function especially of formula (I) as defined previously and ii) water vapour under conditions as presented previously is performed without using a reducing agent.

The examples that follow serve to illustrate the invention without, however, being limiting in nature.

The direct thiol, protected thiol or disulfide dyes of formula (I) that are useful in the present invention are known compounds and may be prepared according to methods known to those skilled in the art, especially from the methods described in patent applications EP 1 647 580, EP 2 004 759, WO 2007/110 541, WO 2007/110 540, WO 2007/110 539, WO 2007/110 538, WO 2007/110 537, WO 2007/110 536, WO 2007/110 535, WO 2007/110 534, WO 2007/110 533, WO 2007/110 532, WO 2007/110 531, EP 2 070 988 and WO 2009/040 354.

EXAMPLES OF DYEING

Example 1

Dyeing Process

Comparative tests of dyeing keratin fibres were performed with the following two dyes:

| Dyes | Structure of the dyes |
|---|---|
| Dye 1 (disulfide dye of the invention) | (chemical structure) |
| Dye 2 (non-disulfide dye: comparative) | (chemical structure) |

M representing a mesylate/Br counterion

Protocol 1: Application of the Dyes without a Reducing Treatment

The dye compositions were prepared with the contents of ingredients given in the table below:

| Ingredients | Composition 1 inventive | Composition 2 comparative |
|---|---|---|
| Hydroxyethylcellulose Natrosol 250MR | 0.72 g | 0.72 g |
| C8/C10 (50/50) Alkyl hydroxyethylcellulose CG 110 | 5 g | 5 g |
| Benzyl alcohol | 4 g | 4 g |
| Polyethylene glycol 400 | 4 g | 4 g |
| Dye 1 | 0.5 g | — |
| Dye 2 | — | 0.5 g |
| Sodium mesylate | 122 mg | 122 mg |
| Water | qs 100 g | qs 100 g |

Composition 1 or 2 is applied to dark hair with a tone depth of 4 at a rate of 5 g of composition per 1 g of hair, at room temperature for 30 minutes. The locks are then drained dry, and then washed with shampoo and dried under a hood for 30 minutes.

Protocol 2: Application of the Dyes with a Reducing Treatment

The dye compositions were prepared with the contents of ingredients given in the table below:

| Ingredients | Composition 3 | Composition 4 comparative |
|---|---|---|
| Hydroxyethylcellulose Natrosol 250MR | 0.72 g | 0.72 g |
| C8/C10 (50/50) Alkyl hydroxyethylcellulose CG 110 | 5 g | 5 g |
| Benzyl alcohol | 4 g | 4 g |
| Polyethylene glycol 400 | 4 g | 4 g |
| Dye 1 | 0.5 g | — |
| Dye 2 | — | 0.5 g |
| Sodium mesylate | 122 mg | 122 mg |
| L'Oréal Dulcia Vital 2-force1 ® (9% thioglycolic acid) | 5 g | 5 g |
| Water | qs 100 g | qs 100 g |

Composition 3 or 4 is prepared and immediately applied to dark hair with a tone depth of 4 at a rate of 5 g of formula per 1 g of hair, at room temperature for 30 minutes. The locks are rinsed with water, drained dry and then soaked for 5 minutes in a hydrogen peroxide solution (10 vol). The locks are then washed with shampoo and dried under a hood for 30 minutes.

Treatment with Water Vapour

The locks are held 5 cm above a bath of boiling water for 30 minutes. The locks are then drained dry, and then washed with shampoo and dried under a hood for 30 minutes.

This treatment simulates a treatment with a steam iron of the type such as Babyliss Lisseur Vapeur Pro 230 Steam®.

Shampoo Protocol

The lock is taken in the hand containing 0.4 g (/g of lock) of "Ultra doux" [Ultra mild] shampoo and the lock is passed between the fingers ten times to simulate shampooing. The lock is then rinsed with water for 15 seconds. Repetitive shampooing is performed, with drying for 30 minutes under a hood between two shampoo washes.

Measurement of the Visibility of the Coloration and of the Remanence of the Visibility After dyeing, the reflectance of the locks is measured using a Minolta CM2600d spectrocolorimeter (specular components included, angle 10°, illuminant D65) with a visible light in the wavelength range from 400 to 700 nm.

The higher the value of the reflectance at a given wavelength, the more visible will be the colour on the hair. In contrast, a reduction in the reflectance measurement indicates a reduction in the visibility of the coloration on the hair.

Results: see FIGS. 1 to 5, p. 1/3 to 3/3.

Visual Observations

During the dyeing and shampooing via protocol 2 using a reductive treatment, an unpleasant odour is noted.

The locks treated with the dyes that do not graft onto the hair have no appreciable lightening effect or any appreciable visible coloration.

An appreciable lightening effect and visible coloration are observed when the dyes are grafted onto the hair according to the invention; with Example 5 (protocol 2/dye 1—without water vapour treatment) our comparative, and also for Example 4 (protocol 1/dye 1—with water vapour treatment) according to the invention. The observed colour and the lightening effect remain visible and virtually unchanged on hair with a tone depth of 4 after five shampoo washes.

Thus, the process of the invention makes it possible to obtain lightening and remanence that are similar to or even better than those obtained when a reductive pretreatment is used, but without having to suffer the presence of an unpleasant odour associated with the treatment of the fibres. In addition, the process does not require a fixing step, i.e. the use of an additional step using a chemical oxidizing agent.

Reflectance Results

These observations corroborate the reflectance results:

Specifically, the reflectance of a lock of hair treated with a composition containing a disulfide reactive dye according to the dyeing protocols that enable grafting onto the hair is better than that of untreated hair or hair that is treated with a dye not grafted onto the hair. The locks treated via a dyeing protocol that enables grafting onto the hair thus appear lighter (Example 3 versus Example 2, and Example 4 versus Example 1).

Thus, the coloration and the lightening effect on the hair remain virtually unchanged after five shampoo washes, which indicates very good shampoo-fastness. The coloration achieved with the novel grafting protocol (Example 4) is just as fast as, or even faster than, when it is performed in the presence of a reducing agent and a chemical oxidizing agent (Example 5), but without any unpleasant odour appearing during the dyeing and the subsequent shampooing.

The invention claimed is:

1. A process for dyeing keratin fibers, comprising:
   applying to the fibers at least one cationic direct dye chosen from cationic direct dyes comprising a disulfide function and cationic direct dyes of formula (I) comprising a protected thiol function:

$$A\text{-}(X)_p\text{---}C_{sat}\text{---}S\text{---}U \quad (I)$$

and organic acid salts, mineral acid salts, optical isomers, geometric isomers, tautomers and solvates thereof, wherein in formula (I):

U is a radical chosen from $-S-C'_{sat}-(X')_{p'}\text{-}A'$;

A and A', which may be identical or different, are radicals comprising at least one cationic chromophore;

X and X', which may be identical or different, are chosen from linear and branched, saturated and unsaturated divalent $C_1$-$C_{30}$ hydrocarbon-based chains, optionally interrupted and optionally terminated at at least one end with at least one divalent group chosen from $-N(R)-$, $-N^+(R)(R)-$, $-O-$, $-S-$, $-CO-$, and $-SO_2-$ wherein R, which may be identical or different, is chosen from hydrogen $C_1$-$C_4$ alkyl radicals, hydroxyalkyl radicals, and aminoalkyl radicals; and aromatic and non-aromatic, saturated and unsaturated, fused and non-fused (hetero)cyclic radicals optionally comprising at least one identical or different, optionally substituted heteroatom;

p and p', which may be identical or different, are chosen from 0 and 1;

$C_{sat}$ and $C'_{sat}$, which may be identical or different, are chosen from optionally cyclic, optionally substituted linear and branched $C_1$-$C_{18}$ alkylene chains; and applying water vapor to the fibers;

wherein the at least one cationic direct dye and the water vapor may be applied together or separately.

2. The process according to claim 1, wherein formula (I) has the formula $A\text{-}(X)_p\text{---}C_{sat}\text{---}S\text{---}S\text{---}C'_{sat}\text{---}(X')_{p'}\text{-}A'$, wherein A equals A', X equals X', p equals p', and $C_{sat}$ equals $C'_{sat}$.

3. The process according to claim 1, wherein the cationic direct dyes of formula (I) are dyes wherein $C_{sat}$ and $C'_{sat}$, which may be identical or different, are chosen from chains $-(CH_2)_k-$ wherein k is an integer ranging from 1 to 8.

4. The process according to claim 1, wherein the cationic direct dyes of formula (I) are dyes that, when p and p' are equal to 1, X and X', which may be identical or different, are chosen from the sequence:

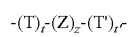

wherein the sequence is linked in formula (I) symmetrically as follows:

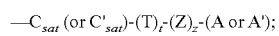

wherein:

T and T', which may be identical or different, are chosen from at least one radical chosen from: $-O-$; $-S-$; $-N(R)-$; $-N^+(R)(R°)-$; $-S(O)-$; $-S(O)_2-$; and $-C(O)-$; wherein R and R°, which may be identical or different, are chosen from hydrogen atoms, $C_1$-$C_4$ alkyl radicals, $C_1$-$C_4$ hydroxyalkyl radicals and aryl($C_1$-$C_4$)alkyl radicals; and cationic and non-cationic heterocycloalkyl and heteroaryl radicals;

t and t', which may be identical or different, are chosen from 0 and 1;

Z is chosen from:

$-(CH_2)_m-$ radicals wherein m is an integer ranging from 1 to 8;

$-(CH_2CH_2O)_q-$ and $-(OCH_2CH_2)_q-$ wherein q is an integer ranging from 1 to 5;

aryl, alkylaryl and arylalkyl radicals wherein the alkyl radical is $C_1$-$C_4$ and the aryl radical is $C_6$, being optionally substituted with at least one group $SO_3M$ wherein M is chosen from hydrogen atoms, alkali metals and ammonium groups substituted with at least one identical or different, linear or branched $C_1$-$C_{18}$ alkyl radical optionally comprising at least one hydroxyl; and z is chosen from 0 and 1.

5. The process according to claim 1, wherein the cationic direct dyes of formula (I) comprises at least one chromophore chosen from A and A', which may be identical or different, derived from the following dyes: poly(azos), hydrazono and hydrazones; azomethines; cyanins; (poly)methines; and naphthalimides.

6. The process according to claim 1, wherein the cationic direct dyes of formula (I) comprise at least one of chromophores A and A', which may be identical or different, chosen from the cationic hydrazono chromophores of formulae (II), (II'), (III), and (III'), the azo cationic chromophores (IV) and (IV') and the diazo cationic chromophores (V) and (V'):

$$(*)\text{-Het}^+\text{-C(R}^a\text{)}=N-N(R^b)-Ar,Q^- \quad (II)$$

$$Q^-,\text{Het}^+\text{-C(R}^a\text{)}=N-N(R^b)-Ar'\text{-}(*), \quad (II')$$

$$(*)\text{-Het}^+\text{-N(R}^a\text{)}-N=C(R^b)-Ar,Q^- \quad (III)$$

$$Q^-,\text{Het}^+\text{-N(R}^a\text{)}-N=C(R^b)-Ar'\text{-}(*), \quad (III')$$

$$(*)\text{-Het}^+\text{-N}=N-Ar,Q^- \quad (IV)$$

$$Q^-,\text{Het}^+\text{-N}=N-Ar'\text{-}(*), \quad (IV')$$

$$(*)-Ar^+-N=N-Ar'',Q^- \quad (V)$$

$$Q^-,Ar^+-N=N-Ar''\text{-}(*) \quad (V')$$

wherein
Het$^+$ is a cationic heteroaryl radical;
Ar$^+$ is an aryl radical comprising an exocyclic cationic charge;
Ar is an optionally substituted aryl group;
Ar' is an optionally substituted divalent (hetero)arylene group;
Ar'' is an optionally substituted (hetero)aryl group;
R$^a$ and R$^b$, which may be identical or different, are chosen from hydrogen atoms and optionally substituted (C$_1$-C$_8$) alkyl groups;
or alternatively the substituent R$^a$ with a substituent of at least one of Het$^+$ and R$^b$ with a substituent of Ar form, together with the atoms to which they are attached, a (hetero)cycloalkyl;
Q$^-$ is chosen from organic and mineral anionic counterions; and
(*) represents the part of the chromophore linked to the rest of the molecule of formula (I).

7. The process according to claim 1, wherein the cationic direct dyes of formula (I) comprise at least one of chromophores A and A', which may be identical or different, chosen from the chromophores:

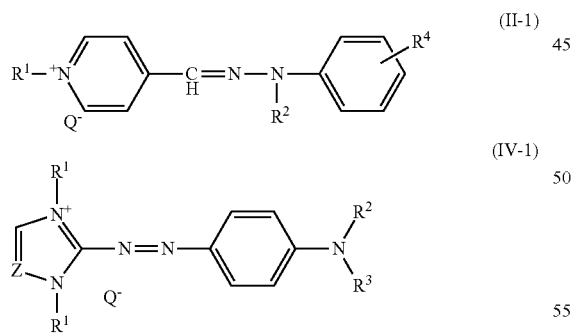

wherein
R$^1$ is a (C$_1$-C$_4$)alkyl group;
R$^2$ and R$^3$, which may be identical or different, are chosen from hydrogen atoms and (C$_1$-C$_4$)alkyl groups;
R$^4$ is chosen from hydrogen atoms and electron-donating groups;
Z is chosen from CH and nitrogen atoms;
Q$^-$ is chosen from organic and mineral anionic counterions;

wherein the chromophores (II-1) or (IV-1) are linked to the rest of the molecule of formula (I) by R$^2$, R$^1$ or R$^4$ wherein one of the hydrogen atoms of R$^2$, R$^1$ or R$^4$ is substituted with X or X' if p or p' is 1 or alternatively with C$_{sat}$ or C$_{sat'}$ if p or p' is 0.

8. The process according to claim 7, wherein the chromophores (II-1) and (IV-1) are derived from the dyes:

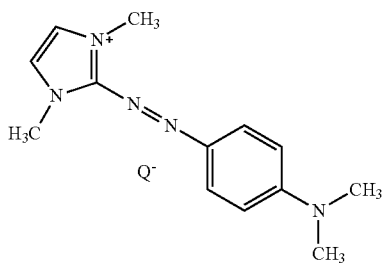

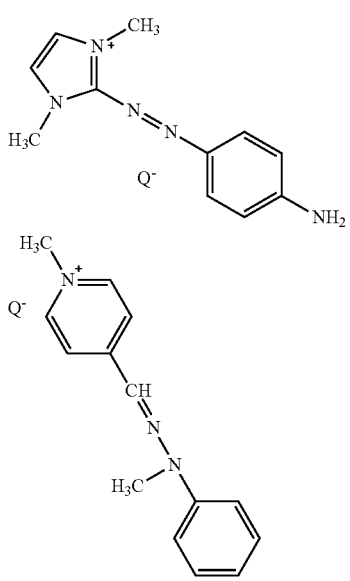

wherein Q' is an anionic counterion.

9. The process according to claim 1, wherein the cationic direct dyes of formula (I) comprise at least one of cationic chromophores A and A' comprising at least one quaternary ammonium radical chosen from:

a) the polymethine radicals of formulae (VI) and (VI'):

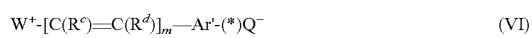

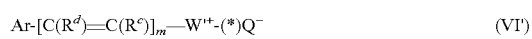

wherein:
W$^+$ is chosen from cationic heterocyclic and heteroaryl groups;
W$^+$ is chosen from divalent heterocyclic and heteroaryl radicals;
Ar is an optionally substituted aryl group;
Ar' is a divalent optionally substituted aryl radical;
m' is an integer ranging 1 to 4;

$R^c$, $R^d$, which may be identical or different, are chosen from hydrogen atoms and optionally substituted ($C_1$-$C_8$)alkyl groups, or alternatively at least one of $R^c$ contiguous with $W^+$ or $W'^+$ and $R^d$ contiguous with Ar or Ar' form, with the atoms to which they are attached, a (hetero)cycloalkyl;

$Q^-$ is an anionic counterion;

(*) represents the part of the chromophore linked to the rest of formula (I); and b) the naphthalimidyl radicals of formula (VII) and (VII') below:

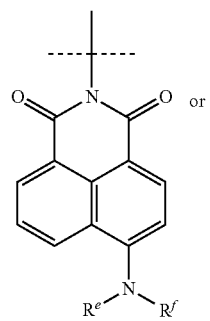
(VII)

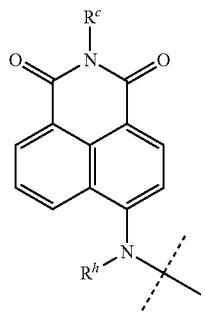
(VII')

with † representing the bond with the group X or X', $C_{sat}$ or $C'_{sat}$ wherein $R^e$, $R^f$, $R^g$ and $R^h$, which may be identical or different, are chosen from hydrogen atoms and optionally substituted $C_1$-$C_6$ alkyl groups.

10. The process according to claim 1, wherein the cationic direct dyes of formula (I) are disulfide dyes chosen from formulae (VIII) to (XIV):

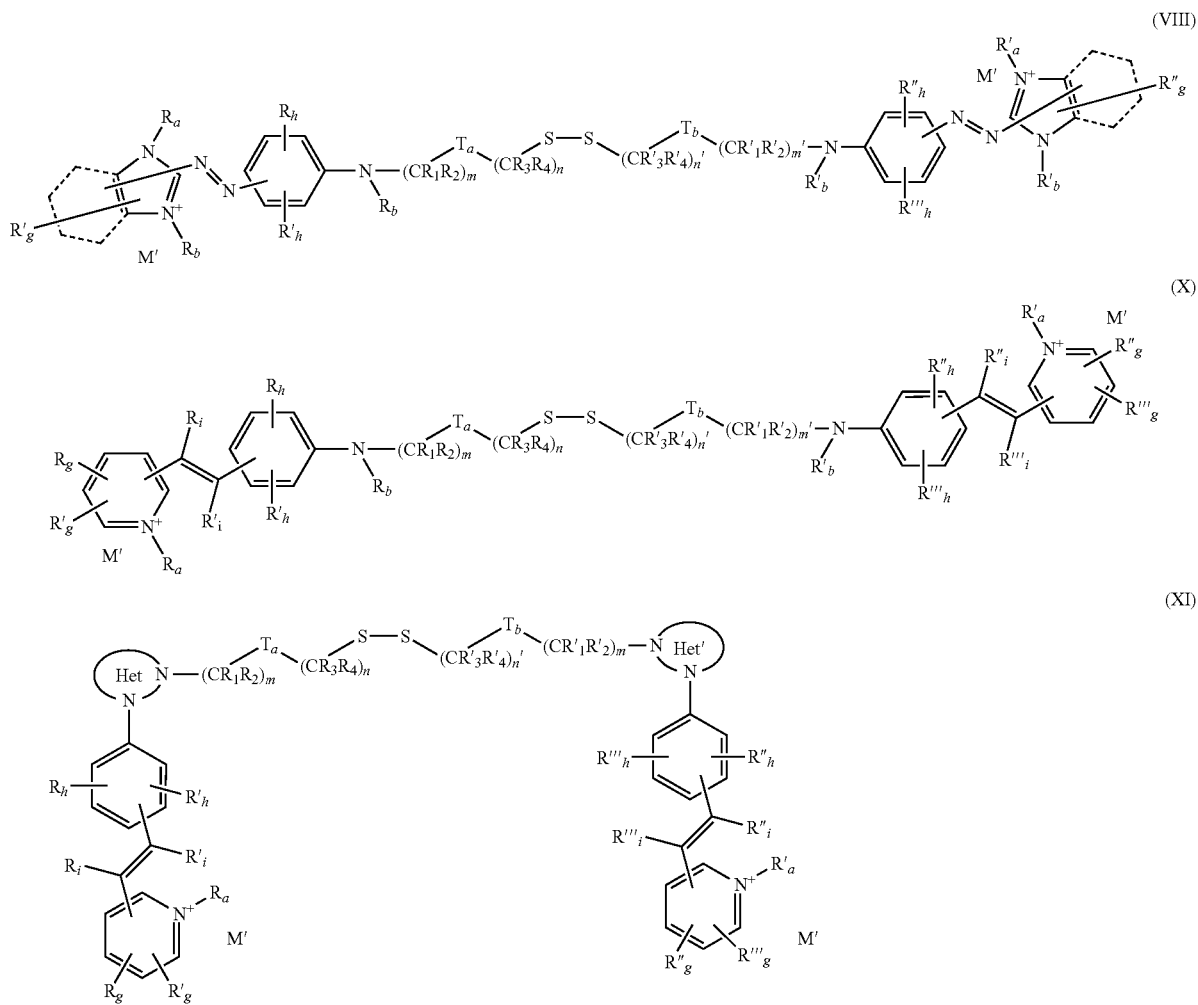

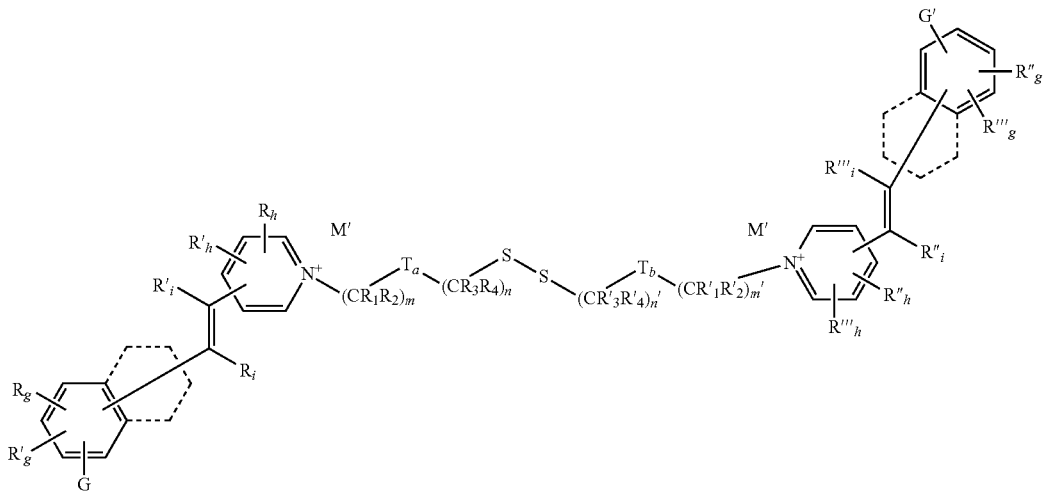

(XII)

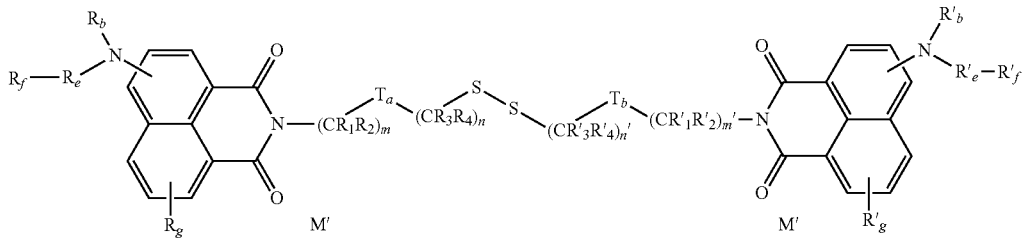

(XIII)

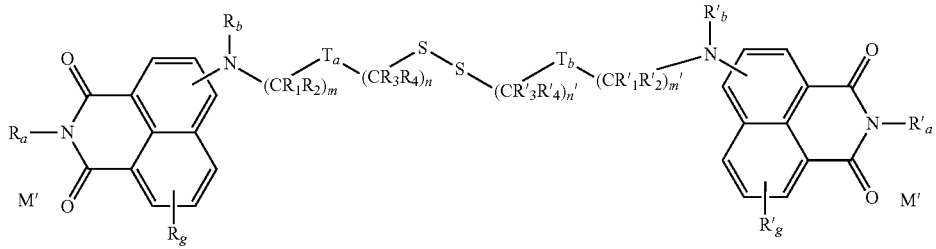

(XIV)

wherein
- G and G', which may be identical or different, are chosen from groups —NR$_c$R$_d$, —NR'$_c$R'$_d$ and C$_1$-C$_6$ alkoxy which is optionally substituted;
- R$_a$ and R'$_a$, which may be identical or different, are chosen from aryl(C$_1$-C$_4$)alkyl groups and C$_1$-C$_6$ alkyl groups optionally substituted with a hydroxyl or amino; C$_1$-C$_4$ alkylamino groups, and C$_1$-C$_4$ dialkyl amino groups, the alkyl groups optionally form, together with the nitrogen atom to which they are attached, a 5- to 7-membered heterocycle, optionally comprising a nitrogen or non-nitrogen heteroatom;
- R$_b$ and R'$_b$, which may be identical or different, are chosen from hydrogen atoms, aryl(C$_1$-C$_4$)alkyl groups and C$_1$-C$_6$ alkyl groups that are optionally substituted;
- R$_c$, R'$_c$, R$_d$ and R'$_d$, which may be identical or different, are chosen from hydrogen atoms, aryl(C$_1$-C$_4$)alkyl groups, C$_1$-C$_6$ alkoxy groups, and C$_1$-C$_6$ alkyl groups that are optionally substituted;
- or alternatively two adjacent radicals R$_c$ and R$_d$, R'$_c$ and R'$_d$ borne by the same nitrogen atom, together form a heterocyclic or heteroaryl group;
- R$_e$ and R'$_e$, which may be identical or different, are chosen from linear and branched, optionally unsaturated divalent C$_1$-C$_6$ alkylenyl hydrocarbon-based chains;
- R$_f$ and R'$_f$, which may be identical or different, are chosen from di(C$_1$-C$_4$)alkylamino groups, (R")(R''')N— groups, and quaternary ammonium groups (R")(R''') (R"")N$^+$—, wherein R", R''' and R"", which may be identical or different, are chosen from hydrogen atoms and C$_1$-C$_4$ alkyl groups, or alternatively (R")(R''')(R"") N$^+$— represents an optionally substituted cationic heteroaryl group;

$R_g$, $R'_g$, $R''_g$, $R'''_g$, $R_h$, $R'_h$, $R''_h$ and $R'''_h$, which may be identical or different, are chosen from hydrogen atoms, halogen atoms, amino radicals, $C_1$-$C_4$ alkylamino radicals, $C_1$-$C_4$ dialkylamino radicals, cyano radicals, carboxyl radicals, hydroxyl radicals, trifluoromethyl radicals, acylamino radicals, $C_1$-$C_4$ alkoxy radicals, (poly)hydroxy($C_2$-$C_4$)alkoxy radicals, alkylcarbonyloxy radicals, alkoxycarbonyl radicals, alkylcarbonylamino radicals, acylamino radicals, carbamoyl radicals, alkylsulfonylamino radicals, aminosulfonyl radical radicals, $C_1$-$C_{16}$ alkyl radicals optionally substituted with a group chosen from $C_1$-$C_{12}$ alkoxy radicals, hydroxyl radicals, cyano radicals, carboxyl radicals, amino radicals, $C_1$-$C_4$ alkylamino radicals and $C_1$-$C_4$ dialkylamino radicals, or alternatively two alkyl radicals borne by the nitrogen atom of the amino group form a 5- to 7-membered heterocycle optionally comprising another nitrogen or non-nitrogen heteroatom;

or alternatively two groups chosen from $R_g$ and $R'_g$; $R''_g$ and $R'''_g$; $R_h$ and $R'_h$; $R''_h$ and $R'''_h$ borne by two adjacent carbon atoms together form a group chosen from benzo rings, indeno rings, fused heterocycloalkyl groups, and fused heteroaryl groups; wherein the benzo, indeno, heterocycloalkyl and heteroaryl rings are optionally substituted with a radical chosen from halogen atoms, amino radicals, $C_1$-$C_4$ alkylamino radicals, $C_1$-$C_4$ dialkylamino radicals, nitro radicals, cyano radicals, carboxyl radicals, hydroxyl radicals, trifluoromethyl radicals, acylamino radicals, $C_1$-$C_4$ alkoxy radicals, (poly)hydroxy($C_2$-$C_4$)alkoxy radicals, alkylcarbonyloxy radicals, alkoxycarbonyl radicals alkylcarbonylamino radicals, acylamino radicals, carbamoyl radicals, alkylsulfonylamino radicals, aminosulfonyl radicals, and $C_1$-$C_{16}$ alkyl radicals optionally substituted with a group chosen from $C_1$-$C_{12}$ alkoxy groups, hydroxyl groups, cyano groups, carboxyl groups, amino groups, $C_1$-$C_4$ alkylamino groups, $C_1$-$C_4$ dialkylamino groups, or alternatively two alkyl radicals borne by the nitrogen atom of the amino group form a 5- to 7-membered heterocycle optionally comprising another nitrogen or non-nitrogen heteroatom;

or alternatively two groups chosen from $R_i$ and $R_g$; $R'''_i$ and $R'''_g$; $R'_i$ and $R'_h$; and $R''_i$ and $R''_h$ together form a fused (hetero)cycloalkyl;

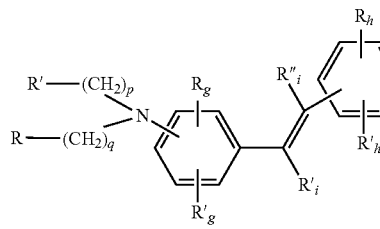

or alternatively when G is $-NR_cR_d$ and G' is $-NR'_cR'_d$, two groups chosen from $R_c$ and $R'_g$; $R'_c$ and $R''_g$; $R_d$ and $R_g$; $R'_d$ and $R'''_g$ together form a saturated heteroaryl or heterocycle, optionally substituted with at least one group ($C_1$-$C_6$)alkyl;

$R_i$, $R'_i$, $R''_i$, and $R'''_i$, which may be identical or different, are chosen from hydrogen atoms and $C_1$-$C_4$ alkyl groups;

$R_1$, $R_2$, $R_3$, $R_4$, $R'_1$, $R'_2$, $R'_3$ and $R'_4$, which may be identical or different, are chosen from hydrogen atoms $C_1$-$C_4$ alkyl radicals, $C_1$-$C_{12}$ alkoxy radicals, hydroxyl radicals, cyano radicals, carboxyl radicals, amino radicals, $C_1$-$C_4$ alkylamino radicals and $C_1$-$C_4$ dialkyl amino radicals, wherein the alkyl radicals optionally form, with the nitrogen atom to which they are attached, a 5- to 7-membered heterocycle optionally comprising a nitrogen or non-nitrogen heteroatom;

$T_a$ and $T_b$, which may be identical or different, are chosen from i) covalent σ bonds, ii) at least one radical chosen from $-SO_2-$, $-O-$, $-S-$, $-N(R)-$, $-N^+(R)(R^\circ)-$, $-CO-$, and aryl($C_1$-$C_4$)alkyls, wherein R and $R^\circ$, which may be identical or different, are chosen form hydrogen atoms, $C_1$-$C_4$ alkyls and $C_1$-$C_4$ hydroxyalkyl radicals, and iii) cationic and non-cationic, heterocycloalkyl and heteroaryl radicals;

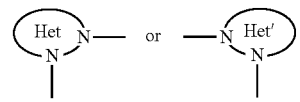

which may be identical or different, are chosen from optionally substituted heterocyclic groups;

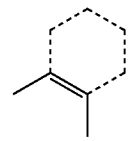

is chosen from aryl and heteroaryl groups fused to the imidazolium or phenyl ring; or alternatively is absent from the imidazolium or phenyl ring;

m, m', n and n', which may be identical or different, are integers ranging from 0 to 6, wherein m+n and m'+n' is an integer ranging from 1 to 10;

M' is an anionic counterion.

11. The process according to claim 1, wherein the cationic direct dyes of formula (I) are fluorescent dyes chosen from the dyes of formulae (XV):

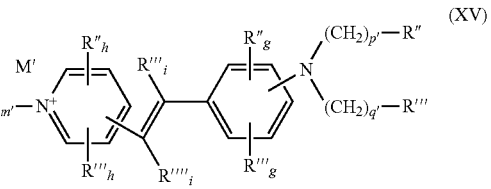

wherein

R and R''', which may be identical or different, are chosen from hydroxyl groups, amino groups ($NR_aR_b$) and ammonium groups ($N^+R_aR_bR_c$), $An^-$, wherein $R_a$, $R_b$ and $R_c$, which may be identical or different, are chosen from hydrogen atoms and ($C_1$-$C_4$)alkyl groups and $An^-$ is an anionic counterion; or alternatively two alkyl groups $R_a$ and $R_b$ of the amino or ammonium group form a 5- to 7-membered heterocycle optionally comprising a nitrogen or non-nitrogen heteroatom;

R' and R", which may be identical or different, are chosen from hydrogen atoms and groups R and R'";

$R_g$, $R'_g$, $R''_g$, $R'''_g$, $R_h$, $R'_h$, $R''_h$ and $R'''_h$, which may be identical or different, are chosen from hydrogen atoms, halogen atoms, amino groups, di($C_1$-$C_4$)alkylamino groups, cyano groups, carboxyl groups, hydroxyl groups, trifluoromethyl groups, acylamino groups, $C_1$-$C_4$ alkoxy groups, (poly)hydroxy($C_2$-$C_4$)alkoxy groups, ($C_1$-$C_4$)alkylcarbonyloxy groups, ($C_1$-$C_4$) alkoxycarbonyl groups, ($C_1$-$C_4$)alkylcarbonylamino groups, acylamino groups, carbamoyl groups, ($C_1$-$C_4$) alkylsulfonylamino groups, aminosulfonyl groups, and $C_1$-$C_{16}$ alkyl radicals optionally substituted with a group chosen from $C_1$-$C_{12}$ alkoxy, hydroxyl, cyano, carboxyl, amino and di($C_1$-$C_4$)alkylamino, or alternatively two alkyl radicals borne by the nitrogen atom of the amino group form a 5- to 7-membered heterocycle optionally comprising a nitrogen or non-nitrogen heteroatom;

$R'_i$, $R''_i$, $R'''_i$, and $R''''_i$, which may be identical or different, are chosen from hydrogen atoms and ($C_1$-$C_4$)alkyl groups;

m and m', which may be identical or different, are chosen from integers ranging from 1 to 10;

p, p', q and q', which may be identical or different, are chosen from integers ranging from 1 to 6;

M' is an anionic counterion wherein when the compounds of formula (XV) contain other cationic parts, they are combined with at least one anionic counterion that affords formula (XV) electrical neutrality; and the dyes of formulae (XVI) below:

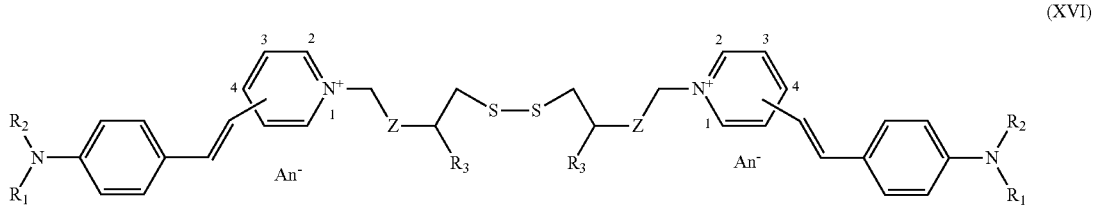

(XVI)

wherein $R_1$ chosen from $C_1$-$C_6$ alkyl groups substituted with at least one hydroxyl group and —C(O)OR' wherein R' is chosen from hydrogen atoms, $C_1$-$C_4$ alkyl groups and —C(O)—O⁻ groups and wherein, when $R_1$ is a —C(O)—O⁻ group, an anionic counterion An⁻ is absent;

$R_2$ is a $C_1$-$C_6$ alkyl group optionally substituted with at least one hydroxyl group; or alternatively the groups $R_1$ and $R_2$ form, together with the nitrogen atom to which they are attached, a saturated heterocyclic radical substituted with at least one of hydroxyl, (poly)hydroxy($C_1$-$C_4$)alkyl and —C(O)OR' groups wherein R' is chosen from hydrogen atoms, $C_1$-$C_4$ alkyl groups and —C(O)—O⁻ groups, and, when $R_1$ is a —C(O)—O⁻ group, an anionic counterion An⁻ is absent;

$R_3$ is chosen from hydrogen atoms and —C(O)OR" groups wherein R" is chosen from hydrogen atoms, alkali metals and $C_1$-$C_6$ alkyl groups, or alternatively $R_3$ is a —C(O)—O⁻ groups and, when $R_1$ is a —C(O)—O⁻ group, an anionic counterion An⁻ is absent;

Z is chosen from divalent amido groups —C(O)—N(R)— and —N(R)—C(O)—, divalent $C_1$-$C_{10}$ alkylene groups interrupted with an amido group —C(O)—N(R)—, and divalent $C_1$-$C_{10}$ alkylene groups interrupted with an amido group —N(R)—C(O)— wherein R is chosen from hydrogen atoms and $C_1$-$C_6$ alkyl groups;

An⁻ is an anionic counterion;

wherein when the compounds of formula (XVI) contain other cationic parts, they are combined with at least one anionic counterion that affords formula (XVI) electrical neutrality.

12. The process according to claim 1, wherein the cationic direct dyes of formula (I) are chosen from the chemical structures:

| 103 | 104 |
|---|---|
| 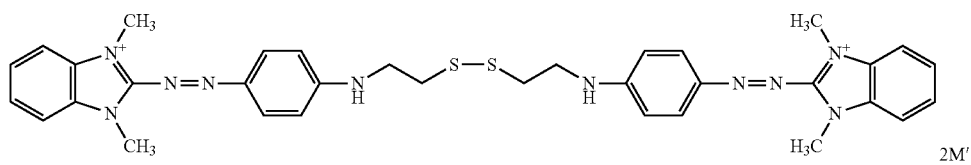 [SMILES: Cn1c(N=Nc2ccc(NCCSSCCNc3ccc(N=Nc4n(C)c5ccccc5[n+]4C)cc3)cc2)[n+](C)c2ccccc21] | 1 2M' |
| 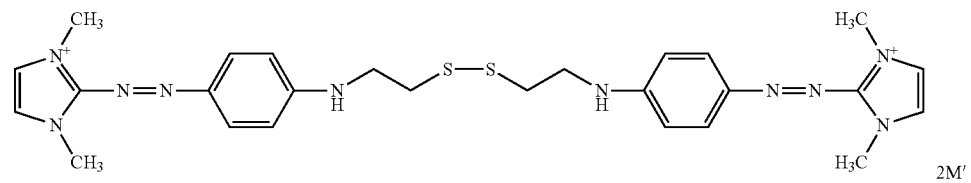 [SMILES: Cn1cc[n+](C)c1N=Nc1ccc(NCCSSCCNc2ccc(N=Nc3n(C)cc[n+]3C)cc2)cc1] | 2 2M' |
| 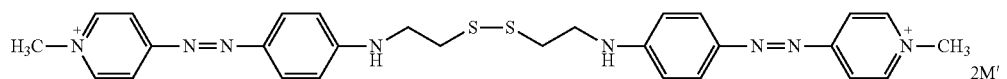 | 3 2M' |
| 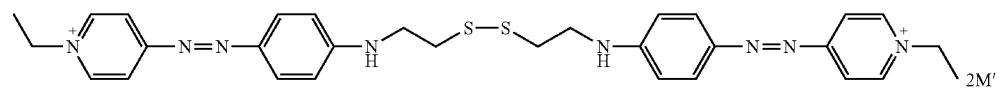 | 4 2M' |
| 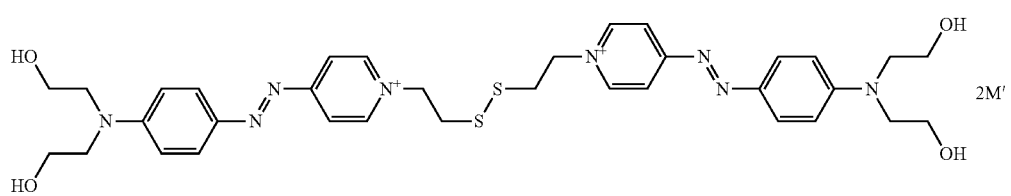 [SMILES: OCCN(CCO)c1ccc(/N=N/c2cc[n+](CCSSCC[n+]3ccc(/N=N/c4ccc(N(CCO)CCO)cc4)cc3)cc2)cc1] | 5 2M' |
| 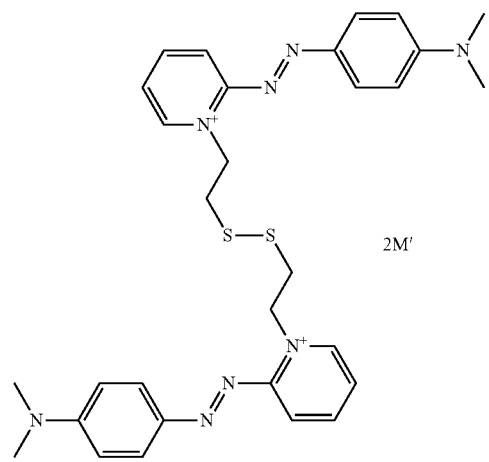 | 6 2M' |
| 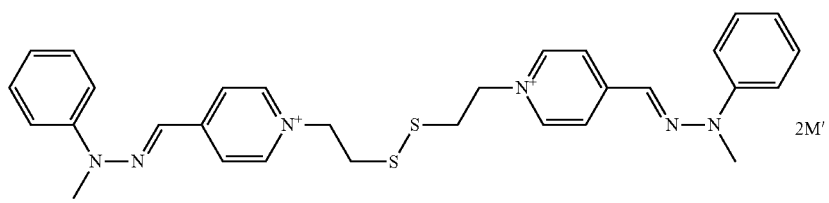 [SMILES: CN(/N=C/c1cc[n+](CCSSCC[n+]2ccc(/C=N/N(C)c3ccccc3)cc2)cc1)c1ccccc1] | 7 2M' |
| 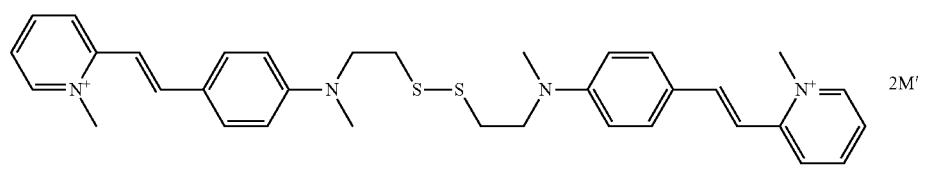 [SMILES: CN(CCSSCCN(C)c1ccc(/C=C/c2cccc[n+]2C)cc1)c1ccc(/C=C/c2cccc[n+]2C)cc1] | 8 2M' |

-continued
| | |
|---|---|
| 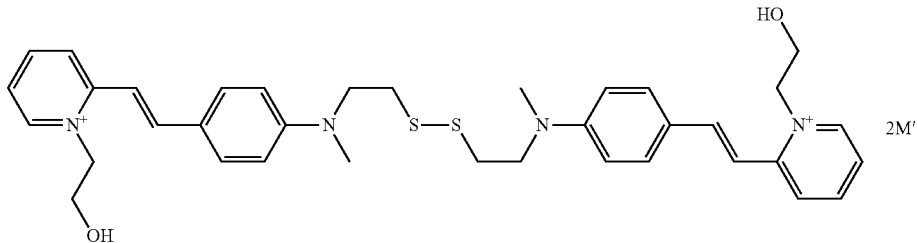 [SMILES: CN(CCSSCCN(C)c1ccc(/C=C/c2cccc[n+]2CCO)cc1)c1ccc(/C=C/c2cccc[n+]2CCO)cc1] | 9 2M' |
| 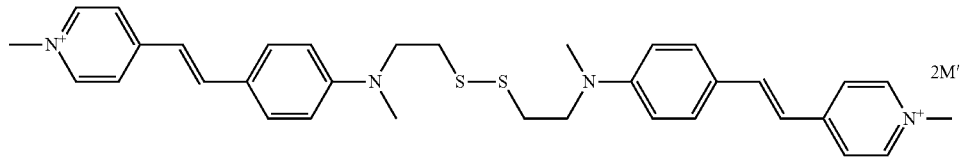 | 10 2M' |
| 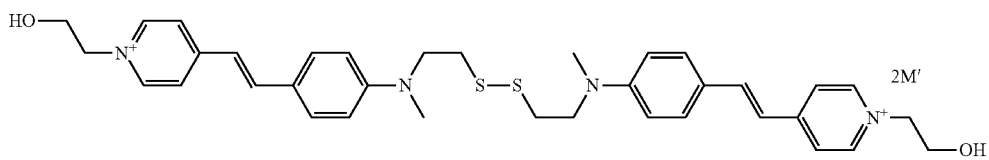 | 11 2M' |
| 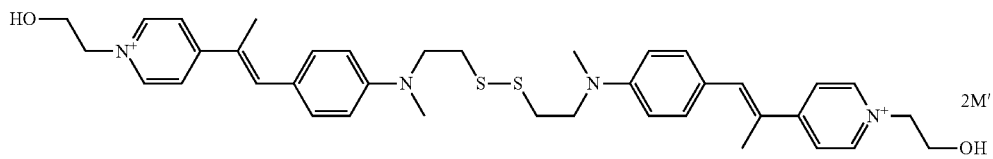 | 12 2M' |
| 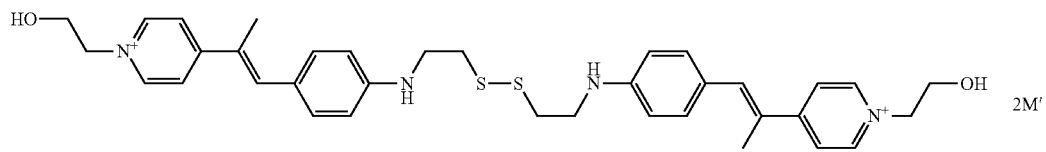 [SMILES: C/C(=C\c1ccc(NCCSSCCNc2ccc(/C=C(\C)c3cc[n+](CCO)cc3)cc2)cc1)c1cc[n+](CCO)cc1] | 13 2M' |
| 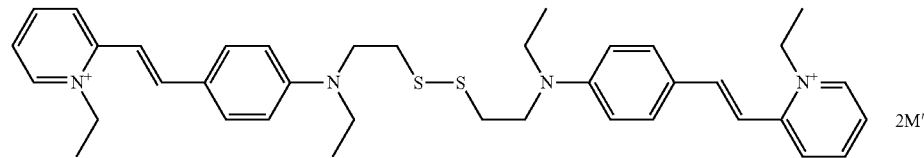 [SMILES: CCN(CCSSCCN(CC)c1ccc(/C=C/c2cccc[n+]2CC)cc1)c1ccc(/C=C/c2cccc[n+]2CC)cc1] | 14 2M' |
| 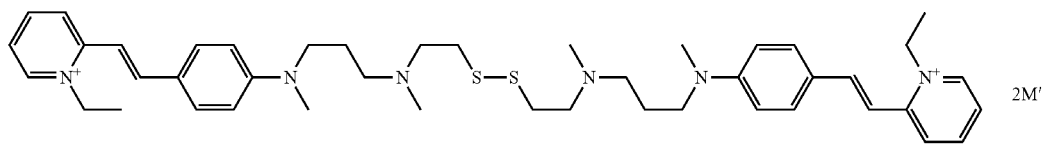 [SMILES: CC[n+]1ccccc1/C=C/c1ccc(N(C)CCCN(C)CCSSCCN(C)CCCN(C)c2ccc(/C=C/c3cccc[n+]3CC)cc2)cc1] | 15 2M' |
| 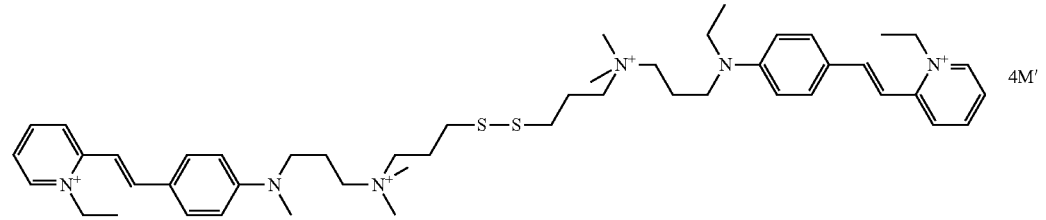 [SMILES: CCN(CCC[N+](C)(C)CCCSSCCC[N+](C)(C)CCCN(C)c1ccc(/C=C/c2cccc[n+]2CC)cc1)c1ccc(/C=C/c2cccc[n+]2CC)cc1] | 16 4M' |
| 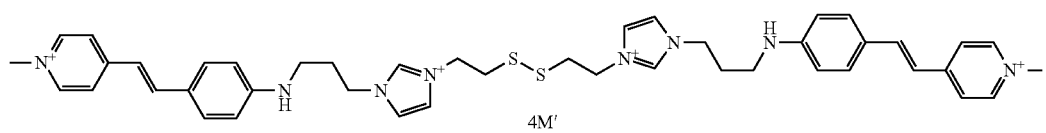 | 17 4M' |

-continued
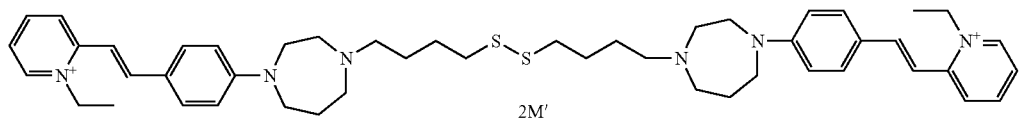 [SMILES: CC[n+]1ccccc1/C=C/c1ccc(N2CCCN(CCCCSSCCCCN3CCCN(c4ccc(/C=C/c5cccc[n+]5CC)cc4)CC3)CC2)cc1]
18
2M'
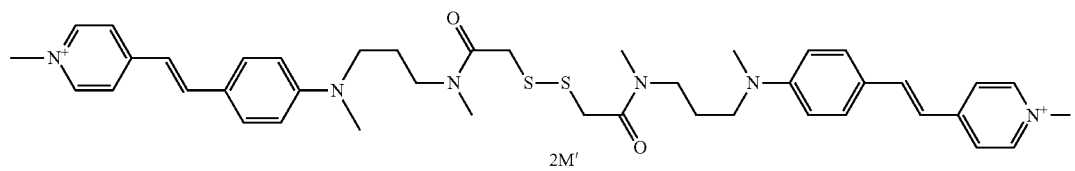
19
2M'
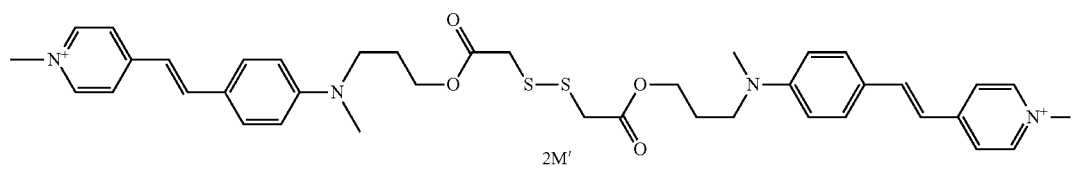
20
2M'
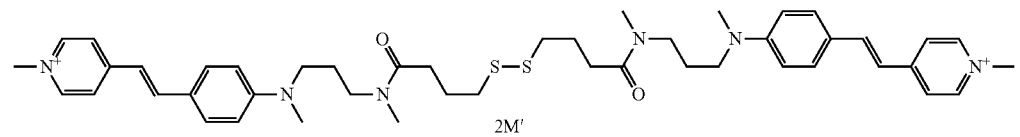
21
2M'
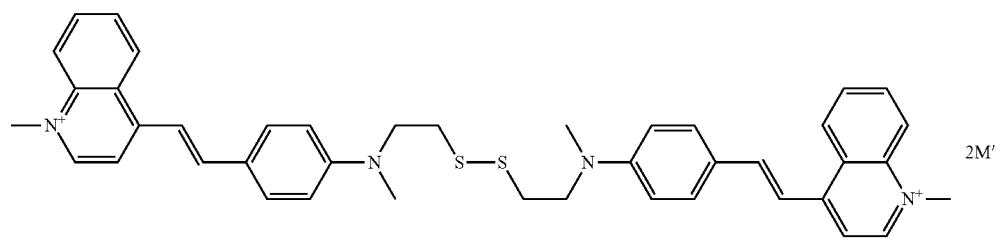
22
2M'
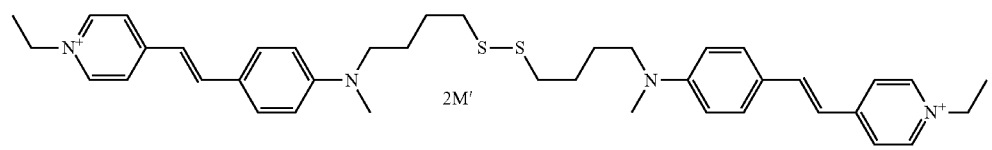 [SMILES: CC[n+]1ccc(/C=C/c2ccc(N(C)CCCCSSCCCCN(C)c3ccc(/C=C/c4cc[n+](CC)cc4)cc3)cc2)cc1]
23
2M'
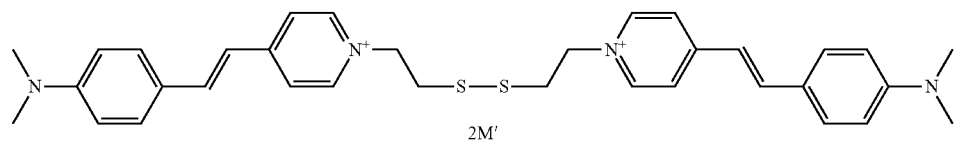
24
2M'
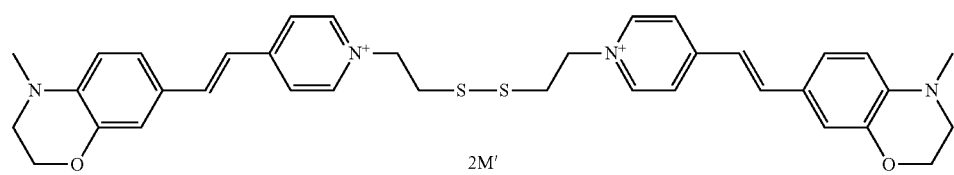
25
2M'
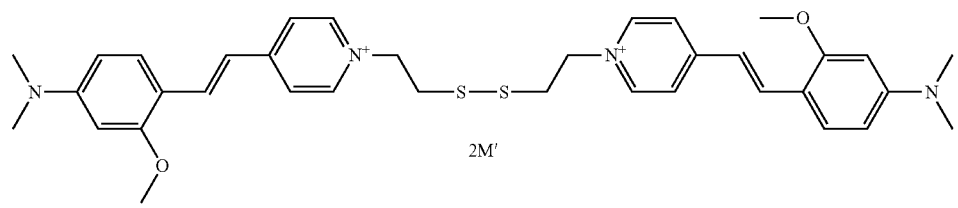
26
2M'

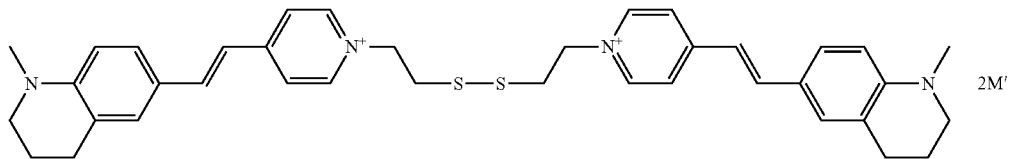 [SMILES: CN1CCCc2cc(/C=C/c3cc[n+](CCSSCC[n+]4ccc(/C=C/c5ccc6c(c5)CCCN6C)cc4)cc3)ccc21]
27  2M'
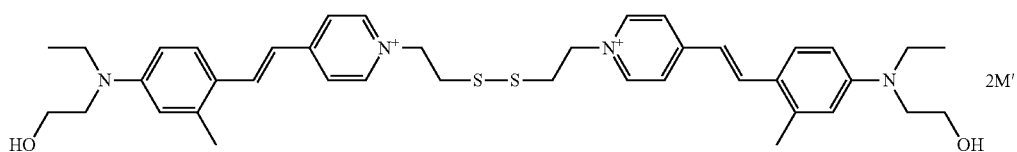 [SMILES: CCN(CCO)c1ccc(/C=C/c2cc[n+](CCSSCC[n+]3ccc(/C=C/c4ccc(N(CC)CCO)cc4C)cc3)cc2)c(C)c1]
28  2M'
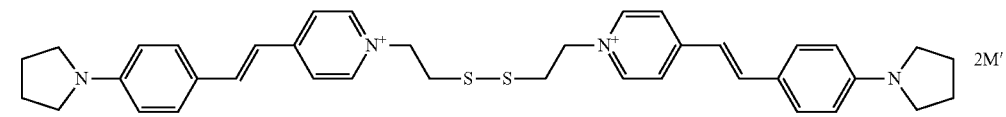
29  2M'
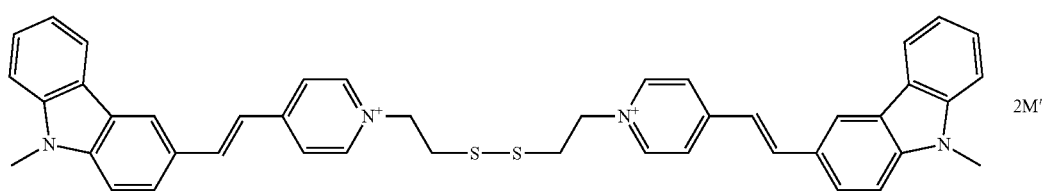 [SMILES: Cn1c2ccccc2c2cc(/C=C/c3cc[n+](CCSSCC[n+]4ccc(/C=C/c5ccc6c(c5)c5ccccc5n6C)cc4)cc3)ccc21]
30  2M'
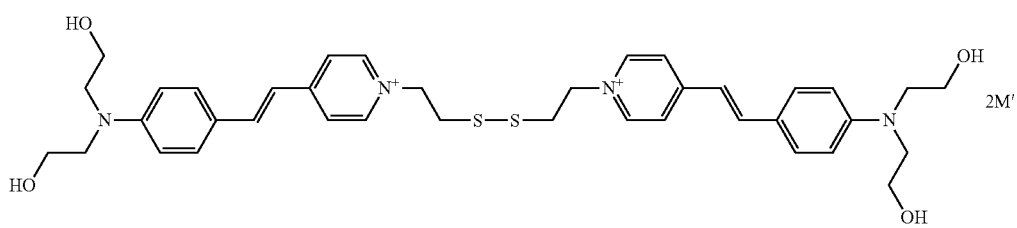 [SMILES: OCCN(CCO)c1ccc(/C=C/c2cc[n+](CCSSCC[n+]3ccc(/C=C/c4ccc(N(CCO)CCO)cc4)cc3)cc2)cc1]
31  2M'
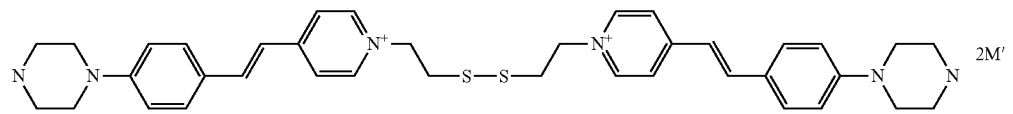
32  2M'
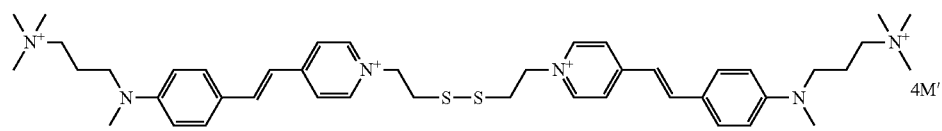
33  4M'
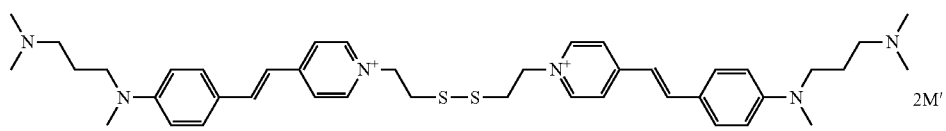
34  2M'
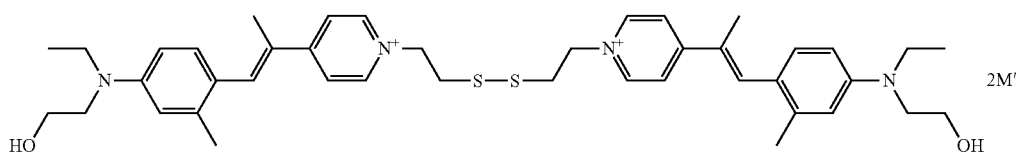 [SMILES: CCN(CCO)c1ccc(/C=C(\C)c2cc[n+](CCSSCC[n+]3ccc(/C(C)=C/c4ccc(N(CC)CCO)cc4C)cc3)cc2)c(C)c1]
35  2M'

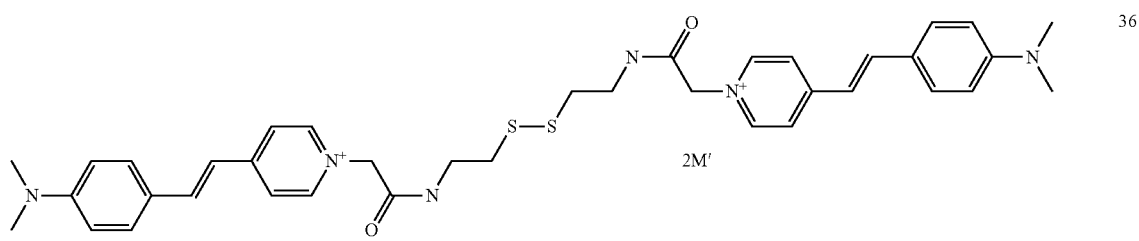
36
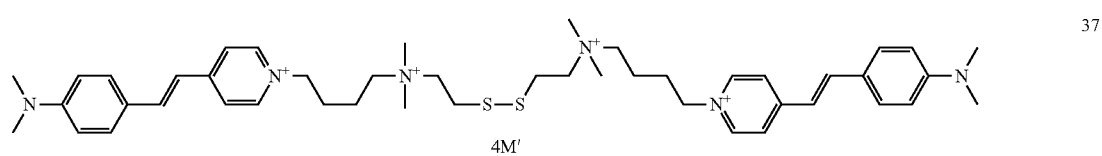
37
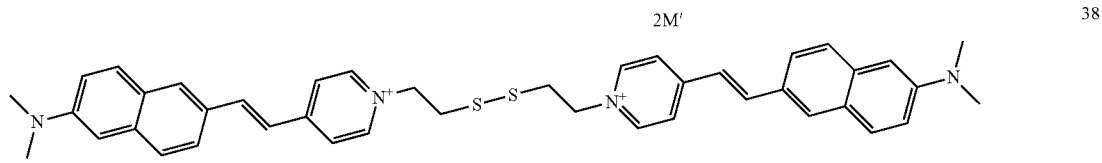
38
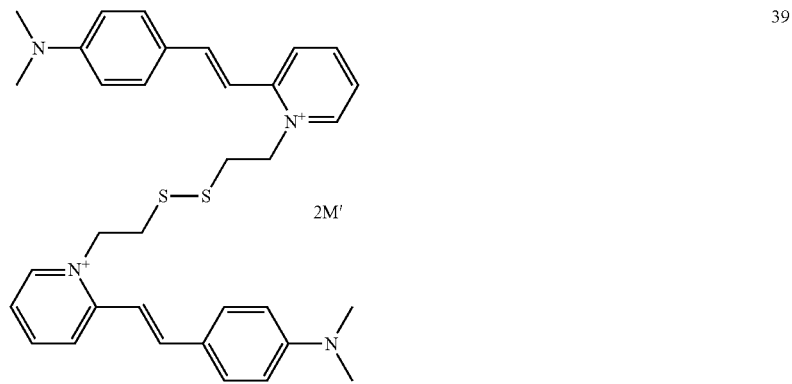
39
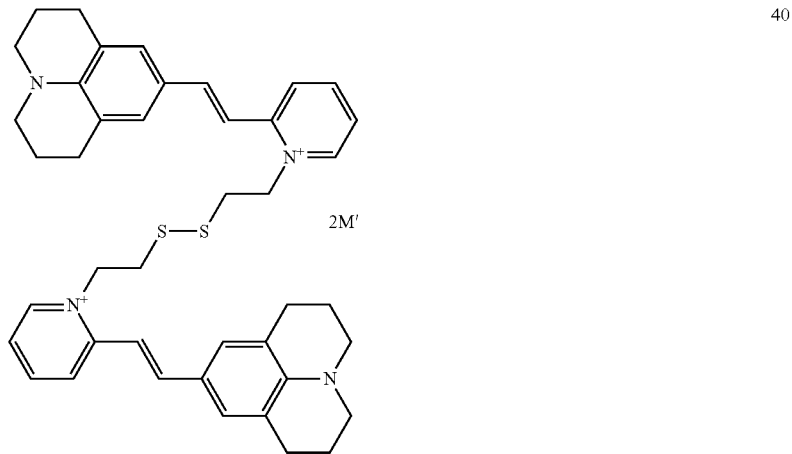
40

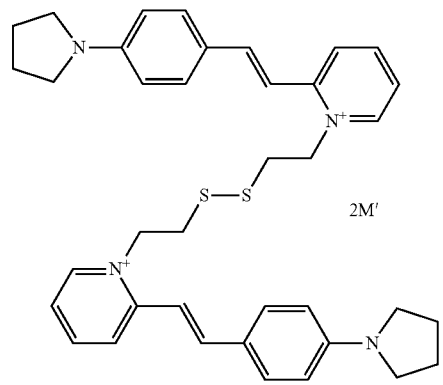 [SMILES: C(=C\c1cccc[n+]1CCSSCC[n+]1ccccc1/C=C/c1ccc(N2CCCC2)cc1)/c1ccc(N2CCCC2)cc1]
41
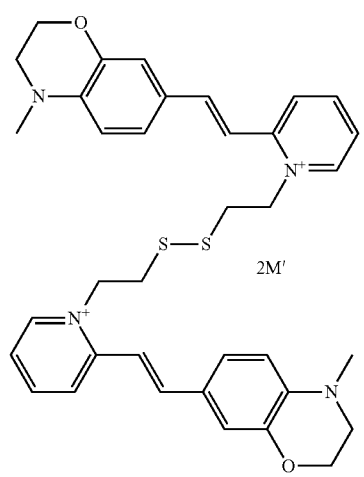 [SMILES: CN1CCOc2cc(/C=C/c3cccc[n+]3CCSSCC[n+]3ccccc3/C=C/c3ccc4c(c3)OCCN4C)ccc21]
42
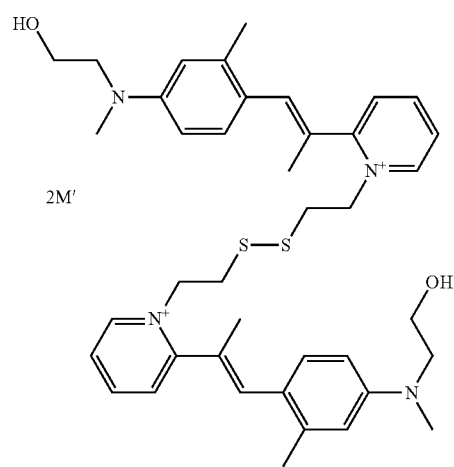 [SMILES: C/C(=C\c1ccc(N(C)CCO)cc1C)c1cccc[n+]1CCSSCC[n+]1ccccc1/C(C)=C/c1ccc(N(C)CCO)cc1C]
43

-continued
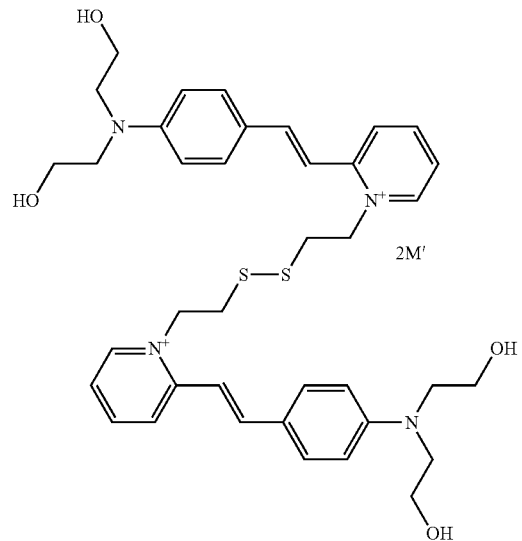 [SMILES: OCCN(CCO)c1ccc(/C=C/c2cccc[n+]2CCSSCC[n+]2ccccc2/C=C/c2ccc(N(CCO)CCO)cc2)cc1]
44
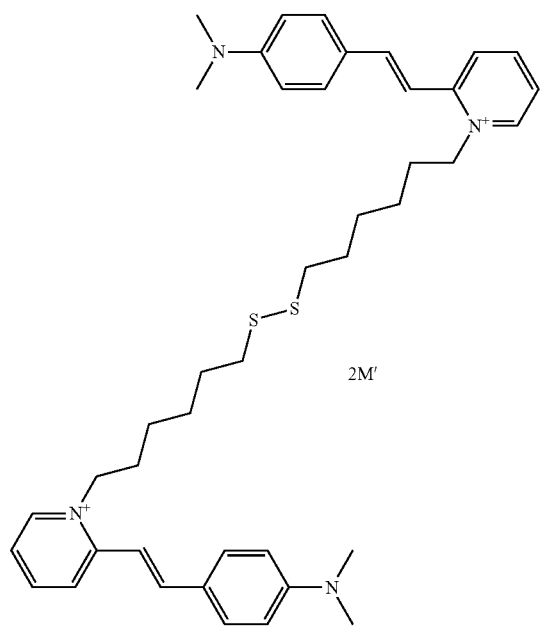 [SMILES: CN(C)c1ccc(/C=C/c2cccc[n+]2CCCCCCSSCCCCCC[n+]2ccccc2/C=C/c2ccc(N(C)C)cc2)cc1]
45
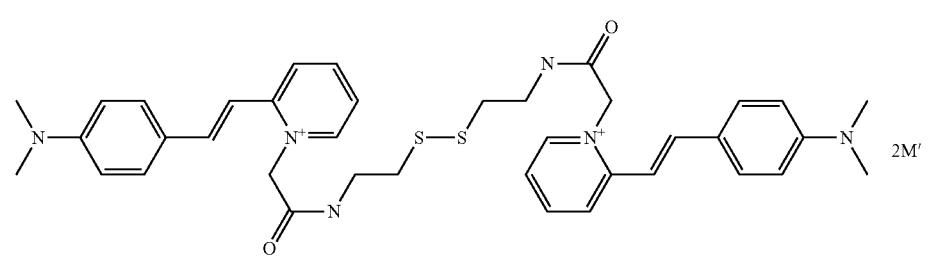
46

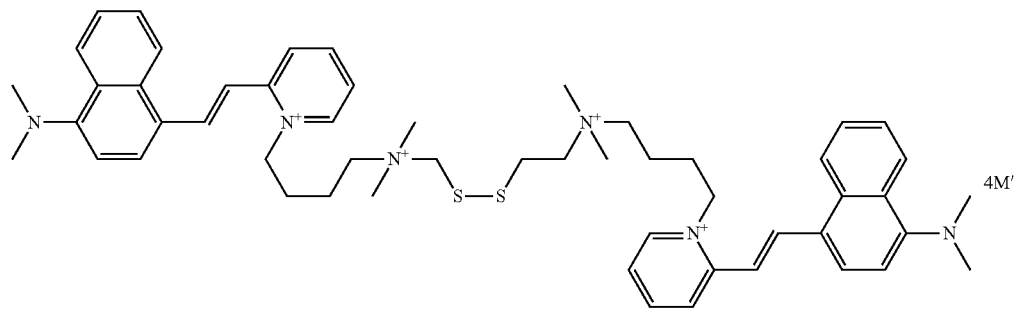
47
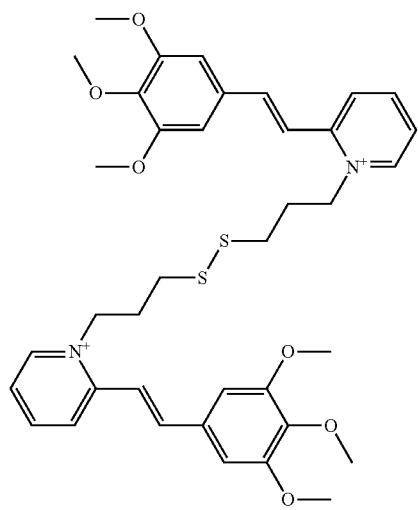 [SMILES: COc1cc(/C=C/c2cccc[n+]2CCCSSCCC[n+]2ccccc2/C=C/c2cc(OC)c(OC)c(OC)c2)cc(OC)c1OC]
48
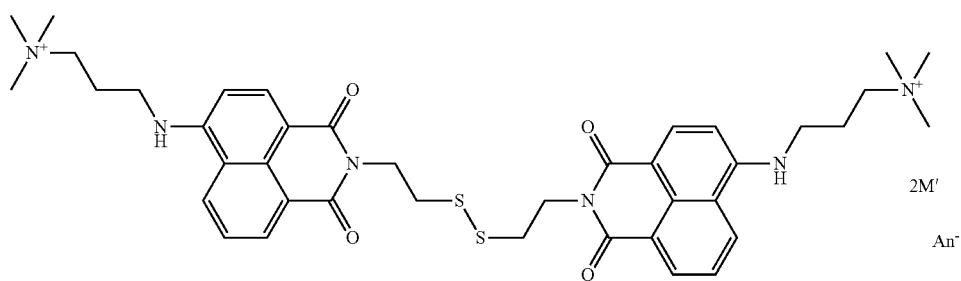
49
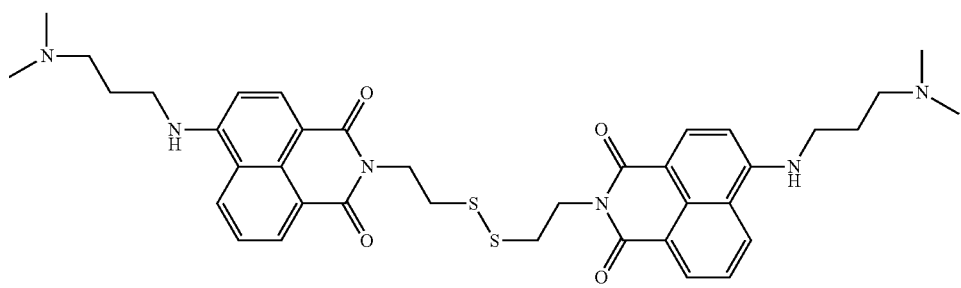
49a

-continued
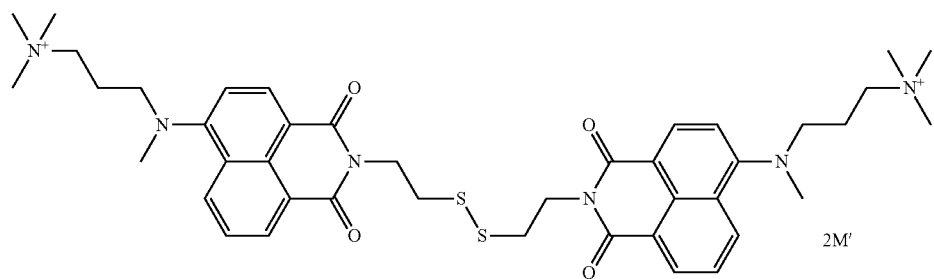
50
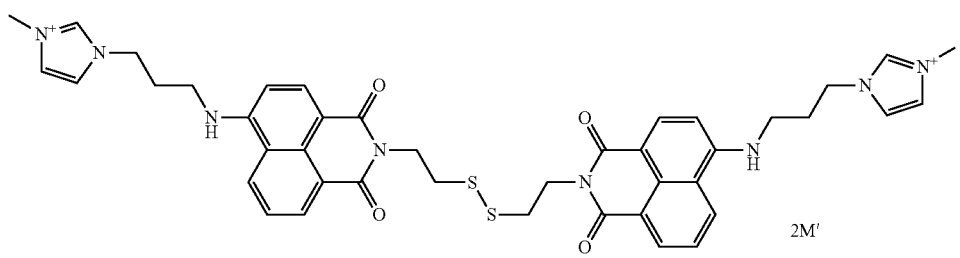
51
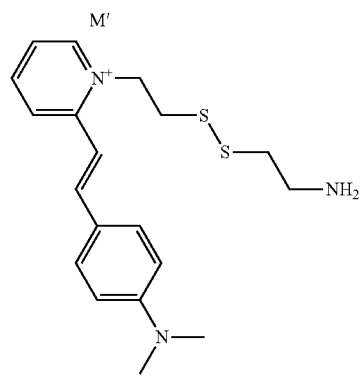 [SMILES: CN(C)c1ccc(/C=C/c2cccc[n+]2CCSSCCN)cc1]
52
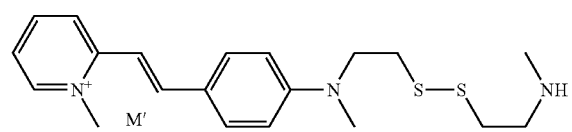 [SMILES: CNCCSSCCN(C)c1ccc(/C=C/c2cccc[n+]2C)cc1]
53
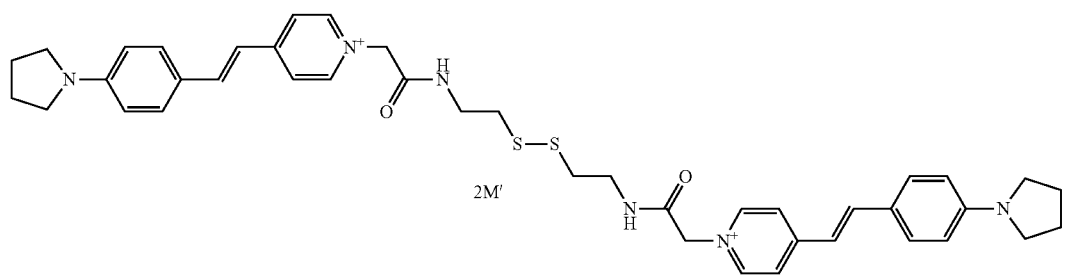 [SMILES: O=C(C[n+]1ccc(/C=C/c2ccc(N3CCCC3)cc2)cc1)NCCSSCCNC(=O)C[n+]1ccc(/C=C/c2ccc(N3CCCC3)cc2)cc1]
54
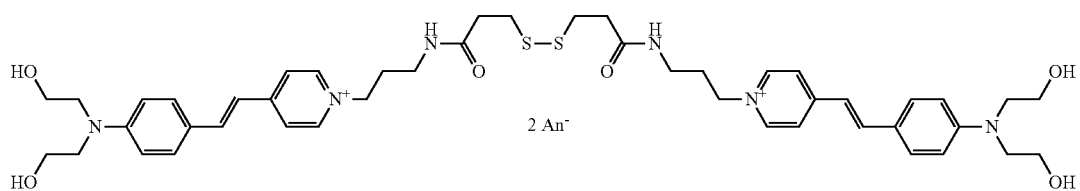 [SMILES: O=C(CCSSCCC(=O)NCCC[n+]1ccc(/C=C/c2ccc(N(CCO)CCO)cc2)cc1)NCCC[n+]1ccc(/C=C/c2ccc(N(CCO)CCO)cc2)cc1]
55

-continued
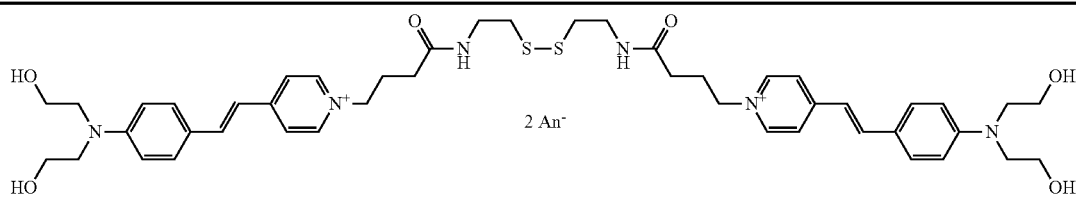
56
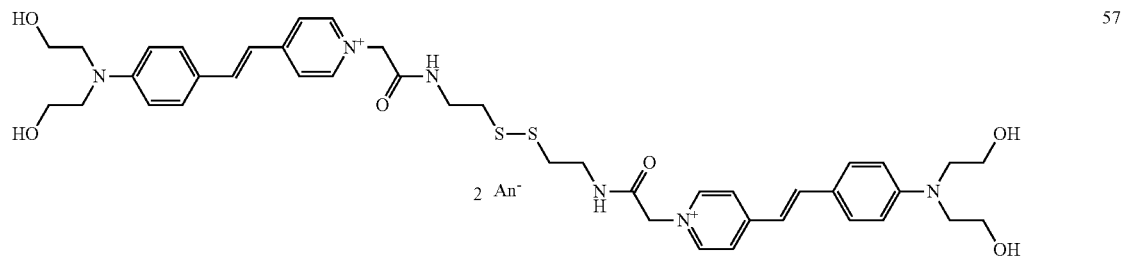
57
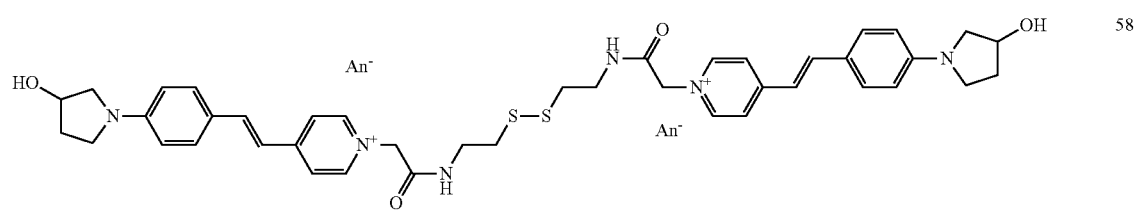
58
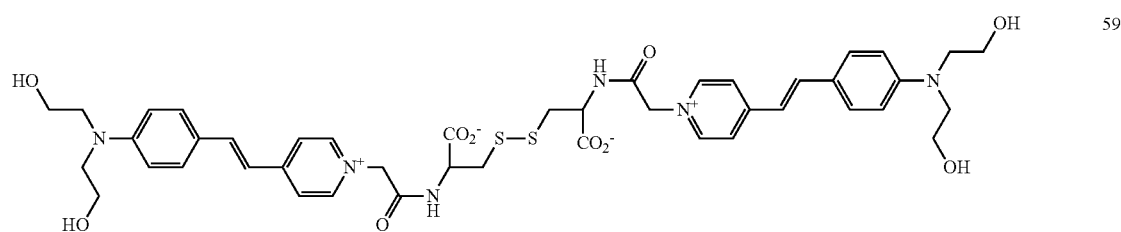
59
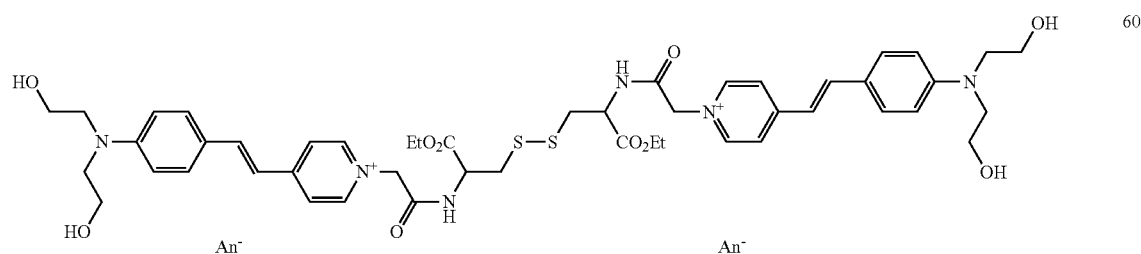
60
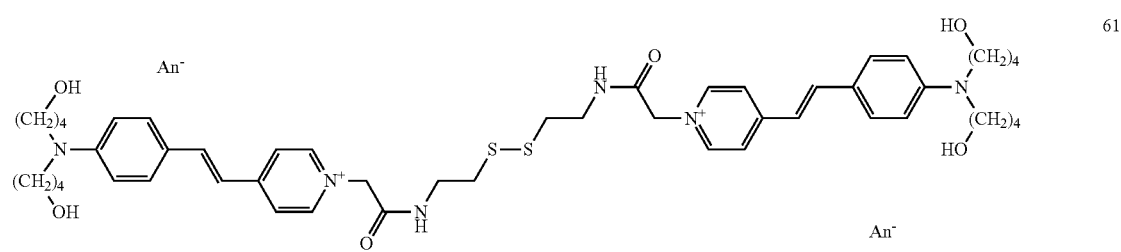
61
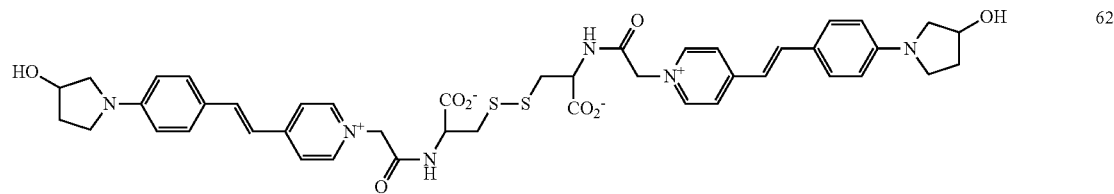
62

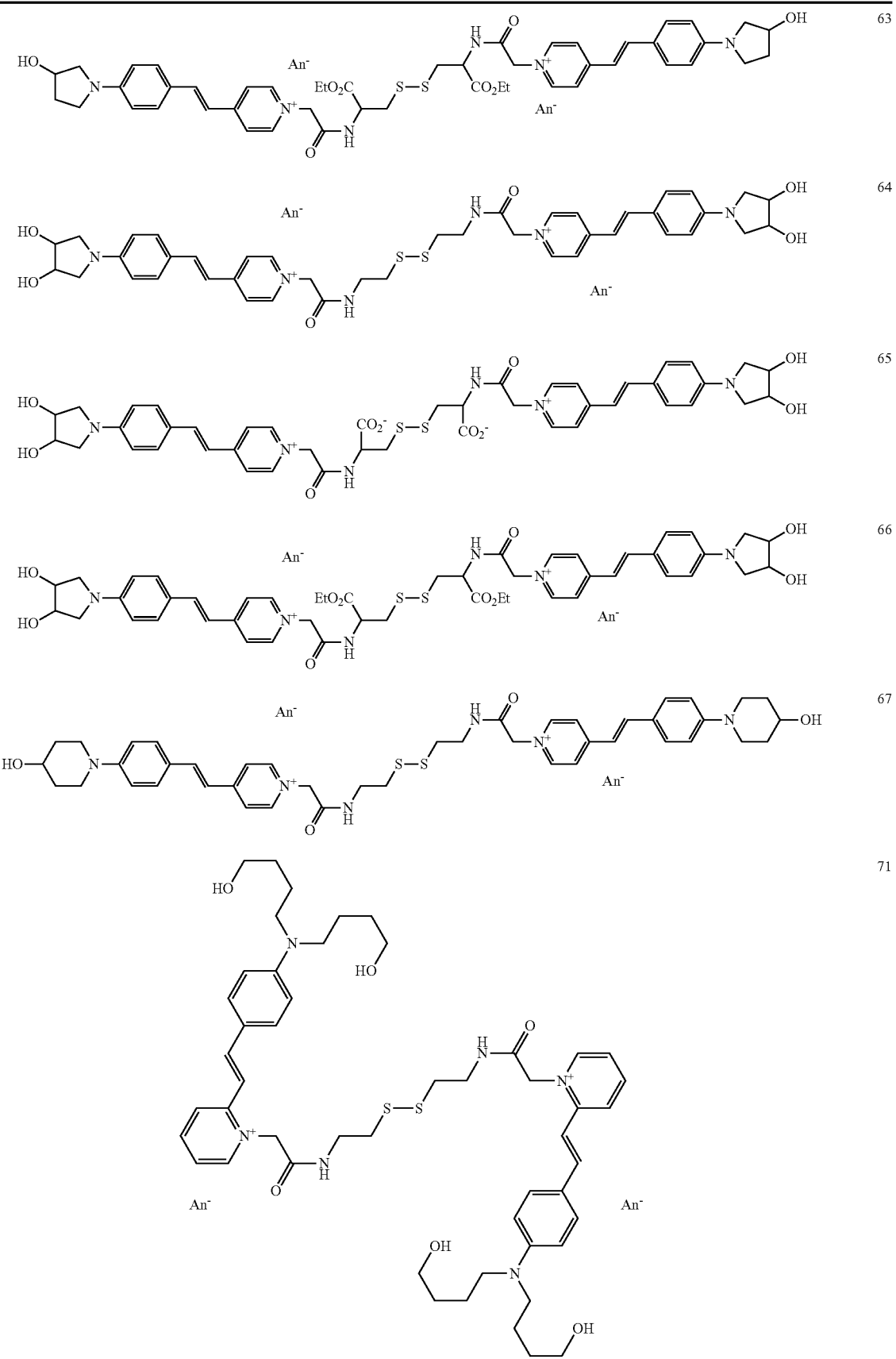

-continued
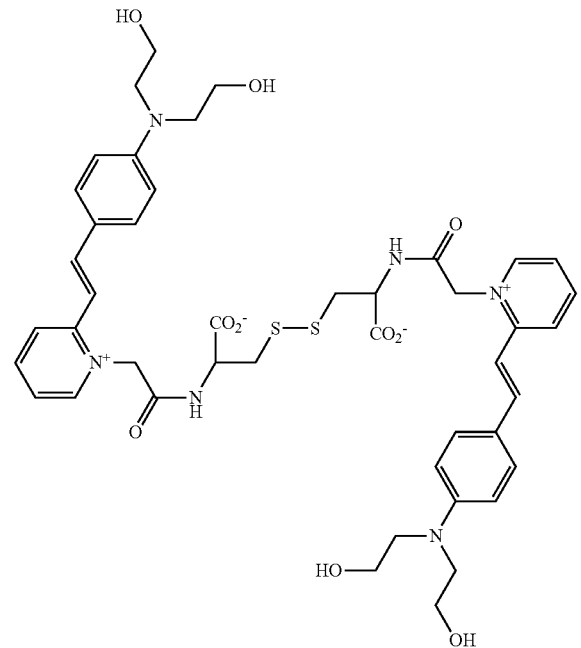
72
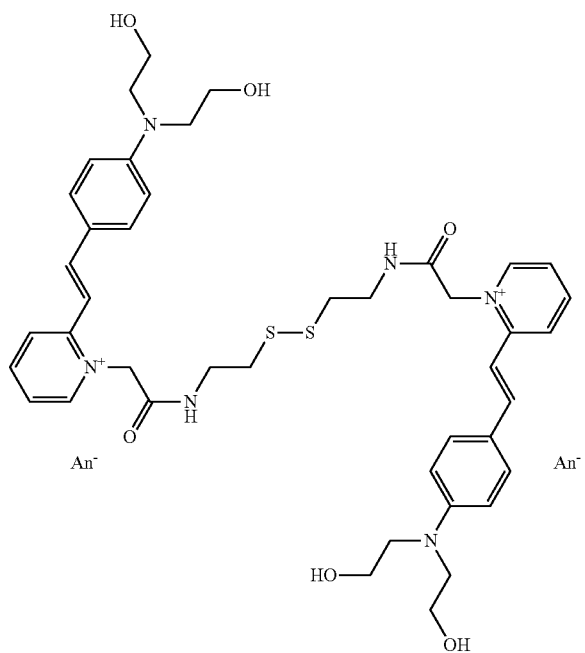 [SMILES: O=C(C[n+]1ccccc1/C=C/c1ccc(N(CCO)CCO)cc1)NCCSSCCNC(=O)C[n+]1ccccc1/C=C/c1ccc(N(CCO)CCO)cc1]
73

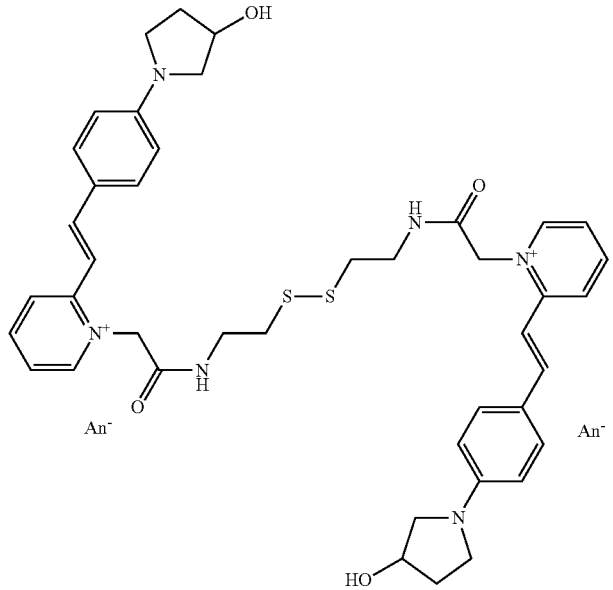 [SMILES: O=C(C[n+]1ccccc1/C=C/c1ccc(N2CCC(O)C2)cc1)NCCSSCCNC(=O)C[n+]1ccccc1/C=C/c1ccc(N2CCC(O)C2)cc1]
74
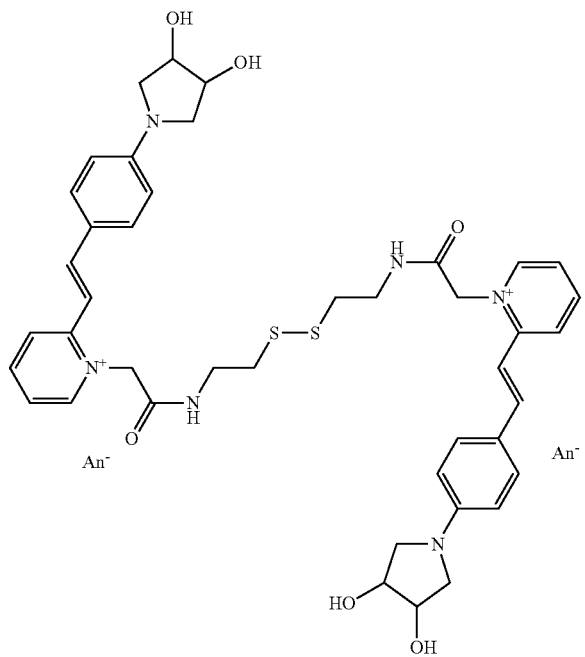 [SMILES: O=C(C[n+]1ccccc1/C=C/c1ccc(N2CC(O)C(O)C2)cc1)NCCSSCCNC(=O)C[n+]1ccccc1/C=C/c1ccc(N2CC(O)C(O)C2)cc1]
75
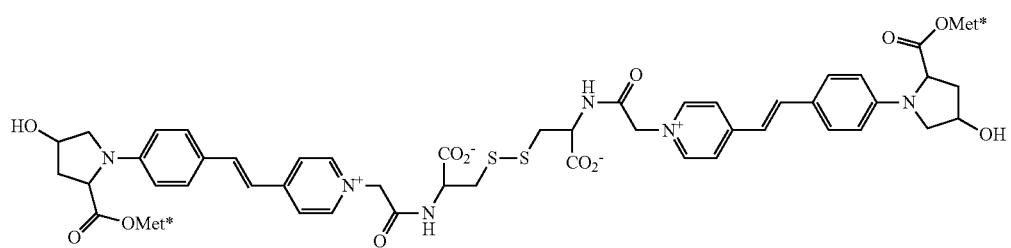
77

-continued
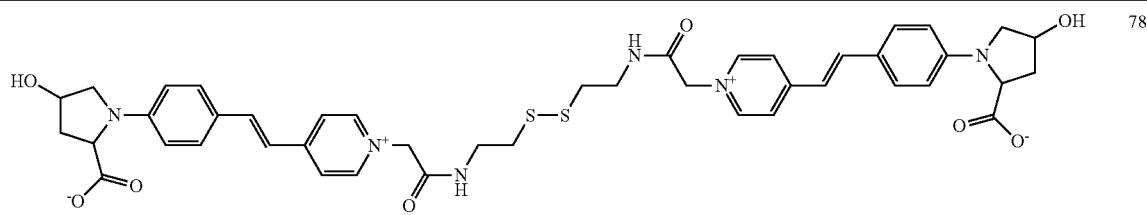
78
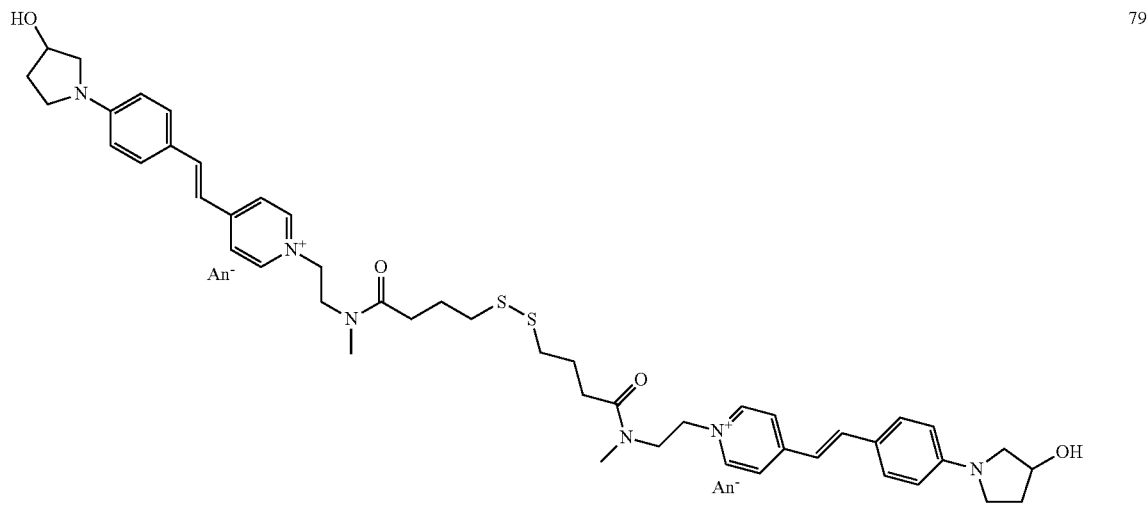
79
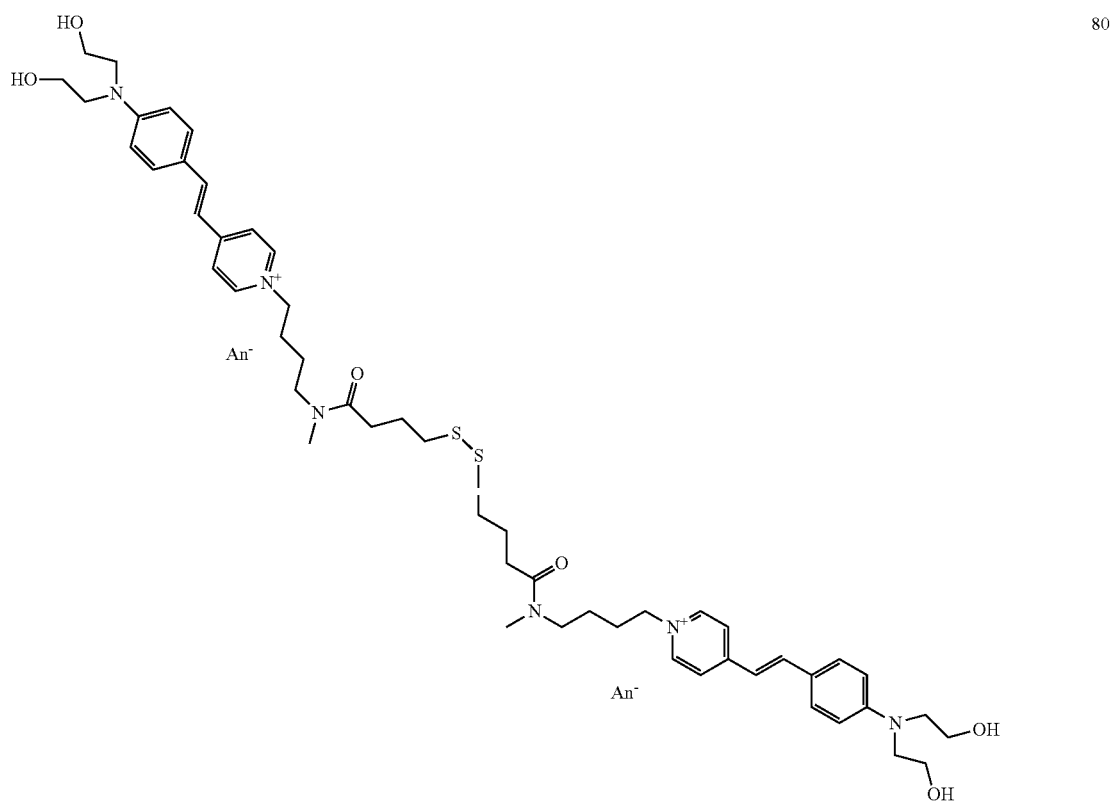
80

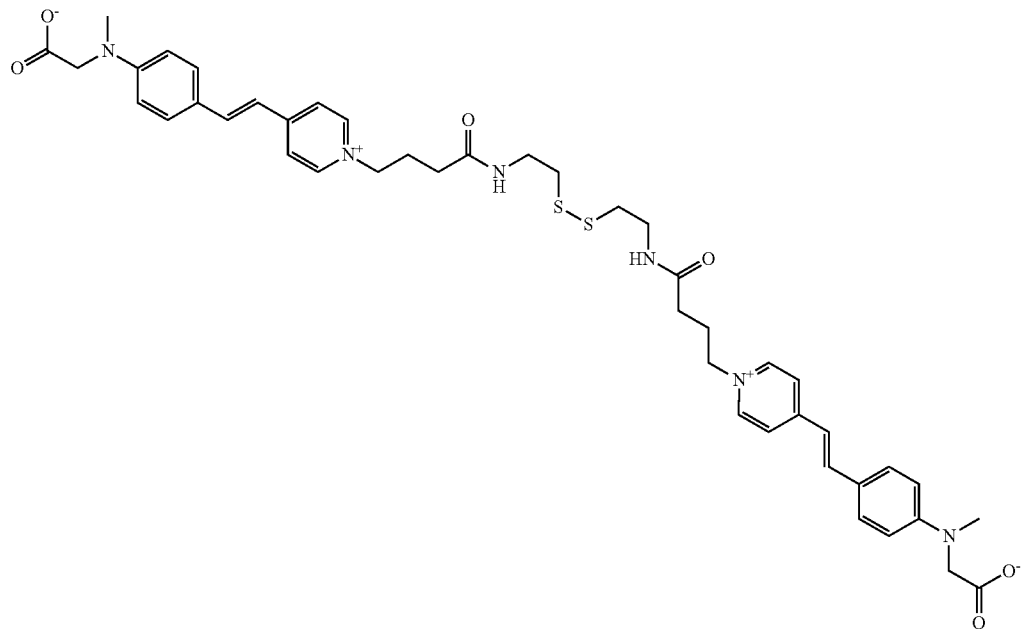 [SMILES: CN(CC(=O)[O-])c1ccc(/C=C/c2cc[n+](CCCC(=O)NCCSSCCNC(=O)CCC[n+]3ccc(/C=C/c4ccc(N(C)CC(=O)[O-])cc4)cc3)cc2)cc1]
81
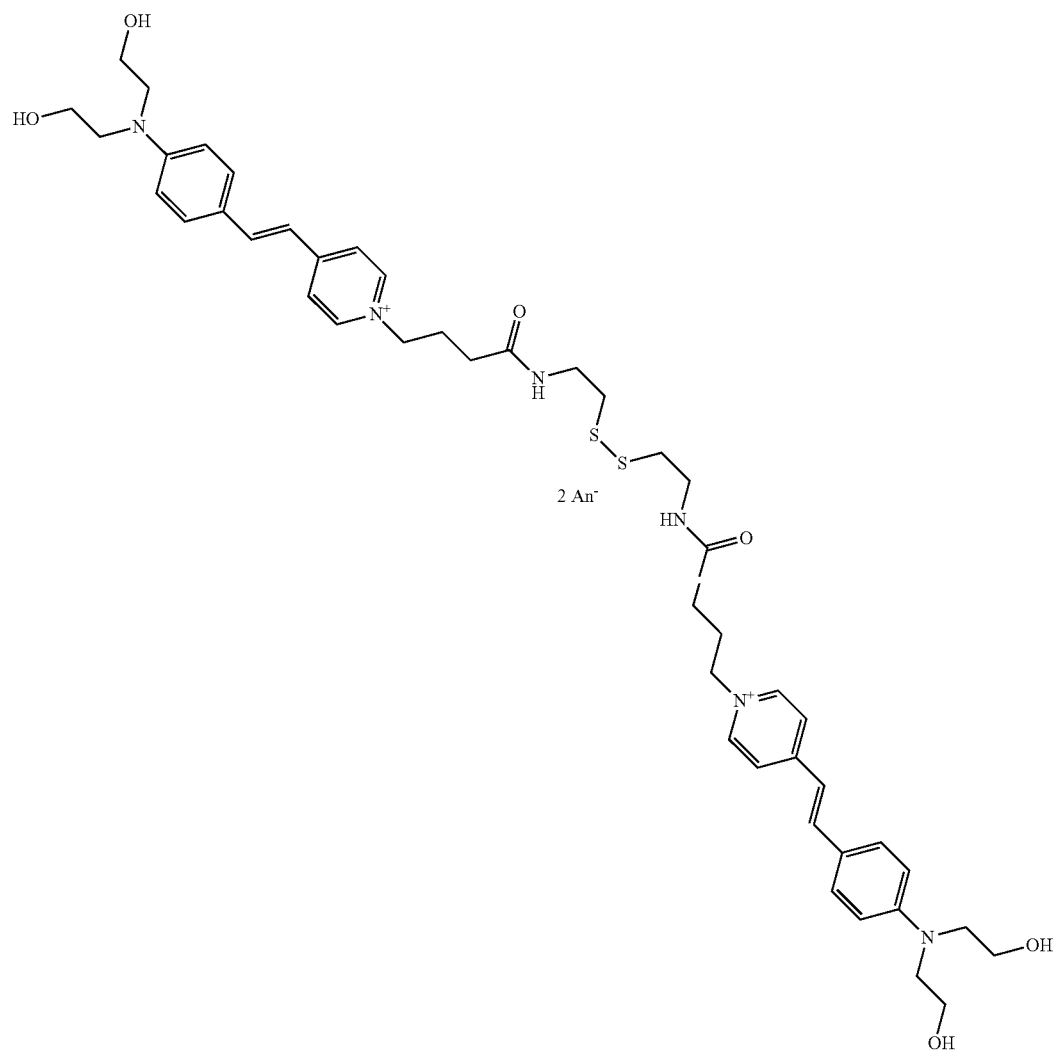 [SMILES: O=C(CCC[n+]1ccc(/C=C/c2ccc(N(CCO)CCO)cc2)cc1)NCCSSCCNC(=O)CCC[n+]1ccc(/C=C/c2ccc(N(CCO)CCO)cc2)cc1]
82

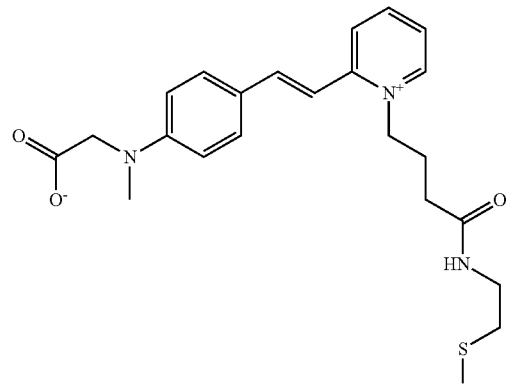
83
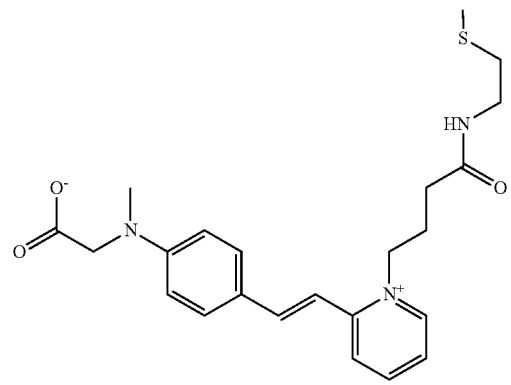
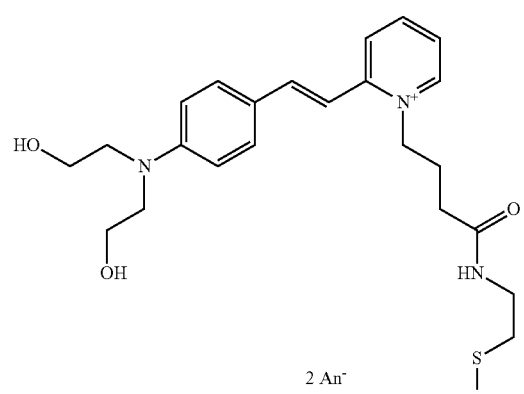
84
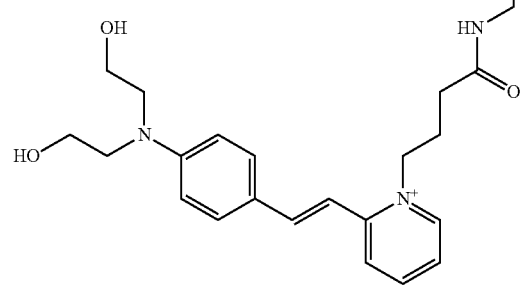

-continued
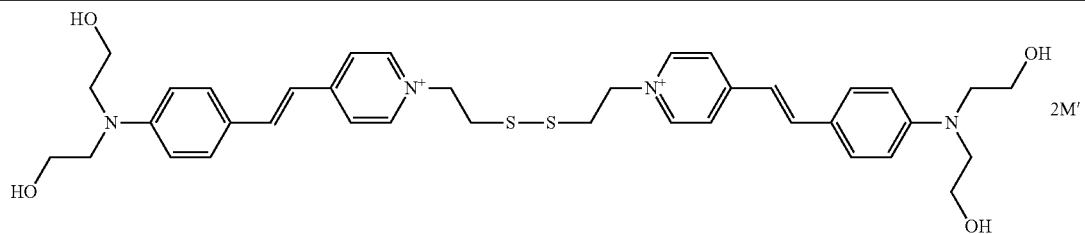
85
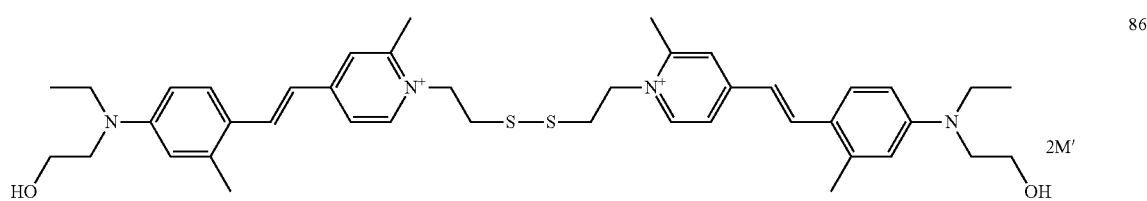
86
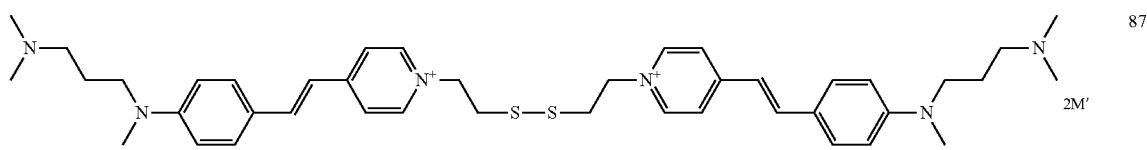
87
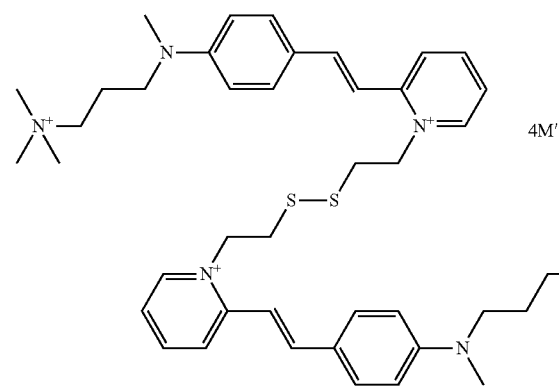
88
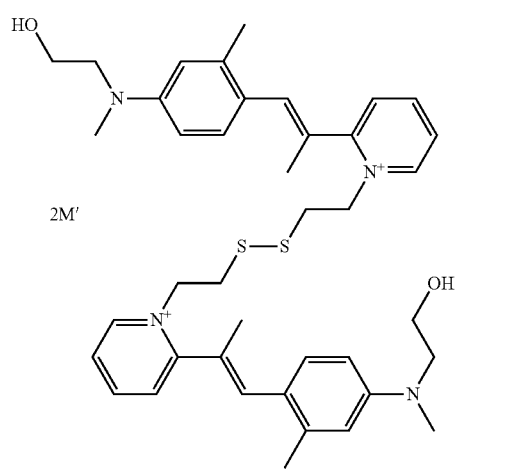 [SMILES: C/C(=C\c1ccc(N(C)CCO)cc1C)c1cccc[n+]1CCSSCC[n+]1ccccc1/C(C)=C/c1ccc(N(C)CCO)cc1C]
89

-continued
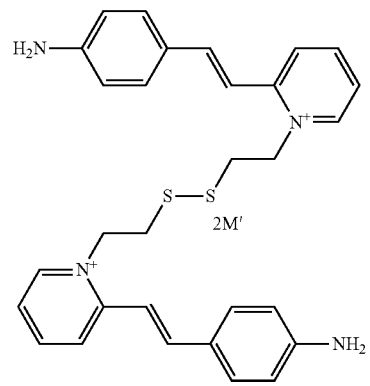 [SMILES: Nc1ccc(/C=C/c2cccc[n+]2CCSSCC[n+]2ccccc2/C=C/c2ccc(N)cc2)cc1]
90
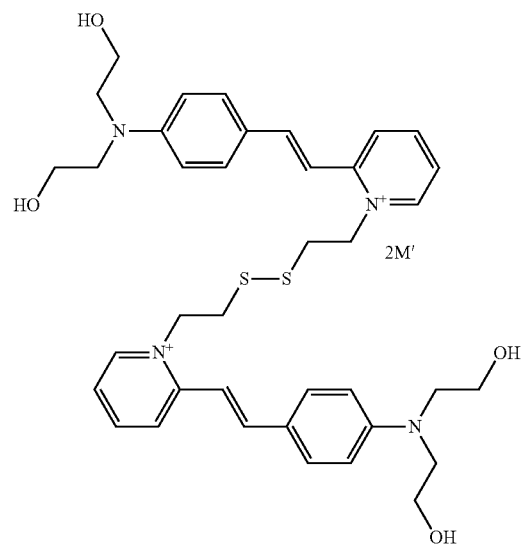 [SMILES: OCCN(CCO)c1ccc(/C=C/c2cccc[n+]2CCSSCC[n+]2ccccc2/C=C/c2ccc(N(CCO)CCO)cc2)cc1]
91
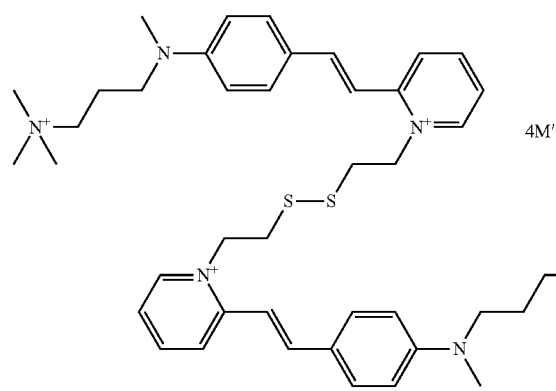
92
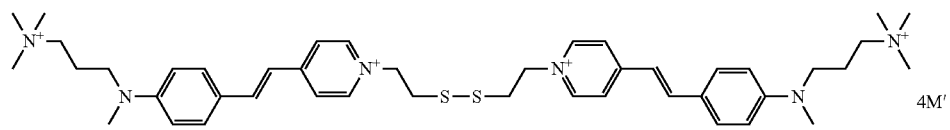
103
wherein An⁻ and M', which may be identical or different, are anionic counterions.

wherein An⁻ and M', which may be identical or different, are anionic counterions.

13. The process according to claim 1, wherein applying water vapor to the keratin fibers is performed extemporaneously with applying to the keratin fibers at least one cationic direct dye.

14. The process according to claim 1, wherein applying water vapor to the keratin fibers is performed after applying to the keratin fibers at least one cationic direct dye.

15. The process according to claim 1, wherein the process does not use a reducing agent.

16. The process according to claim 1, wherein the process does not use a chemical oxidizing agent.

17. The process according to claim 1, wherein the water vapor has a temperature of greater than about 80° C.

18. The process according to claim 1, wherein the process lightens keratin fibers having a tone depth of less than about 6.

19. The process according to claim 1, wherein the process grafts the at least one cationic direct dye onto the keratin fibers.

* * * * *

UNITED STATES PATENT AND TRADEMARK OFFICE
CERTIFICATE OF CORRECTION

PATENT NO. : 8,840,684 B2
APPLICATION NO. : 13/993416
DATED : September 23, 2014
INVENTOR(S) : Andrew Greaves Page 1 of 3

It is certified that error appears in the above-identified patent and that said Letters Patent is hereby corrected as shown below:

In the Specification

Columns 63, 64, 129 and 130, chemical structure 80, please delete and replace with the chemical structure 80 on the attached page.

Columns 65, 66, 131 and 132, chemical structure 82, please delete and replace with the chemical structure 82, on the attached page.

Columns 67 and 68, chemical structures 83 and 84, please delete and replace with the chemical structures 83 and 84 on the attached page.

In the Claims

Claim 9, column 96, chemical structure (VII'), at the top of the structure, "Rc" should be -- Rg -- (as shown on the attached page.

Claim 10, columns 95 and 96, chemical structure (IX) is missing, please add chemical structure (IX) as shown on the attached page.

Columns 133 and 134, chemical structures 83 and 84, please delete and replace with the chemical structures 83 and 84 on the attached page.

Signed and Sealed this
Fifth Day of January, 2016

Michelle K. Lee
*Director of the United States Patent and Trademark Office*

CERTIFICATE OF CORRECTION (continued)
U.S. Pat. No. 8,840,684 B2

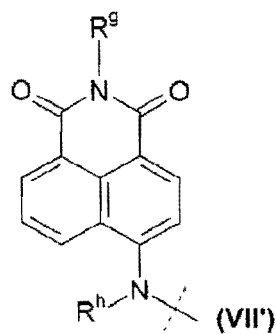

(VII')

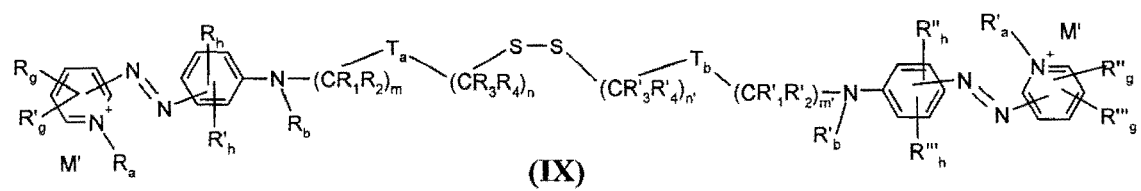

(IX)

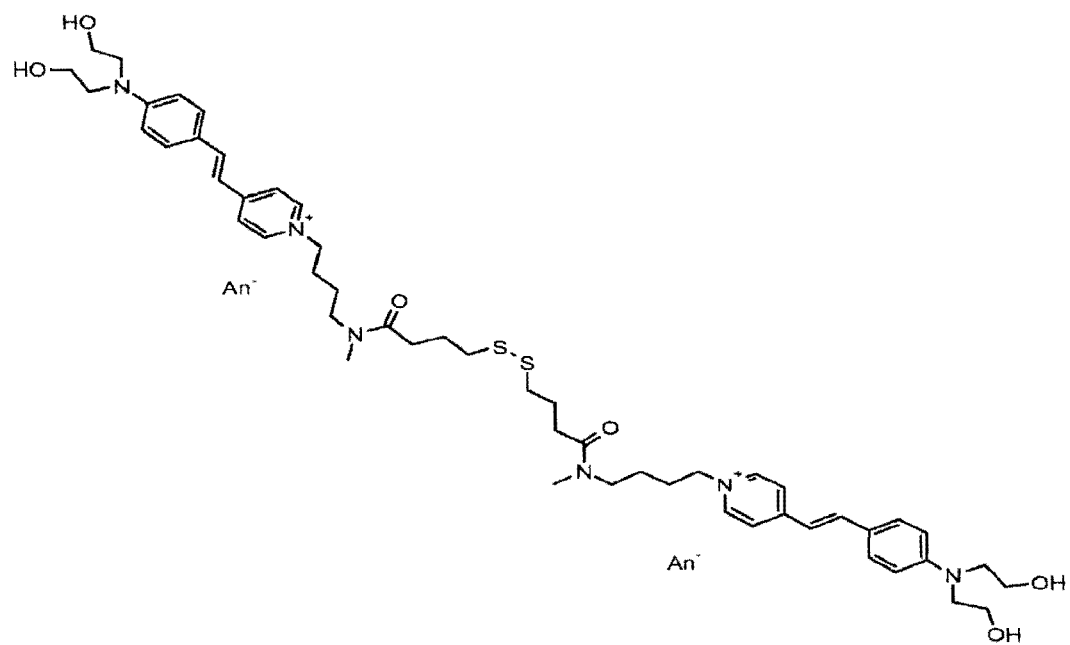

80

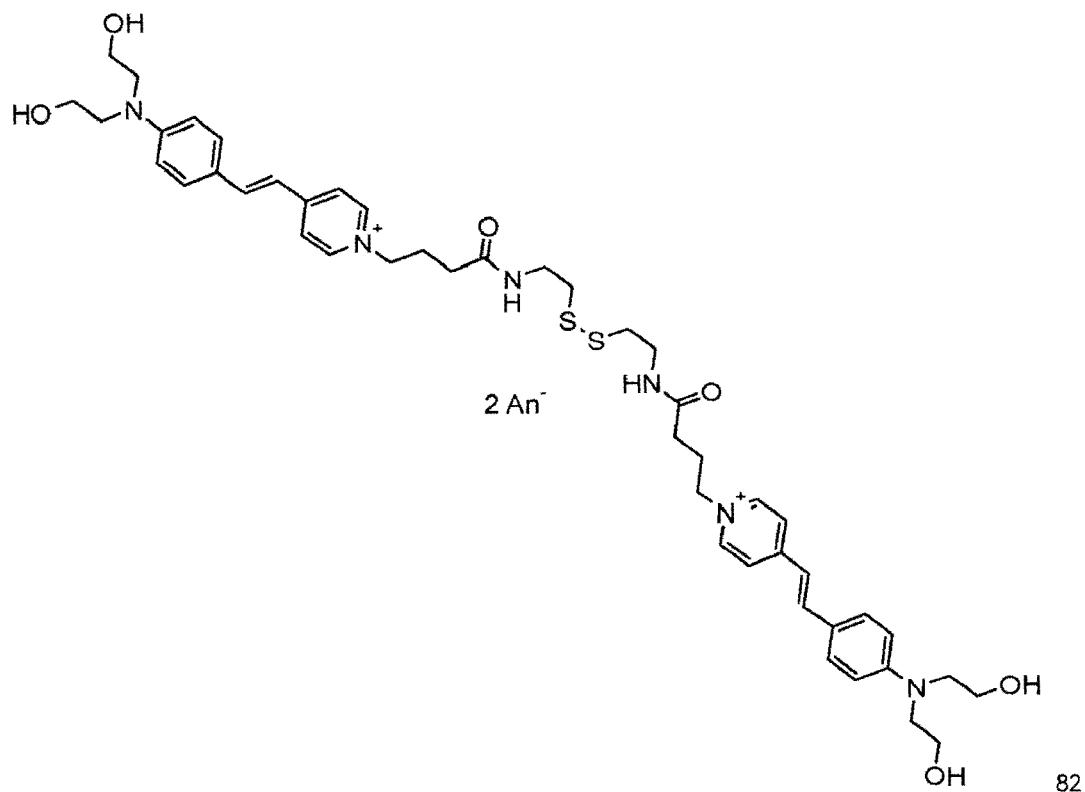
82
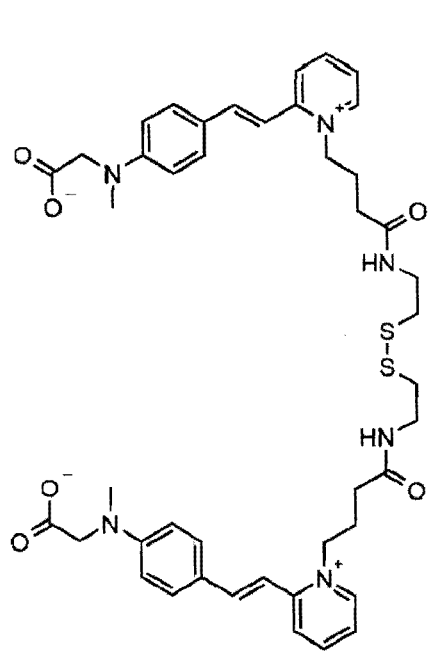
83
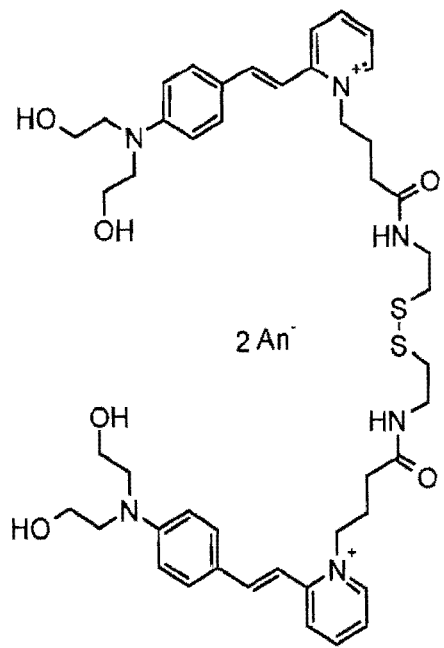
84